United States Patent
Mueller et al.

(10) Patent No.: US 7,014,838 B2
(45) Date of Patent: Mar. 21, 2006

(54) USE OF BIOMOLECULAR TARGETS IN THE TREATMENT AND VISUALIZATION OF BRAIN TUMORS

(75) Inventors: Sabine Mueller, San Francisco, CA (US); Mirella Gonzalez-Zulueta, Pacifica, CA (US); Erik Foehr, Novato, CA (US); Daniel J. Chin, Foster City, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 61 days.

(21) Appl. No.: 10/329,258

(22) Filed: Dec. 23, 2002

(65) Prior Publication Data

US 2006/0024233 A1 Feb. 2, 2006

Related U.S. Application Data

(60) Provisional application No. 60/343,422, filed on Dec. 27, 2001.

(51) Int. Cl.
*A61K 51/00* (2006.01)
*A61M 36/14* (2006.01)

(52) U.S. Cl. .................. 424/1.69; 424/1.11; 424/1.49; 424/1.65; 424/9.1; 424/9.2

(58) Field of Classification Search ............... 424/1.11, 424/1.65, 1.69, 9.1, 9.2, 9.3, 9.4, 9.5, 9.6, 424/9.7, 9.8, 1.49, 1.93; 514/2, 9, 12; 530/300
See application file for complete search history.

(56) References Cited

OTHER PUBLICATIONS

Accession No. AF071202.
Accession No. AF152331.
Accession No. AY007162.
Accession No. BC000214.
Accession No. BC000726.
Accession No. BC004892.
Accession No. D13866.
Accession No. NM_004720.
Accession No. XM_004372.
Accession No. XM_006607.
Accession No. XM_007289.
Accession No. XM_017039.
Accession No. XM_071910.
Accession No. XM_008971.
Accession No. XM_011168.
Mariani et al., Glioma cell Motility is Associated With Reduced Transription of Proapoptotic and Proliferatio Genes: A CNDA Microarray Analysis, Journal of Neuro-Oncology, (2001), 53: 161-176.
Markert et al., Differential Gene Expression Profiling in human Brain Tumors, Physiol. Genomics, (2001), 5: 21-33.
Kroes et al., The Identification of Novel Therapeutic Targets for the Treatment of Malignant Brain Tumors, Cancer Letters, (2000), 156: 191-198.
Reis et al., Short Communication Genetic Profile of Gliosarcomas, American Journal of Pathology, (2003), 156: (2) 245-432.
Yano et al., Differential Expression of β-Catenin in Human Glioblastoma Multiforme and Normal Brain Tissue, Neurological Research, (2000), 22: 650-656.

*Primary Examiner*—Dameron L. Jones
(74) *Attorney, Agent, or Firm*—Pamela J. Sherwood; Bozicevic, Field & Francis LLP; Rebecca D. Taylor

(57) ABSTRACT

The present invention relates to the use of proteins that are differentially expressed in primary brain tumor tissues, as compared to normal brain tissues, as biomolecular targets for brain tumor treatment therapies. Specifically, the present invention relates to the use of immunotherapeutic and immunoimaging agents, which specifically bind to one or more of the identified brain tumor protein targets. The present invention also provides compounds and pharmaceutically acceptable compositions for administration in the methods of the invention. Nucleic acid probes specific for the spliced mRNA encoding these variants and affinity reagents specific for the novel proteins are also provided.

20 Claims, No Drawings

USE OF BIOMOLECULAR TARGETS IN THE TREATMENT AND VISUALIZATION OF BRAIN TUMORS

This application claims benefit to provisional application 60/343,422, filed Dec. 27, 2001.

BACKGROUND OF THE INVENTION

Among tumors, those of the brain are considered to have one of the least favorable prognoses for long term survival: the average life expectancy of an individual diagnosed with a central nervous system (CNS) tumor is just eight to twelve months. Several unique characteristics of both the brain and its particular types of neoplastic cells create daunting challenges for the complete treatment and management of brain tumors. Among these are the physical characteristics of the intracranial space; the relative biological isolation of the brain from the rest of the body; the relatively essential and irreplaceable nature of the organ mass; and the unique nature of brain tumor cells.

The intracranial space and physical layout of the brain create significant obstacles to treatment and recovery. The brain is primarily comprised of astrocytes, which make up the majority of the brain mass, and serve as a scaffold and support for the neurons, neurons, which carry the actual electrical impulses of the nervous system, and a minor contingent of other cells, such as insulating oligodendrocytes that produce myelin. These cell types give rise to primary brain tumors, including astrocytomas, neuroblastomas, glioblastomas, oligodendrogliomas, and the like.

The brain is encased in the rigid shell of the skull, and is cushioned by the cerebrospinal fluid. Because of the relatively small volume of the skull cavity, minor changes in the volume of tissue in the brain can dramatically increase intracranial pressure, causing damage to the entire organ. Thus, even small tumors can have a profound and adverse affect on the brain's function. The cramped physical location of the cranium also makes surgery and treatment of the brain a difficult and delicate procedure. However, because of the dangers of increased intracranial pressure from the tumor, surgery is often the first strategy of attack in treating brain tumors.

In addition to its physical isolation, the brain is chemically and biologically isolated from the rest of the body by the "Blood-Brain-Barrier" (or BBB). This physiological phenomenon is due to the "tightness" of the epithelial cell junctions in the lining of the blood vessels in the brain. Nutrients, which are actively transported across the cell lining, can reach the brain, but other molecules from the bloodstream are excluded. This prevents toxins, viruses, and other potentially dangerous molecules from entering the brain cavity. However, it also prevents therapeutic molecules, including many chemotherapeutic agents that are useful in other types of tumors, from crossing into the brain. Thus, many therapies directed at the brain must be delivered directly into the brain cavity, e.g. by an Ommaya reservoir, or administered in elevated dosages to ensure the diffusion of an effective amount across the BBB.

With the difficulties of administering chemotherapies to the brain, radiotherapy approaches have also been attempted. However, the amount of radiation necessary to completely destroy potential tumor-producing cells also produce unacceptable losses of healthy brain tissue. The retention of patient cognitive function while eliminating the tumor mass is another challenge to brain tumor treatment. Neoplastic brain cells are often pervasive, and travel throughout the entire brain mass. Thus, it is impossible to define a true "tumor margin," unlike, for example, in lung or bladder cancers. Unlike reproductive (ovarian, uterine, testicular, prostate, etc.), breast, kidney, or lung cancers, the entire organ, or even significant portions, cannot be removed to prevent the growth of new tumors. In addition, brain tumors are very heterogeneous, with different cell doubling times, treatment resistances, and other biochemical idiosyncrasies between the various cell populations that make up the tumor. This pervasive and variable nature greatly adds to the difficulty of treating brain tumors while preserving the health and function of normal brain tissue.

Although current surgical methods offer considerably better post-operative life for patients, current combination therapy methods (surgery, low-dosage radiation, and chemotherapy) have only improved the life expectancy of patients by one month, as compared to the methods of 30 years ago. Without effective agents to prevent the growth of brain tumor cells that are present outside the main tumor mass, the prognosis for these patients cannot be significantly improved. Although some immuno-affinity agents have been proposed and tested for the treatment of brain tumors, see, for example, the tenascin-targeting agents described in U.S. Pat. No. 5,624,659, these agents have not proven sufficient for the treatment of brain tumors. Thus, therapeutic agents which are directed towards new molecular targets, and are capable of specifically targeting and killing brain tumor cells, are urgently needed for the treatment of brain tumors.

Relevant Literature

Analysis of differential gene expression in glioblastoma may be found in, for example, Mariani et al. (2001) *J Neurooncol* 53(2):161–76; Markert et al. (2001) *Physiol Genomics* 5(1):21–33; Yano et al. (2000) *Neurol Res* 22(7): 650–6; Kroes et al. (2000) *Cancer Lett* 156(2):191–8; and Reis et al. (2000) *Am J Pathol* 156(2):425–32, among others.

SUMMARY OF THE INVENTION

The present invention provides methods and reagents for specifically targeting brain tumor neoplastic cells for both therapeutic and imaging purposes, by targeting brain tumor protein targets ($T_{BT}$). These targets have been identified as being overexpressed in brain tumors, and thus allow for the selective inhibition of cell function or selective marking for visualization with therapeutic or visualizing compositions which have a specific affinity for these protein targets. The invention also provides methods for the identification of compounds that modulate the expression of genes or the activity of gene products involved in such tumors, as well as methods for the treatment of disease by administering such compounds to individuals suffering from such tumors.

DETAILED DESCRIPTION OF THE EMBODIMENTS

Brain tumor protein targets and genes that are differentially expressed between brain tumor tissue and normal brain tissue are provided herein. Differential cloning between cancerous and normal brains has identified brain tumor protein target genes by DNA sequence analysis. Genes and their protein products that are up-regulated in glioblastoma are important because they provide a specific marker for neoplastic cells, and are expected to mediate the initiation and progression of brain tumors. Inhibition of the gene and/or protein activity can be advantageous in treating brain tumors, e.g. glioblastoma multiforme; ependymoma;

glioma; astrocytoma; medulloblastoma; neuroglioma; oligodendroglioma; meningioma, etc. The overexpressed brain tumor protein targets provide excellent targets for immunotherapeutic agents that either deliver cytotoxic agents to directly promote tumor cell death, or that alter the function of the brain tumor protein targets to inhibit the normal physiology of the tumor cell. In addition, immunoimaging agents targeted to the brain tumor protein targets can be utilized to visualize the tumor mass in diagnostic methods, e.g. magnetic resonance imaging (MRI), radiography, etc. and/or in surgery, e.g. by the use of optically visual dye moieties in an immunoimaging agent, etc.

Therapeutic and prophylactic treatment methods for individuals suffering, or at risk of brain tumor, involve administering either a therapeutic or prophylactic amount of an agent that modulates the activity of $T_{BT}$ protein or gene, or which specifically binds to a $T_{BT}$ protein, for example, a chemotherapeutic agent coupled to a $T_{BT}$ specific binding moiety.

Screening methods may involve conducting various types of assays to identify agents that modulate the expression or activity of a $T_{BT}$ gene or protein, or may involve screening for specific binding activity to a $T_{BT}$ gene or protein. Lead compounds and/or binding moieties identified during these screens can serve as the basis for the synthesis of more active analogs. Lead compounds and/or active analogs generated therefrom can be formulated into pharmaceutical compositions effective in treating brain tumors.

Disease Conditions

The present methods are applicable to brain tumors, particularly glioblastoma. In general, the goals of brain tumor treatments are to remove as many tumor cells as possible, e.g. with surgery, kill as many of the cells left behind after surgery as possible with radiation and/or chemotherapy, and put remaining tumor cells into a nondividing, quiescent state for as long as possible with radiation and chemotherapy. Careful imaging surveillance is a crucial part of medical care, because tumor regrowth requires alteration of current treatment, or, for patients in the observation phase, restarting treatment.

Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, usually cerebral tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are highly malignant, primitive tumors that arise in the posterior fossa, primarily in children. Meningiomas are common intracranial tumors that arise in the meninges and compress the underlying brain. Meningiomas are usually benign, but some "atypical" meningiomas may recur locally, and some meningiomas are frankly malignant and may invade the brain or metastasize. Atypical and malignant meningiomas are not as common as benign meningiomas. Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

The symptoms of both primary and metastatic brain tumors depend mainly on the location in the brain and the size of the tumor. Since each area of the brain is responsible for specific functions, the symptoms will vary a great deal. Tumors in the frontal lobe of the brain may cause weakness and paralysis, mood disturbances, difficulty thinking, confusion and disorientation, and wide emotional mood swings. Parietal lobe tumors may cause seizures, numbness or paralysis, difficulty with handwriting, inability to perform simple mathematical problems, difficulty with certain movements, and loss of the sense of touch. Tumors in the occipital lobe can cause loss of vision in half of each visual field, visual hallucinations, and seizures. Temporal lobe tumors can cause seizures, perceptual and spatial disturbances, and receptive aphasia. If a tumor occurs in the cerebellum, the person may have ataxia, loss of coordination, headaches, and vomiting. Tumors in the hypothalamus may cause emotional changes, and changes in the perception of hot and cold. In addition, hypothalamic tumors may affect growth and nutrition in children. With the exception of the cerebellum, a tumor on one side of the brain causes symptoms and impairment on the opposite side of the body.

Other disorders of the nervous system that may be treated or imaged with the compositions of the present invention include, but are not limited to ischemic stroke, brain cancer, epilepsy, schizophrenia, depression, Alzheimer's Disease, Parkinson's Disease, Huntington's Chorea, traumatic head injury, dementia, coma, stupor, headache (and other neurological pain), vertigo, weakness, myasthenia gravis (and other disorders of the neuromuscular junction), ataxia and cerebellar disorders, cranial nerve disorders (such as Bell's Palsy), cerebrovascular disorders, infectious disorders including bacterial, fungal, viral and parasitic infections, multiple sclerosis, and other complications associated with pregnancy, medical illness, alcohol and substance abuse, toxins and metabolic deficiencies.

Identification of $T_{BT}$ Genes

A genetic sequence that comprises all or a part of a cDNA sequence that is differentially expressed in brain tumor cells, particularly glioblastoma cells, relative to expression in normal, or non-disease conditions, is herein termed a "$T_{BT}$ gene", which encode "$T_{BT}$ proteins". $T_{BT}$ genes were identified by creating cDNA libraries from glioblastoma tissues. The cDNA's from control and disease states were subjected to kinetic re-annealing hybridization during which normalization of transcript abundances and enrichment for differentially expressed transcripts (i.e., subtraction) occurs. Only clones displaying a significant transcriptional induction and/or repression were sequenced and carried forward for expression profiling, using a variety of temporal, spatial and disease-related probe sets. Selected clones showing a significant transcriptional induction and/or repression were sequenced and functionally annotated in a proprietary database structure (See WO01/13105). Because large sequence fragments were utilized in the sequencing step, the data generated has a much higher fidelity and specificity than other approaches, such as SAGE. The resulting sequence information was compared to public databases using the BLAST (blastn) and iterative-Smith Waterman analysis for protein sequence comparisons. The results are listed in Table 1. Table 1 includes, in some instances, the human and animal counterparts of a sequence, as indicated by a shared internal reference designation.

TABLE 1

| AGY ID | DESCRIPTION | NUCLEOTIDE ACCESSION | SEQ ID | PROTEIN ACCESSION | SEQ ID | ADDITIONAL ACCESSIONS |
|---|---|---|---|---|---|---|
| AL00003_CP4_M02 | Homo sapiens neuroligin 2 (NLGN2) | XM_071910 | 1 | XP_071910 | 2 | AB037787 |
| AL00003_CP1_H24 | Homo sapiens, guanine nucleotide binding protein (G protein), beta polypeptide 2-like 1, clone MGC:2416 IMAGE:2959178, mRNA, complete cds | BC000214 | 3 | AAH00214 | 4 | (N/A) |
| AL00003_CP1_K19 | Homo sapiens protocadherin gamma B2 (PCDH-gamma-B2) | AF152331 | 5 | AAD43725 | 6 | (N/A) |
| AL00003_CP14_A08 | Homo sapiens similar to protein tyrosine kinase 9 (LOC147023) | XM_017039 | 7 | XP_017039 | 8 | NM_002822 |
| AL00003_CP14_B17 | Homo sapiens ABC transporter MOAT-B (MOAT-B) | AF071202 | 9 | AAC27076 | 10 | NM_005845 |
| AL00003_CP14_M09 | Human mRNA for alpha-catenin | D13866 | 11 | BAA02979 | 12 | XM_038221 |
| AL00003_CP14_P05 | Homo sapiens mitogen-activated protein kinase kinase kinase 4 (MAP3K4) | XM_004372 | 13 | XP_004372 | 14 | NM_005922 |
| SL00043_CP3_P11 | Homo sapiens protein kinase C-like 1 (PRKCL1) | XM_008971 | 15 | XP_008971 | 16 | NM_002741 |
| SL00045_CP2_F22 | Homo sapiens cathepsin O (CTSO) | XM_011168 | 17 | XP_011168 | 18 | NM_001334 |
| SL00093_X_K08 | Homo sapiens endothelial differentiation, lysophosphatidic acid G-protein-coupled receptor, 4 (EDG4) | NM_004720 | 19 | NP_004711 | 20 | NM_004720 |
| SL00095_C_F09 | Homo sapiens clone CDABP0138 | AY007162 | 21 | (N/A) | | NM_004383 |

TABLE 1-continued

| AGY ID | DESCRIPTION | NUCLEOTIDE ACCESSION | SEQ ID | PROTEIN ACCESSION | SEQ ID | ADDITIONAL ACCESSIONS |
|---|---|---|---|---|---|---|
| SL00045_CP1_F01 | Homo sapiens contactin 1 (CNTN1) | XM_006607 | 22 | XP_006607 | 23 | NM_001843 |
| SL00045_CP1_L14 | Homo sapiens, kangai 1 | BC000726 | 24 | AAH00726 | 25 | NM_002231 |
| SL00094_CP2_E05 | Homo sapiens organic cation transporter (LOC57100) | XM_007289 | 26 | XP_007289 | 27 | NM_020372 |
| AL00003_CP2_A10 | Homo sapiens, reticulocalbin 2 | BC004892 | 28 | AAH04892 | 29 | NM_002902 |

Note: This is the sequence table generated for AGYT-008US2 (or 125PUS2). The previously-assigned accession numbers were used for a subset of sequences from provisional filing. The "Additional Accessions" column represents additional nucleotide sequences with updated descriptions and identical homology. These "Additional Accessions" are not included in the sequence listing.
Note: The "Additional Accessions" column represents additional nucleotide sequences with updated descriptions and identical homology. These "Additional Accessions" are not included in the sequence listing.

Transcripts that represent differentially expressed genes may be identified by utilizing a variety of methods known to those of skill in the art, including differential screening, subtractive hybridization, differential display, or hybridization to an array comprising a plurality of gene sequences.

"Differential expression" as used herein refers to both quantitative as well as qualitative differences in the genes' temporal and/or tissue expression patterns. Thus, a differentially expressed gene may have its expression activated or inactivated in normal versus neuronal disease conditions, or in control versus experimental conditions. Such a qualitatively regulated gene will exhibit an expression pattern within a given tissue or cell type that is detectable in either control or tumor samples, but is not detectable in both. Detectable, as used herein, refers to an RNA expression pattern that is detectable via the standard techniques of differential display, reverse transcription-(RT-)PCR and/or Northern analyses, which are well known to those of skill in the art. Generally, differential expression means that there is at least a 20% change, and in other instances at least a 2-, 3-, 5- or 10-fold difference between disease and control tissue expression. The difference usually is one that is statistically significant, meaning that the probability of the difference occurring by chance (the P-value) is less than some predetermined level (e.g., 5%). Usually the confidence level (P value) is <0.05, more typically <0.01, and in other instances, <0.001.

Alternatively, a differentially expressed gene may have its expression modulated, i.e., quantitatively increased or decreased, in normal versus neuronal disease states, or under control versus experimental conditions. The difference in expression need only be large enough to be visualized via standard detection techniques as described above. Generally the difference in expression levels, measured by either the presence of mRNA or the protein product, will differ from basal levels (i.e. normal tissue) by at least about 2 fold, usually at least about 5 fold, and may be 10 fold, 100 fold, or more.

Identification of $T_{BT}$ pathway genes may be performed through physical association of gene products, or through database identification of known physiologic pathways. Among the methods for detection protein—protein association are co-immunoprecipitation, crosslinking and co-purification through gradients or chromatographic columns. The two-hybrid system detects the association of proteins in vivo, as described by Chien et al. (1991) Proc. Natl. Acad. Sci. USA 88:9578–9582. The two-hybrid system or related methodology may be used to screen activation domain libraries for proteins that interact with a known "bait" gene protein.

Once a sequence has been identified as differentially expressed, the sequence can be subjected to a functional validation process to determine whether the gene plays a role in tumor initiation, progression or maintenance. Such candidate genes can potentially be correlated with a wide variety of cellular states or activities. The term "functional validation" as used herein refers to a process whereby one determines whether modulation of expression or function of a candidate gene or set of such genes causes a detectable change in a cellular activity or cellular state for a reference cell, which cell can be a population of cells such as a tissue or an entire organism. The detectable change or alteration that is detected can be any activity carried out by the reference cell. Specific examples of activities or states in which alterations can be detected include, but are not limited to, phenotypic changes (e.g., cell morphology, cell proliferation, cell viability and cell death); cells acquiring resistance to a prior sensitivity or acquiring a sensitivity which previously did not exist; protein/protein interactions; cell movement; intracellular or intercellular signaling; cell/cell interactions; cell activation (e.g., T cell activation, B cell activation, mast cell degranulation); release of cellular components (e.g., hormones, chemokines and the like); and metabolic or catabolic reactions.

A variety of options are available for functionally validating candidate genes. Such methods as RNAi technology can be used. Antisense technology can also be utilized to functionally validate a candidate gene. In this approach, an antisense polynucleotide that specifically hybridizes to a segment of the coding sequence for the candidate gene is administered to inhibit expression of the candidate gene in those cells into which it is introduced. The functional role that a candidate gene plays in a cell can also be assessed using gene "knockout" approaches in which the candidate gene is deleted, modified, or inhibited on either a single or both alleles. The cells or animals can be optionally be reconstituted with a wild-type candidate gene as part of a further analysis.

In one embodiment of the invention, RNAi technology is used in functional validation. As used herein, RNAi technology refers to a process in which double-stranded RNA is introduced into cells expressing a candidate gene to inhibit expression of the candidate gene, i.e., to "silence" its expression. The dsRNA is selected to have substantial identity with the candidate gene. In general such methods initially involve transcribing a nucleic acids containing all or part of a candidate gene into single- or double-stranded RNA. Sense and anti-sense RNA strands are allowed to anneal under appropriate conditions to form dsRNA. The resulting dsRNA is introduced into reference cells via various methods and the degree of attenuation in expression of the candidate gene is measured using various techniques. Usually one detects whether inhibition alters a cellular state or cellular activity. The dsRNA is prepared to be substantially identical to at least a segment of a candidate gene. Because only substantial sequence similarity between the candidate gene and the dsRNA is necessary, sequence variations between these two species arising from genetic mutations, evolutionary divergence and polymorphisms can be tolerated. Moreover, the dsRNA can include various modified or nucleotide analogs. Usually the dsRNA consists of two separate complementary RNA strands. However, in some instances, the dsRNA may be formed by a single strand of RNA that is self-complementary, such that the strand loops back upon itself to form a hairpin loop. Regardless of form, RNA duplex formation can occur inside or outside of a cell.

A number of options are available to detect interference of candidate gene expression (i.e., to detect candidate gene silencing). In general, inhibition in expression is detected by detecting a decrease in the level of the protein encoded by the candidate gene, determining the level of mRNA transcribed from the gene and/or detecting a change in phenotype associated with candidate gene expression.

TBT Genes and Polypeptides

Neuroligin2 is a neuronal cell surface protein that is enriched in synaptic plasma membranes and acts as a splice site-specific ligand for beta-neurexins, to form asymmetric intercellular junctions. The extracellular sequence of neuroligin 1 is composed of a catalytically inactive esterase domain homologous to acetylcholinesterase. Neuroligin 1 is known to colocalize with glutamatergic but not gamma-aminobutyric acid (GABA) ergic synapses. Thus neuroligin 1 is a synaptic cell-adhesion molecule that is enriched in postsynaptic densities where it may recruit receptors, channels, and signal-transduction molecules to synaptic sites of cell adhesion. The neuroligin/beta-neurexin junction may be involved in the specification of excitatory synapses.

Neuroligin-1 and -2 can trigger the de novo formation of presynaptic structure, suggesting that neuroligins are part of the machinery employed during the formation and remodeling of CNS synapses. Northern blot analysis shows that Neuroligin2 maps to the rat brain. The sequence and function of the protein in synapses may be found in, for example, Ichtchenko et al. (1995) *Cell* 81(3):435–43; Ichtchenko et al. (1996) *J Biol. Chem.* 271(5):2676–82; Song et al. (1999) *Proc Natl Acad Sci USA.* 96(3):1100–5; Nguyen (1997) *J Biol. Chem.* 272(41):26032–9; and Scheiffele et al. (2000) *Cell* 101(6):657–69.

Alpha-Catenin is an integral component of cell—cell contact sites. These contacts are highly dynamic and regulate morphogenesis, tissue remodeling, cell adhesion and motility. Among the hallmarks of cancer are defective cell—cell and cell-matrix adhesion. Alpha-catenin is homologous to the actin binding protein vinculin. Alpha-catenin has many binding partners, including PTPzeta. Alterations in alpha-catenin containing complexes may have a major contributing role in cell-adhesion defects in carcinomas arising in many different tissues. See, for example, Furukawa et al. (1994) *Cytogenet. Cell Genet.* 65:74–78; Herrenknecht et al. (1991) *Proc. Nat. Acad. Sci.* 88:9156–9160; Hirano et al. (1992) *Cell* 70:293–301; and Shimoyama et al. (1992) *Cancer Res.* 52:5770–5774. Cadherin-mediated cell—cell adhesion is known to be affected by the cytoplasmic proteins: alpha-, beta- and gamma-catenin. These catenins are believed to work as connectors that anchor E-cadherin to the cytoskeletal actin bundle, through the cadherin cytoplasmic domain. Dysfunction of this adhesion complex causes dissociation of cancer cells from primary tumor nodules, thus contributing to cancer invasion and metastasis. It has been shown that the human lung cancer cell line, PC9, which expresses E-cadherin but only a small quantity of abnormal-sized alpha-catenin, can grow as isolated cells but regains its cell—cell adhesion potential when transfected with alpha-catenin. Studies of the cadherin-catenin complex in retinoblastoma and normal retina tissues have shown N-cadherin is associated with alpha- and beta-catenin but not with E- or P-cadherin. Retinoblastoma cells, in contrast with normal retinal cells, express an N-cadherin/catenin complex that is irregularly distributed and weakly linked to the cytoskeleton. In retinoblastoma, this complex acts as an invasion promoter.

MEKK4 is a component of a sequential kinase cascade that is activated in response to a variety of extracellular signals. MEKK4 mRNA is widely expressed and encodes a protein of approximately 180 kDa. MEKK4 is localized in a perinuclear, vesicular compartment. MEKK4 binds to Cdc42 and Rac and stimulates the JNK pathway. MEKK family members are characterized as localized sensors that control cell responses at the level of gene expression, metabolism and the cytoskeleton. Analysis of the apoptotic pathway induced by growth factor withdrawal has demonstrated that BRCA1 can enhance signals via H-Ras, MEKK4, JNK, Fas ligand/Fas interactions, and caspase-9 activation, see Thangaraju et al. (2000) *J Biol Chem* 275 (43):33487–96.

PRKCL, 1 also known as PKN, is a serine/threonine protein kinase that has a catalytic domain highly homologous to protein kinase C in the carboxyl-terminal region and a unique regulatory domain in the amino-terminal region. The kinase activity can be abolished by a mutation in the predicted ATP binding site. PKN translocates from the cytosol to the nucleus upon stimulation and is cleaved during apoptosis, an event that generates a constitutively active kinase fragment (55 kDa cleavage product). PKN is ubiquitously expressed and is activated by fatty acids and is part of a signaling network that controls cell responses at the level of gene expression, metabolism and cytoskeleton. PKN maps to the same region of the mouse chromosome as myodystrophy mutation. It is ubiquitously expressed in human tissues.

Cathepsin O (also known as Cathepsin K) is a human cysteine protease and belongs to peptidase family C1. It is closely involved in osteoclast bone resorption and may participate in bone remodelling. The gene is composed of eight coding exons and seven introns and spans more than 30 kb. The number and distribution of exons and introns differs from other cathepsins and its chromosomal location (4q31–q32) is unique from othe cysteine proteases. Cathepsin O is highly expressed in osteocalasts and is transcriptionally regulated. Cathepsin O is further distinguished by its potent collagenolytic activity against Collagen I, suggesting a role for this protein in extracellular matrix destruction/remodeling. Cathepsin O has broad proteolytic activity. See Shi et al. (1995) *FEBS Lett* 357(2):129–34; and Inaoka et al. (1995) *Biochem Biophys Res Commun* 206(1):89–96.

EDG receptor is a high affinity receptor for lysophosphatidic acid and plays a role in biologically important processes including proliferation, morphological changes, and angiogenesis. EDG is a seven-transmembrane domain receptor. This receptor can couple to all but the Gs types and is linked to the mitogen activated kinase cascade. The expression of the EDG receptor is regulated and restricted.

The Edg transcript is induced in differentiating human endothelial cells and sphingosine-1-phosphate as a ligand for the G protein-coupled receptor EDG-1. This gene encodes a member of family I of the G protein-coupled receptors, as well as the EDG family of proteins. This protein functions as a lysophosphatidic acid (LPA) receptor and contributes to Ca2+ mobilization, a critical cellular response to LPA in cells, through association with Gi and Gq proteins. See An et al. (1998) *J. Biol. Chem.* 273 (14), 7906–7910.

Contactin 1 is a GPI anchored membrane protein involved in cell-adhesion and morphogenesis. It belongs to the immunoglobulin superfamily of proteins and contains 6 immunoglobulin like c2-type domains and 4 fibronectin type III-like domains. Contactin displays both homophilic and heterophilic binding activities and participates in bidirectional exchange of information between neurons and glial cells. The cell-contact dependent interactions involve several proteins. It is known to bind the carbonic anhydrase domain of PTPzeta. These interactions may lead to initiation of bidirectional signals that regulate cell migration and morphologic changes. It is highly expressed in the brain, spleen, muscle, kidney and lungs. See Berglund and Ranscht (1994) *Genomics* 21 (3), 571–582; and Reid and Hemperly (1994) *Brain Res.* 21:1–8.

OCT1 translocates hydrophobic and hydrophilic organic cations of different structures, and may be important for drug elimination. The OCT transporters belong to a superfamily that includes multi-drug resistance proteins, facilitative diffusion systems, and proton antiporters. OCT1 is not homologous to any other known protein and is found in kidney, liver and intestine. It is also expressed in cerebellar granule cells, medial habenula, medial mammillary cells and area postrema. The human OCT1 gene is an octamer binding transcription factor containing a POU domain with one homeobox containing domain. It consists of 7 exons and 6 introns, and is alternatively spliced. OCT1 is thought to potentiate CREB-dependent cyclin D1 transcriptional activity independent of Ser 133 phosphorylation and E1A-sensitive coactivator function and offers a new paradigm for the regulation of cyclin D1 induction by proliferative signals. OCT1 is differentially phosphorylated during progression through the cell cycle. See Roberts et al. (1991) *Science* 253(5023):1022–6; and Sturm et al. (1988) *Genes Dev* 2(12A): 1582–99.

Reticulocalbin2 is a ubiqiutously expressed calcium binding protein. It can regulate calcium-dependent activities in the endoplasmic reticulum lumen or post-ER compartment. This protein has four functional calcium-binding sites; potential sites II and VI have lost affinity for calcium. It belongs to the CREC family and contains 6 EF-hand calcium-binding domains. Elevated levels of expression of reticulocalbin are found in lens epithelial cells after oxidative stress. Human reticulocalbin localizes to a region on chromosome 11 (11p13). The gene is hemizygously deleted in individuals with the Wilms tumor, aniridia, genitourinary anomalies, mental retardation (WAGR) syndrome. See Carper et al. (2001) *Free Radic Biol Med.* 31(1):90–7; and Vorum et al. (2000) *FEBS Lett.* 465(2–3):129–34.

Protocadherin gamma B2. Protocadherins constitute a large family belonging to the cadherin superfamily. Protocadherins have unique features that are not found in classic cadherins. Expression of protocadherins is spatiotemporally regulated and they are localized at synapses in the CNS. Although protocadherins have Ca(2+)-dependent homophilic interaction activity, the activities are relatively weak. Some protocadherins have heterophilic interaction activity and the cytoplasmic domains associate with the unique cytoplasmic proteins, which are essential for their biological functions. Given the characteristic properties, the large size, and the diversity of members of the protocadherin family, protocadherins may participate in various biological processes. In particular, protocadherins play a central role in the CNS, as related to synaptic function. Since protocadherin expression correlate with synaptogenesis, changes in PDCH expression may reflect disturbed synaptogenesis. The gene maps to 5q31, where several neurological disorders map. See Suzuki (2000) *Exp Cell Res.* 261(1):13–8; and Hilschmann et al. (2001) *Naturwissenschaften* 88(1):2–12.

MOAT-B. This is a ubiquitously expressed organic anion pump that belongs to the ABC family of transporters. It is relevant to cellular detoxification and localizes to the integral membrane. MOAT-B is widely expressed with high levels in prostrate and low levels in the liver. It is closely related to MRP and cMOAT and yeast organic anion transporter YCF1. It is distinguished by the absence of 200 aa hydrophobic extension absent at the N-terminus and predicted to encode several transmembrane spanning regions. See Kool et al. (1997) *Cancer Res.* 57: 3537–3547; and Lee et al. (1998) *Cancer Res.* 58: 2741–2747.

RACK-1 is a guanine nucleotide binding protein that acts as an intracellular receptor that binds and anchors activated PKC to the cytoskeleton. It contains 7WD repeats and is widely expressed in many tissues. RACK interacts with Src tyrosine kinase and inhibits Src activity and cell growth. PKC activation induces RACK1 and Src co-localization and tyrosine phosphorylation of RACK. RACK1 is an important Src substrate that signals downstream of growth factor receptor tyrosine kinases and is thus involved in the regulation of Src function and cell growth. RACK1 may also be involved in angiogenesis. See Ron et al. (1994) *Proc Natl Acad Sci USA* 91(3):839–43; and Int J Cancer 2002 Nov. 10; 102(2):129–36.

Kangai-1. Expression of this gene is reduced in human cell lines derived from metastatic prostate tumors. KAI1 specifies a protein of 267 amino acids, with 4 transmembrane domains and 1 large extracellular hydrophilic domain with 3 potential N-glycosylation sites. KAI1 is evolutionarily conserved, is expressed in many human tissues, and encodes a member of a structurally distinct family of leukocyte surface glycoproteins. Sequence comparisons showed that KAI1 is likely to be the human homolog of the mouse leukocyte surface antigen R2. It also appears to be upregulated in activated T cells. The expression of the KAI1 gene is also downregulated during tumor progression of prostate, breast, lung, bladder, and pancreatic cancers in humans, and this downregulation appears to be at the level of transcription or posttranscription. The tumor suppressor gene p53 can directly activate the KAI1 gene by interacting with the 5-prime upstream region. See Dong et al. (1995) *Science* 268: 884–886; and Miyazaki et al. (2000) *Cancer* 89:955–962.

PTK9 is a protein tyrosine kinase that is divergent from other protein tyrosine kinases, as it lacks any of the known motifs observed in the catalytic domain of protein tyrosine kinases. The gene maps to 20q13. It is expressed at high levels in the bone marrow, spleen, brain, heart, liver, prostrate, kidney and lung.

CDAABP0138 is a protein tyrosine kinase isolated from patient with acute lymphoblastic leukemia. It may regulate pattern formation of hindbrain segmentation and has approximately 53% homology to mouse Csk kinase. This protein lacks the N-myristylation and autophosphorylation sites present in related src kinases.

Nucleic Acids

The sequences of $T_{BT}$ genes find use in diagnostic and therapeutic methods, for the recombinant production of the encoded polypeptide, and the like. The nucleic acids of the invention include nucleic acids having a high degree of sequence similarity or sequence identity to one of the sequences provided in Table 1. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to one of the sequences provided in Table 1 under stringent hybridization conditions. Further specific guidance regarding the preparation of nucleic acids is provided by Fleury et al. (1997) Nature Genetics 15:269–272; Tartaglia et al., PCT Publication No. WO 96/05861; and Chen et al., PCT Publication No. WO 00/06087, each of which is incorporated herein in its entirety.

The genes listed in Table 1 may be obtained using various methods well known to those skilled in the art, including but not limited to the use of appropriate probes to detect the genes within an appropriate cDNA or genomic DNA library, antibody screening of expression libraries to detect cloned DNA fragments with shared structural features, direct chemical synthesis, and amplification protocols. Libraries are preferably prepared from glioblastoma versus normal cells. Cloning methods are described in Berger and Kimmel, Guide to Molecular Cloning Techniques, Methods in Enzymology, 152, Academic Press, Inc. San Diego, Calif.; Sambrook, et al. (1989) Molecular Cloning—A Laboratory Manual (2nd ed) Vols. 1–3, Cold Spring Harbor Laboratory, Cold Spring Harbor Press, NY; and Current Protocols (1994), a joint venture between Greene Publishing Associates, Inc. and John Wiley and Sons, Inc.

The sequence obtained from clones containing partial coding sequences or non-coding sequences can be used to obtain the entire coding region by using the RACE method (Chenchik et al. (1995) CLONTECHniques (X) 1: 5–8). Oligonucleotides can be designed based on the sequence obtained from the partial clone that can amplify a reverse transcribed mRNA encoding the entire coding sequence. Alternatively, probes can be used to screen cDNA libraries prepared from an appropriate cell or cell line in which the gene is transcribed. Once the target nucleic acid is identified, it can be isolated and cloned using well-known amplification techniques. Such techniques include, the polymerase chain reaction (PCR) the ligase chain reaction (LCR), Qβ-replicase amplification, the self-sustained sequence replication system (SSR) and the transcription based amplification system (TAS). Such methods include, those described, for example, in U.S. Pat. No. 4,683,202 to Mullis et al.; PCR Protocols A Guide to Methods and Applications (Innis et al. eds) Academic Press Inc. San Diego, Calif. (1990); Kwoh et al. (1989) Proc. Natl. Acad. Sci. USA 86: 1173; Guatelli et al. (1990) Proc. Natl. Acad. Sci. USA 87: 1874; Lomell et al. (1989) J. Clin. Chem. 35: 1826; Landegren et al. (1988) Science 241: 1077–1080; Van Brunt (1990) Biotechnology 8: 291–294; Wu and Wallace (1989) Gene 4: 560; and Barringer et al. (1990) Gene 89: 117.

As an alternative to cloning a nucleic acid, a suitable nucleic acid can be chemically synthesized. Direct chemical synthesis methods include, for example, the phosphotriester method of Narang et al. (1979) Meth. Enzymol. 68: 90–99; the phosphodiester method of Brown et al. (1979) Meth. Enzymol: 68: 109–151; the diethylphosphoramidite method of Beau cage et al. (1981) Tetra. Lett., 22: 1859–1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids can be cDNAs or genomic DNAs, as well as fragments thereof. The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA flanking the coding region, either 3' or 5', or internal regulatory sequences as sometimes found in introns, contains sequences required for proper tissue, stage-specific, or disease-state specific expression, and are useful for investigating the up-regulation of expression in tumor cells.

Probes specific to the nucleic acid of the invention can be generated using the nucleic acid sequence disclosed in Table 1. The probes are preferably at least about 18 nt, 25 nt, 50 nt or more of the corresponding contiguous sequence of one of the sequences provided in Table 1, and are usually less than about 2, 1, or 0.5 kb in length. Preferably, probes are designed based on a contiguous sequence that remains unmasked following application of a masking program for masking low complexity. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Polypeptides

Polypeptides encoded by $T_{BT}$ genes are of interest for screening methods, as reagents to raise antibodies, as therapeutics, and the like. Such polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the polypeptide encoded by an ischemia associated gene, as provided in Table 1.

The polypeptides may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Typically, the coding sequence is placed under the control of a promoter that is functional in the desired host cell to produce relatively large quantities of the gene product. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, *E. coli*, other bacterial hosts, yeast, and various higher eukaryotic cells such as the COS, CHO and HeLa cells lines and myeloma cell lines.

In mammalian host cells, a number of viral-based expression systems may be used, including retrovirus, lentivirus, adenovirus, adeno-associated virus, and the like. In cases where an adenovirus is used as an expression vector, the coding sequence of interest can be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts.

Specific initiation signals may also be required for efficient translation of the genes. These signals include the ATG initiation codon and adjacent sequences. In cases where a complete gene, including its own initiation codon and adjacent sequences, is inserted into the appropriate expression vector, no additional translational control signals may be needed. However, in cases where only a portion of the gene coding sequence is inserted, exogenous translational control signals must be provided. These exogenous translational control signals and initiation codons can be of a variety of origins, both natural and synthetic. The efficiency of expression may be enhanced by the inclusion of appropriate transcription enhancer elements, transcription terminators, etc.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines that stably express the differentially expressed or pathway gene protein may be engineered. Rather than using expression vectors that contain viral origins of replication, host cells can be transformed with DNA controlled by appropriate expression control elements, and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the target protein. Such engineered cell lines may be particularly useful in screening and evaluation of compounds that affect the endogenous activity of the $T_{BT}$ protein. A number of selection systems may be used, including but not limited to the herpes simplex virus thymidine kinase, hypoxanthine-guanine phosphoribosyltransferase, and adenine phosphoribosyltransferase genes. Antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The polypeptide may be labeled, either directly or indirectly. Any of a variety of suitable labeling systems may be used, including but not limited to, radioisotopes such as $^{125}$I; enzyme labeling systems that generate a detectable calorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

As an option to recombinant methods, polypeptides and oligopeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of a $T_{BT}$ protein can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993).

For various purposes, for example as an immunogen, the entire $T_{BT}$ polypeptide or a fragment derived therefrom may be used. Preferably, one or more 8–30 amino acid peptide portions, e.g. of an extracellular domain may be utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred.

Specific Binding Members

The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. For the purposes of the present invention, the two binding members may be known to associate with each other, for example where an assay is directed at detecting compounds that interfere with the association of a known binding pair. Alternatively, candidate compounds suspected of being a binding partner to a compound of interest may be used.

Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; lipid and lipid-binding protein; etc. The specific binding pairs may include analogs, derivatives and fragments of the original specific binding member. For example, a receptor and ligand pair may include peptide fragments, chemically synthesized peptidomimetics, labeled protein, derivatized protein, etc.

In a preferred embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

Antibodies that bind specifically to one of the brain tumor protein targets are referred to as $\alpha$ (TBT). The specific or selective fit of a given structure and its specific epitope is sometimes referred to as a "lock and key" fit. The archetypal antibody molecule is the immunoglobulin, and all types of immunoglobulins, IgG, e.g. IgG1, IgG2a, IgG2b, IgG3, IgG4, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a TBT antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the brain tumor protein target, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristane, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Preferably, recombinant antibodies are produced in a recombinant protein production system that correctly glycosylates and processes the immunoglobulin chains, such as insect or mammalian cells. An advantage to using insect cells, which utilize recombinant baculoviruses for the production of antibodies, is that the baculovirus system allows production of mutant antibodies much more rapidly than stably transfected mammalian cell lines. In addition, insect cells have been shown to correctly process and glycosylate eukaryotic proteins, which prokaryotic cells do not. Finally, the baculovirus expression of foreign protein has been shown to constitute as much as 50–75% of the total cellular protein late in viral infection, making this system an excellent means of producing milligram quantities of the recombinant antibodies.

Antibodies with a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. Even through the brain is relatively isolated behind the blood brain barrier, an immune response still can occur in the form of increased leukocyte infiltration, and inflammation. Although some increased immune response against the tumor is desirable, the concurrent binding and inactivation of the therapeutic or imaging agent generally outweighs this benefit. Thus, humanized, single chain, chimeric, or human antibodies, which produce less of an immune response when administered to humans, are preferred for use in the present invention. Also included in the invention are multi-domain antibodies, and anti-idiotypic antibodies that "mimic" TBT. For example, antibodies that bind to a TBT domain and competitively inhibit the binding of TBT to its ligand may be used to generate anti-idiotypes that "mimic" TBT and, therefore, bind, activate, or neutralize a TBT, TBT ligand, TBT receptor, or TBT ligand. Such anti-idiotypic antibodies or Fab fragments of such anti-idiotypes can be used in therapeutic regimens involving a TBT mediated pathway (see, for example, Greenspan and Bona (1993) *FASEB J* 7(5):437–444; Nissinoff (1991) *J. Immunol.* 147(8):2429–2438.

A chimeric antibody is a molecule in which different portions are derived from different animal species, for example those having a variable region derived from a murine mAb and a human immunoglobulin constant region. Techniques for the development of chimeric antibodies are described in the literature. See, for example, Morrison et al. (1984) *Proc. Natl. Acad. Sci.* 81:6851–6855; Neuberger et al. (1984) *Nature* 312:604–608; Takeda et al. (1985) *Nature* 314:452–454. Single chain antibodies are formed by linking the heavy and light chain fragments of the Fv region via an amino acid bridge, resulting in a single chain polypeptide. See, for example, Huston et al., Science 242:423–426; Proc. Natl. Acad. Sci. 85:5879–5883; and Ward et al. *Nature* 341:544–546.

Antibody fragments that recognize specific epitopes may be generated by techniques well known in the field. These fragments include, without limitation, $F(ab')_2$ fragments, which can be produced by pepsin digestion of the antibody molecule, and Fab fragments, which can be generated by reducing the disulfide bridges of the $F(ab')_2$ fragments.

In one embodiment of the invention, a human or humanized antibody is provided, which specifically binds to the extracellular region of TBT with high affinity. Binding of the antibody to the extracellular region can lead to receptor down regulation or decreased biological activity, and decrease in cell proliferation, invasion and/or decrease in tumor size. Low affinity binders may also be useful for some immuno-therapies. See Lonberg et al. (1994) *Nature* 368:

856–859; and Lonberg and Huszar (1995) Internal Review of Immunology 13:65–93. In another aspect of the invention, a humanized antibody is provided that specifically binds to the extracellular region of TBT with high affinity, and which bears resemblance to the human antibody. These antibodies resemble human antibodies and thus can be administered to a human patient with minimal negative side effects.

Humanized antibodies are human forms of non-human antibodies. They are chimeras with a minimum sequence derived from of non-human Immunoglobulin. To overcome the intrinsic undesirable properties of murine monoclonal antibodies, recombinant murine antibodies engineered to incorporate regions of human antibodies, also called "humanized antibodies" are being developed. This alternative strategy was adopted as it is difficult to generate human antibodies directed to human antigens such as cell surface molecules. A humanized antibody contains complementarity determining region (CDR) regions and a few other amino acid of a murine antibody while the rest of the antibody is of human origin.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals that have been genetically altered to produce human immunoglobulins. Techniques for generating such animals, and deriving antibodies therefrom, are described in U.S. Pat. Nos. 6,162,963 and 6,150,584, incorporated fully herein by reference.

Alternatively, single chain antibodies (Fv, as described below) can be produced from phage libraries containing human variable regions. See U.S. Pat. No. 6,174,708. Intrathecal administration of single-chain immunotoxin, LMB-7 [B3(Fv)-PE38], has been shown to cure of carcinomatous meningitis in a rat model. *Proc Natl. Acad. Sci USA* 92, 2765–9, all of which are incorporated by reference fully herein.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879–5883 (1988) and Bird et al., Science 242:423–426 (1988), both fully incorporated herein, by reference. These are single chain Fvs which have been found to retain specificity and affinity and have been shown to be useful for imaging tumors and to make recombinant immunotoxins for tumor therapy. However, researchers have bound that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to an epitope of the brain tumor protein targets, although the term will encompass all immunoglobulins, derivatives, fragments, recombinant or engineered immunoglobulins, and modified immunoglobulins, as described above.

Candidate anti-TBT antibodies can be tested for by any suitable standard means, e.g. ELISA assays, etc. As a first screen, the antibodies may be tested for binding against the immunogen, or against the entire brain tumor protein target extracellular domain or protein. As a second screen, anti-TBT candidates may be tested for binding to an appropriate tumor cell line, or to primary tumor tissue samples. For these screens, the anti-TBT candidate antibody may be labeled for detection. After selective binding to the brain tumor protein target is established, the candidate antibody, or an antibody conjugate produced as described below, may be tested for appropriate activity (i.e., the ability to decrease tumor cell growth and/or to aid in visualizing tumor cells) in an in vivo model, such as an appropriate tumor cell line, or in a mouse or rat human brain tumor model, as described below. In a preferred embodiment, anti-TBT protein antibody compounds may be screened using a variety of methods in vitro and in vivo. These methods include, but are not limited to, methods that measure binding affinity to a target, biodistribution of the compound within an animal or cell, or compound mediated cytotoxicity. These and other screening methods known in the art provide information on the ability of a compound to bind to, modulate, or otherwise interact with the specified target and are a measure of the compound's efficacy.

Antibodies that alter the biological activity of TBT protein may be assayed in functional formats, such as glioblastoma cell culture or mouse/rat CNS tumor model studies. In glioblastoma cell models of activity, expression of the protein is first verified in the particular cell strain to be used. If necessary, the cell line may be stably transfected with a coding sequence of the protein under the control of an appropriate constituent promoter, in order to express the protein at a level comparable to that found in primary tumors. The ability of the glioblastoma cells to survive in the presence of the candidate function-altering anti-protein antibody is then determined. In addition to cell-survival assays, cell migration assays may be utilized to determine the effect of the candidate antibody therapeutic agent on the tumor-like behavior of the cells. Alternatively, if the brain tumor protein target is involved in angiogenesis, assays may be utilized to determine the ability of the candidate antibody therapeutic to inhibit vascular neogenesis, an important function in tumor biology.

The binding affinity of the TBT antibody may be determined using Biacore SPR technology, as is known in the art. In this method, a first molecule is coupled to a Dextran CM-5 sensor chip (Pharmacia), and the bound molecule is used to capture the antibody being tested. The antigen is then applied at a specific flow rate, and buffer applied at the same flow rate, so that dissociation occurs. The association rate and dissociation rates and corresponding rate constants are determined by using BIA evaluation software. For example, see Malmqvist (1993) Surface plasmon resonance for detection and measurement of antibody-antigen affinity and kinetics. Volume: 5:282–286; and Davies (1994) Nanobiology 3:5–16. Sequential introduction of antibodies permits epitope mapping. Once the antigen has been introduced, the ability of a second antibody to bind to the antigen can be tested. Each reactant can be monitored individually in the consecutive formation of multimolecular complexes, permitting multi-site binding experiments to be performed.

The binding of some ligands to their receptors can result in receptor-mediated internalization. This property may be desirable, e.g. with antibody therapeutics such as immunoliposomes; or undesirable, e.g. with antibody directed enzyme-prodrug therapy (ADEPT), where the enzyme needs to be present at the cell surface to convert non active prodrugs into active cytotoxic molecules.

Similarly, in vivo models for human brain tumors, particularly nude mice/SCID mice model or rat models, have been described, for example see Antunes et al. (2000). *J Histochem Cytochem* 48, 847–58; Price et al. (1999) *Clin Cancer Res* 5, 845–54; and Senner et al. (2000). *Acta Neuropathol* (Berl) 99, 603–8. Once correct expression of the protein in the tumor model is verified, the effect of the candidate anti-protein antibodies on the tumor masses in these models can be evaluated, wherein the ability of the anti-protein antibody candidates to alter protein activity is indicated by a decrease in tumor growth or a reduction in the tumor mass. Thus, antibodies that exhibit the appropriate anti-tumor effect may be selected without direct knowledge of the particular biomolecular role of the protein in oncogenesis. In vivo models may also be used to screen small molecule modulators of TBT function.

Arrays

Arrays provide a high throughput technique that can assay a large number of polynucleotides in a sample. In one aspect of the invention, an array is constructed comprising one or more of the TBT genes, proteins or antibodies, preferably comprising all of these sequences, which array may further comprise other sequences known to be up- or down-regulated in tumor cells. This technology can be used as a tool to test for differential expression. Arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614–9; Schena et al. (1995) *Science* 270(5235):467–70; Shalon et al. (1996) *Genome Res.* 6(7): 639–45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556, 752; WO 95/22058; and U.S. Pat. No. 5,631,734.

The probes utilized in the arrays can be of varying types and can include, for example, synthesized probes of relatively short length (e.g., a 20-mer or a 25-mer), cDNA (full length or fragments of gene), amplified DNA, fragments of DNA (generated by restriction enzymes, for example) and reverse transcribed DNA. Both custom and generic arrays can be utilized in detecting differential expression levels. Custom arrays can be prepared using probes that hybridize to particular preselected subsequences of mRNA gene sequences or amplification products prepared from them.

Arrays can be used to, for example, examine differential expression of genes and can be used to determine gene function. For example, arrays can be used to detect differential expression of $T_{BT}$ genes, where expression is compared between a test cell and control cell. Exemplary uses of arrays are further described in, for example, Pappalarado et al (1998) *Sem. Radiation Oncol.* 8:217; and Ramsay. (1998) *Nature Biotechnol.* 16:40. Furthermore, many variations on methods of detection using arrays are well within the skill in the art and within the scope of the present invention. For example, rather than immobilizing the probe to a solid support, the test sample can be immobilized on a solid support which is then contacted with the probe. Additional discussion regarding the use of microarrays in expression analysis can be found, for example, in Duggan, et al., Nature Genetics Supplement 21:10–14 (1999); Bowtell, Nature Genetics Supplement 21:25–32 (1999); Brown and Botstein, Nature Genetics Supplement 21:33–37 (1999); Cole et al., Nature Genetics Supplement 21:38–41 (1999); Debouck and Goodfellow, Nature Genetics Supplement 21:48–50 (1999); Bassett, Jr., et al., Nature Genetics Supplement 21:51–55 (1999); and Chakravarti, Nature Genetics Supplement 21:56–60 (1999).

For detecting expression levels, usually nucleic acids are obtained from a test sample, and either directly labeled, or reversed transcribed into labeled cDNA. The test sample containing the labeled nucleic acids is then contacted with the array. After allowing a period sufficient for any labeled nucleic acid present in the sample to hybridize to the probes, the array is typically subjected to one or more high stringency washes to remove unbound nucleic acids and to minimize nonspecific binding to the nucleic acid probes of the arrays. Binding of labeled sequences is detected using any of a variety of commercially available scanners and accompanying software programs.

For example, if the nucleic acids from the sample are labeled with fluorescent labels, hybridization intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stern et al. and are available from Affymetrix, Inc., under the GeneChip™ label. Some types of label provide a signal that can be amplified by enzymatic methods (see Broude, et al., *Proc. Natl. Acad. Sci. U.S.A.* 91, 3072–3076 (1994)). A variety of other labels are also suitable including, for example, radioisotopes, chromophores, magnetic particles and electron dense particles.

Those locations on the probe array that are hybridized to labeled nucleic acid are detected using a reader, such as described by U.S. Pat. No. 5,143,854, WO 90/15070, and U.S. Pat. No. 5,578,832. For customized arrays, the hybridization pattern can then be analyzed to determine the presence and/or relative amounts or absolute amounts of known mRNA species in samples being analyzed as described in e.g., WO 97/10365.

Diagnostic and Prognostic Methods

The differential expression of $T_{BT}$ genes and/or gene products in tumors indicates that these can serve as markers for diagnosis, for imaging, as well as for therapeutic applications. In general, such diagnostic methods involve detecting an elevated level of expression of $T_{BT}$ gene transcripts or gene products in the cells or tissue of an individual or a sample therefrom. A variety of different assays can be utilized to detect an increase in gene expression, including both methods that detect gene transcript and protein levels. More specifically, the diagnostic and prognostic methods disclosed herein involve obtaining a sample from an individual and determining at least qualitatively, and preferably quantitatively, the level of a $T_{BT}$ gene product expression in the sample. Usually this determined value or test value is compared against some type of reference or baseline value.

Nucleic acids or binding members such as antibodies that are specific for polypeptides derived from the sequence of one of the sequences provided in Table 1 are used to screen patient samples for increased expression of the corresponding mRNA or protein, or for the presence of amplified DNA in the cell. Samples can be obtained from a variety of sources. Samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from spinal fluid, or tumor biopsy samples. Also included in the term are derivatives and fractions of such cells and fluids. Samples can also be derived from in vitro cell cultures, including the growth medium, recombinant cells and cell components. Diagnostic samples are collected from an individual that has, or is suspected to have, a brain tumor. The presence of specific markers is useful in identifying and staging the tumor.

Nucleic Acid Screening Methods

Some of the diagnostic and prognostic methods that involve the detection of a TBT gene transcript begin with the lysis of cells and subsequent purification of nucleic acids from other cellular material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample.

A number of methods are available for analyzing nucleic acids for the presence of a specific sequence, e.g. upregulated or downregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2–14.33.

A detectable label may be included in an amplification reaction. Suitable labels include fluorochromes, e.g. ALEXA dyes (available from Molecular Probes, Inc.); fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes is then contacted with the cells and the probes allowed to hybridize. Excess probe is digested, washed away and the amount of hybridized probe measured. This approach is described in greater detail by Nucleic Acid Hybridization: A Practical Approach (Hames, et al., eds., 1987).

A variety of so-called "real time amplification" methods or "real time quantitative PCR" methods can also be utilized to determine the quantity of mRNA present in a sample. Such methods involve measuring the amount of amplification product formed during an amplification process. Fluorogenic nuclease assays are one specific example of a real time quantitation method that can be used to detect and quantitate transcripts. In general such assays continuously measure PCR product accumulation using a dual-labeled fluorogenic oligonucleotide probe—an approach frequently referred to in the literature simply as the "TaqMan" method. Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, each of which is incorporated by reference in its entirety.

Polypeptide Screening Methods

Screening for expression of the subject sequences may be based on the functional or antigenic characteristics of the protein. Various immunoassays designed to detect polymorphisms in proteins encoded by the sequences corresponding to the sequences provided in Table 1 may be used in screening. Detection may utilize staining of cells or histological sections, performed in accordance with conventional methods, using antibodies or other specific binding members that specifically bind to the TBT polypeptides. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and the polypeptide corresponding to a sequence of Table 1 in a lysate. Measuring the concentration of the target protein in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of the test protein is assayed in parallel with the samples or aliquots thereof to serve as controls. Preferably, each sample and standard will be added to multiple wells so that mean values can be obtained for each. The incubation time should be sufficient for binding. After incubation, the insoluble support is generally washed of non-bound components. After washing, a solution containing a second antibody is applied. The antibody will bind to one of the proteins of interest with sufficient specificity such that it can be distinguished from other components present. The second antibodies may be labeled to facilitate direct, or indirect quantification of binding. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the targeted polypeptide, conveniently using a labeling method as described for the sandwich assay.

In some cases, a competitive assay will be used. In addition to the patient sample, a competitor to the targeted protein is added to the reaction mix. The competitor and the target compete for binding to the specific binding partner. Usually, the competitor molecule will be labeled and detected as previously described, where the amount of competitor binding will be proportional to the amount of target protein present. The concentration of competitor molecule will be from about 10 times the maximum anticipated protein concentration to about equal concentration in order to make the most sensitive and linear range of detection.

Imaging In Vivo

In some embodiments, the methods are adapted for imaging use in vivo, e.g., to locate or identify sites where tumor cells are present. In these embodiments, a detectably-labeled moiety, e.g., an antibody, which is specific for the TBT polypeptide is administered to an individual (e.g., by injection), and labeled cells are located using standard imaging techniques, including, but not limited to, magnetic resonance imaging, computed tomography scanning, and the like.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized. A currently used method for labeling with $^{99m}$Tc is the reduction of pertechnetate ion in the presence of a chelating precursor to form the labile $^{99m}$Tc-precursor complex, which, in turn, reacts with the metal binding group of a bifunctionally modified chemotactic peptide to form a $^{99m}$Tc-chemotactic peptide conjugate.

The detectably labeled TBT specific antibody is used in conjunction with imaging techniques, in order to analyze the expression of the target. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body.

Among the most commonly used positron-emitting nuclides in PET are included $^{11}$C, $^{13}$N, $^{15}$O, and $^{18}$F. Isotopes that decay by electron capture and/or γ emission are used in SPECT, and include $^{123}$I and $^{99m}$Tc.

Therapeutic/Prophylactic Treatment Methods

Agents that modulate activity of $T_{BT}$ genes or proteins provide a point of therapeutic or prophylactic intervention, particularly agents that inhibit or upregulate activity of the polypeptide, or expression of the gene. Numerous agents are useful in modulating this activity, including agents that directly modulate expression, e.g. expression vectors, antisense specific for the targeted polypeptide; and agents that act on the protein, e.g. specific antibodies and analogs thereof, small organic molecules that block catalytic activity, etc.

Methods can be designed to selectively deliver nucleic acids to certain cells. Examples of such cells include, neurons, microglia, astrocytes, endothelial cells, oligodendrocytes, etc. Certain treatment methods are designed to selectively express an expression vector to neuron cells and/or target the nucleic acid for delivery to CNS derived cells. One technique for achieving selective expression in nerve cells is to operably link the coding sequence to a promoter that is primarily active in nerve cells. Examples of such promoters include, but are not limited to, prion protein promoter, calcium-calmodulin dependent protein kinase promoter. Alternatively, or in addition, the nucleic acid can be administered with an agent that targets the nucleic acid to CNS derived cells. For instance, the nucleic acid can be administered with an antibody that specifically binds to a cell-surface antigen on the nerve cells or a ligand for a receptor on neuronal cells.

When liposomes are utilized, substrates that bind to a cell-surface membrane protein associated with endocytosis can be attached to the liposome to target the liposome to nerve cells and to facilitate uptake. Examples of proteins that can be attached include capsid proteins or fragments thereof that bind to nerve cells, antibodies that specifically bind to cell-surface proteins on nerve cells that undergo internalization in cycling and proteins that target intracellular localizations within CNS derived cells, (see, e.g., Wu et al. (1987) J. Biol. Chem. 262:4429–4432; and Wagner, et al. (1990) Proc. Natl. Acad. Sci. USA 87:3410–3414). Gene marking and gene therapy protocols are reviewed by Anderson et al. (1992) Science 256:808–813. Various other delivery options can also be utilized. For instance, a nucleic acid containing a sequence of interest can be injected directly into the cerebrospinal fluid. Alternatively, such nucleic acids can be administered by intraventricular injections.

Antisense molecules can be used to down-regulate expression in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Compound Screening

Compound screening may be performed using an in vitro model, a genetically altered cell or animal, or purified protein corresponding to any one of the provided TBT genes. One can identify ligands or substrates that bind to, modulate or mimic the action of the encoded polypeptide.

The polypeptides include those encoded by $T_{BT}$ genes, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a polypeptide encoded by brain tumor associated genes, or a homolog thereof.

Transgenic animals or cells derived therefrom are also used in compound screening. Transgenic animals may be made through homologous recombination, where the normal locus corresponding to a $T_{BT}$ gene is altered. Alternatively, a nucleic acid construct is randomly integrated into the genome. Vectors for stable integration include plasmids, retroviruses and other animal viruses, YACs, and the like. A series of small deletions and/or substitutions may be made in the coding sequence to determine the role of different exons in enzymatic activity, oncogenesis, signal transduction, etc. Specific constructs of interest include antisense sequences that block expression of the targeted gene and expression of dominant negative mutations. A detectable marker, such as lac Z may be introduced into the locus of interest, where up-regulation of expression will result in an easily detected change in phenotype. One may also provide for expression of the target gene or variants thereof in cells or tissues where it is not normally expressed or at abnormal times of development. By providing expression of the target protein in cells in which it is not normally produced, one can induce changes in cell behavior.

Compound screening identifies agents that modulate function of the TBT polypeptides. Of particular interest are screening assays for agents that have a low toxicity for human cells. A wide variety of assays may be used for this purpose. Knowledge of the 3-dimensional structure of the encoded protein, derived from crystallization of purified recombinant protein, could lead to the rational design of small drugs that specifically inhibit activity. These drugs may be directed at specific domains.

Two commonly used markers of GPCR activation are intracellular calcium and cAMP. This method can also be used for the identification of functional agonists and antagonists for G-protein coupled receptors (GPCRs). FLIPR (Fluorometric Imaging Plate Reader Molecular Devices Corp) is used to monitor intracellular calcium mobilization. In order to monitor orphan GPCR activity orphan GPCR targets are force coupled to chimeric G-proteins. This enables the measurement of orphan GPCR's that stimulate either the Gq or Gs pathways to be probed in a single well. First, excitation of the Gq-PLC pathway resulting in calcium mobilization is measured in an intact cell utilizing a FLIPR instrument. Subsequently Gs-activation is monitored by lysing the cells and measuring the levels of cAMP using an HTRF method. This type of dual readout reduces reagent costs and compound consumption during ligand fishing screens.

The effect of an agent on an invasion assay may be monitored, for example, to provide a measure of the cells ability to move through a matrix like matrigel in response to a chemoattractant, e.g. 5% fetal bovine serum, etc. Percent Invasion is determined by the number of cells invading through matrigel coated FluoroBlok membrane divided by the number of cells invading through uncoated Fluorblok membrane.

A number of in vitro and in vivo bioassays have been developed to mimic the complex process of angiogenesis. Among these, two assays in particular have been widely used to screen specifically for angiogenic regulatory factors, each mimicking an aspect of angiogenesis; namely, endothelial cell proliferation and migration. The proliferation assay uses cultured capillary endothelial cells and measures either increased cell number or the incorporation of radiolabeled or modified nucleosides to detect cells in S phase. In contrast, the chemotaxis assay separates endothelial cells and a test solution by a porous membrane disc (a Boyden Chamber), such that migration of endothelial cells across the barrier is indicative of a chemoattractant present in the test solution.

Rate of internalization can be measured by coupling a fluorescent tag to the protein for example using the Cellomics Array Scan HCS reader. Rate of association and dissociation can also be measured in a similar fashion. Receptor internalization can be measured by its accumulation in the recycling compartment, and the receptor's decrease in the recycling compartment.

The ability of an agent to affect apoptosis may be determined. Apoptosis can be defined as "gene-directed cellular self-destruction". Cell death can occur by necrosis or apoptosis. There are many ways to measure apoptosis. For example, loss of cell viability, determined by failure to exclude vital dye, or uptake of MTT; DNA fragmentation, in situ tunnel labeling, cell and nuclear morphology, sub G1 peak FACS analysis, cysteine protease activation, inhibition of Bcl2 etc.

Gelatin zymography is a qualitative method to analyze enzymes involved in matrix degradation. It can be combined with fluorogenic substrate assays to demonstrate temporal changes in enzyme concentration and activity. The invasive property of a tumor may be accompanied by the elaboration of proteolytic enzymes, such as collagenases, that degrade matrix material and basement membrane material, to enable the tumor to expand beyond the confines of the particular tissue in which that tumor is located. Elaboration of such enzymes may be by endogenous synthesis within the tumor cells, or may be elicited from adjacent cells or by circulating neutrophils, in which cases the elicitation by the tumor results from chemical messengers elaborated by the tumor and expression of the enzymes occurs at the tumor site or proximal to the tumor.

The effect of an agent on signaling pathways may be determined using reporter assays that well known in the art. Binding by a ligand triggers activation of key cell signaling pathways, such as $p21^{ras}$, MAP kinases, NF-kappaB and cdc42/rac implicated in tumors. The cis reporting system can be used to determine if the gene or protein of interest acts on speciifc enhancer elements while the trans-activator indicates if the gene or protein of interest directly or indirectly may be involved in the phosphorylation and activation of the transcription factor.

The term "agent" as used herein describes any molecule, e.g. protein or pharmaceutical, with the capability of altering or mimicking the physiological function of a $T_{BT}$ polypeptide. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein—protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to a $T_{BT}$ polypeptide, as at least some of the compounds so identified are likely inhibitors. The binding assays usually involve contacting a $T_{BT}$ polypeptide with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61–89.

Certain screening methods involve screening for a compound that modulates the expression of a TBT gene. Such methods generally involve conducting cell-based assays in which test compounds are contacted with one or more cells expressing a $T_{BT}$ gene and then detecting and an increase in expression. Some assays are performed with tumor cells that express endogenous $T_{BT}$ genes. Other expression assays are conducted with non-neuronal cells that express an exogenous $T_{BT}$ gene.

The level of expression or activity can be compared to a baseline value. As indicated above, the baseline value can be a value for a control sample or a statistical value that is representative of expression levels for a control population. Expression levels can also be determined for cells that do not express $T_{BT}$ gene, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal that serves as a model for humans and then determining if $T_{BT}$ gene is in fact upregulated. The animal models utilized in validation studies generally are mammals. Specific examples of suitable animals include, but are not limited to, primates, mice, and rats.

Active test agents identified by the screening methods described herein that inhibit $T_{BT}$ polypeptide activity and/or tumor growth can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Antibody Conjugates

The anti-$T_{BT}$ antibodies for use in the present invention may have utility without conjugation when the native activity of the brain tumor protein target is altered in the tumor cell. Such antibodies, which may be selected as described above, may be utilized without as a therapeutic agent. In another embodiment of the invention, $T_{BT}$ specific antibodies, which may or may not alter the activity of the target polypeptide, are conjugated to cytotoxic or imaging agents, which add functionality to the antibody.

The anti-$T_{BT}$ antibodies can be coupled or conjugated to one or more therapeutic cytotoxic or imaging moieties. As used herein, "cytotoxic moiety" is a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. "Imaging moiety" (I) is a moiety that can be utilized to increase contrast between a tumor and the surrounding healthy tissue in a visualization technique (e.g., radiography, positron-emission tomography, magnetic resonance imaging, direct or indirect visual inspection). Thus, suitable imaging moieties include radiography moieties (e.g. heavy metals and radiation emitting moieties), positron emitting moieties, magnetic resonance contrast moieties, and optically visible moieties (e.g., fluorescent or visible-spectrum dyes, visible particles, etc.). It will be appreciated by one of ordinary skill that some overlap exists between therapeutic and imaging moieties. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques.

In general, therapeutic or imaging agents may be conjugated to the anti-TBT moiety by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the anti-TBT antibody moiety through a an oxidized carbohydrate group at a glycosylation site, as described in U.S. Pat. Nos. 5,057,313 and 5,156,840. Yet another alternative method of coupling the antibody moiety to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group that is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671, 958), and acid-catalyzed hydrolysis (e.g., U.S. Pat. No. 4,569,789).

Two or more cytotoxic and/or imaging moieties may be conjugated to an antibody, where the conjugated moieties are the same or different. By poly-derivatizing the anti-TBT antibody, several cytotoxic strategies can be simultaneously implemented; an antibody may be made useful as a contrasting agent for several visualization techniques; or a therapeutic antibody may be labeled for tracking by a visualization technique. Immunoconjugates with more than one moiety may be prepared in a variety of ways. For example, more than one moiety may be coupled directly to an antibody molecule, or linkers which provide multiple sites for attachment (e.g., dendrimers) can be used. Alternatively, a carrier with the capacity to hold more than one cytotoxic or imaging moiety can be used.

A carrier may bear the cytotoxic or imaging moiety in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699, 784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to anti-TBT antibody moieties for use in the invention, as a sufficient amount of the imaging moiety (dye, magnetic resonance contrast reagent, etc.) for detection may be more easily associated with the antibody moiety. In addition, encapsulation carriers are also useful in chemotoxic therapeutic embodiments, as they can allow the therapeutic compositions to gradually release a chemotoxic moiety over time while concentrating it in the vicinity of the tumor cells:

Carriers and linkers specific for radionuclide agents (both for use as cytotoxic moieties or positron-emission imaging moieties) include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionuclides that are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At may be conjugated to antibody moieties for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope may be utilized in the recited iodo-reagents. Radionuclides can be conjugated to anti-$T_{BT}$ antibody moieties by suitable chelation agents known to those of skill in the nuclear medicine arts.

Preferred chemotoxic agents include small-molecule drugs such as carboplatin, cisplatin, vincristine, taxanes such as paclitaxel and docetaxel, hydroxyurea, gemcitabine, vinorelbine, irinotecan, tirapazamine, matrilysin, methotrexate, pyrimidine and purine analogs, and other suitable small toxins known in the art. Preferred chemotoxin differentiation inducers include phorbol esters and butyric acid. Chemotoxic moieties may be directly conjugated to the anti-$T_{BT}$ antibody moiety via a chemical linker, or may encapsulated in a carrier, which is in turn coupled to the anti-$T_{BT}$ antibody moiety.

Chemotherapy is helpful in controlling high-grade gliomas. A common combination of chemotherapeutics is "PCV", which refers to the three drugs: Procarbazine, CCNU, and Vincristine. Temozolomide (Temodar) is approved by the FDA for treatment of anaplastic astrocytoma, and this drug is now widely used for high-grade gliomas. Neupogen may be administered to patients whose white blood counts fall to very low levels after chemotherapy.

Preferred toxin proteins for use as cytotoxic moieties include ricins A and B, abrin, diphtheria toxin, bryodin 1 and 2, momordin, trichokirin, cholera toxin, gelonin, *Pseudomonas* exotoxin, *Shigella* toxin, pokeweed antiviral protein, and other toxin proteins known in the medicinal biochemistry arts. The nontoxic ricin B chain is the moiety that binds to cells while the A chain is the toxic portion that inactivates protein synthesis—but only after delivery to the cytoplasm by the disulfide-linked B chain which binds to galactose-terminal membrane proteins. Abrin, diphtheria toxin, and *Pseudomonas* exotoxins all have similar 2-chain components; with one chain mediating cell membrane binding and entry and the toxic enzymatic A chain. Cholera has a pentameric binding subunit coupled to the toxic A chain. As these toxin agents may elicit undesirable immune responses in the patient, especially if injected intravascularly, it is preferred that they be encapsulated in a carrier for coupling to the anti-$T_{BT}$ antibody moiety.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions which may be utilized for x-ray radiography are described in U.S. Pat. No. 5,709,846, incorporated fully herein by reference. Such moieties may be conjugated to the anti-$T_{BT}$ antibody moiety through an acceptable chemical linker or chelation carrier. In addition, radionuclides which emit radiation capable of penetrating the scull may be useful for scintillation imaging techniques. Suitable radionuclides for conjugation include $^{99}Tc$, $^{111}In$, and $^{67}Ga$. Positron emitting moieties for use in the present invention include $^{18}F$, which can be easily conjugated by a fluorination reaction with the anti-TBT antibody moiety according to the method described in U.S. Pat. No. 6,187,284.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(II), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the anti-TBT antibody moieties through a suitable chemical linker.

Optically visible moieties for use as imaging moieties include fluorescent dyes, or visible-spectrum dyes, visible particles, and other visible labeling moieties. Fluorescent dyes such as ALEXA dyes, fluorescein, coumarin, rhodamine, bodipy Texas red, and cyanine dyes, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. In preferred embodiments, such dyes are encapsulated in carrier moieties, which are in turn conjugated to the anti-TBT antibody. Alternatively, visible particles, such as colloidal gold particles or latex particles, may be coupled to the anti-TBT antibody moiety via a suitable chemical linker.

Pharmaceutical Formulations

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic or imaging compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527–1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11, 74, 76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

One method for administration of the therapeutic compositions of the invention is by deposition into the inner cavity of a cystic tumor by any suitable technique, such as by direct injection (aided by stereotaxic positioning of an injection syringe, if necessary) or by placing the tip of an Ommaya reservoir into a cavity, or cyst, for administration. Where the tumor is a solid tumor, the antibody may be administered by first creating a resection cavity in the location of the tumor. This procedure differs from an ordinary craniotomy and tumor resection only in a few minor respects. As tumor resection is a common treatment procedure, and is often indicated to relieve pressure, administration of the therapeutic compositions of the invention can be performed following tumor resection. Following gross total resection in a standard neurosurgical fashion, the cavity is preferable rinsed with saline until all bleeding is stopped by cauterization. Next the pia-arachnoid membrane, surrounding the tumor cavity at the surface, is cauterized to enhance the formation of fibroblastic reaction and scarring in the pia-arachnoid area. The result is the formation of an enclosed, fluid-filled cavity within the brain tissue at the location from where the tumor was removed. After the cyst has been formed, either the tip of an Ommaya reservoir or a micro catheter, which is connected to a pump device and allows the continues infusion of an antibody solution into the cavity, can be placed into the cavity. See, e.g., U.S. Pat. No. 5,558,852, incorporated fully herein by reference.

Alternatively, a convection-enhanced delivery catheter may be implanted directly into the tumor mass, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 $\mu$l/minute), rather than diffusive flow, to deliver the therapeutic or imaging composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient to retard the growth and promote the death of tumor cells, or an effective amount of an imaging composition to administer to a patient to facilitate the visualization of a tumor. Dosage of the antibody-conjugate will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Imaging moieties are typically less toxic than cytotoxic moieties and may be administered in higher doses in some embodiments. Utilizing ordinary skill, the competent clinician will be able to optimize the dosage of a particular therapeutic or imaging composition in the course of routine clinical trials.

Typically the dosage will be 0.001 to 100 milligrams of conjugate per kilogram subject body weight. Doses in the range of 0.01 to 1 mg per kilogram of patient body weight may be utilized for a radionuclide therapeutic composition which is administered intrathecally. Relatively large doses, in the range of 0.1 to 10 mg per kilogram of patient body weight, may used for imaging conjugates with a relatively non-toxic imaging moiety. The amount utilized will depend on the sensitivity of the imaging method, and the relative toxicity of the imaging moiety. In a therapeutic example, for example where the therapeutic composition comprises a $^{131}$I cytotoxic moiety, the dosage to the patient will typically start at a lower range of 10 mCi, and go up to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. Similarly, chemotoxic or toxin protein doses may be scaled accordingly.

The compositions can be administered to the subject in a series of more than one administration. For therapeutic compositions, regular periodic administration (e.g., every 2–3 days) will sometimes be required, or may be desirable to reduce toxicity. For therapeutic compositions which will be utilized in repeated-dose regimens, antibody moieties which do not provoke immune responses are preferred. The imaging antibody conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

In addition to the use of imaging antibody conjugates for simple visualization, these compositions may be utilized as a "dry run" for more toxic cytotoxic antibody conjugates. If the same antibody moiety is utilized for the imaging conjugate as for the therapeutic conjugate, the physician may first use a visualization technique to determine precisely where in the brain the cytotoxic conjugate will concentrate. If a sufficient degree of tissue selectivity is not achieved (e.g., if the tumor cells are too disperse in the normal tissue, or if the particular brain tumor protein target chosen is not sufficiently overexpressed in the particular patient's tumor cells), then the physician may choose another brain tumor protein target. The provision of numerous brain tumor protein targets by the present invention, along with both imaging and therapeutic agents, allows a high degree of flexibility in designing an effective treatment regimen for the individual patient.

Combination Therapies

Brain tumors tend to be heterogeneous in character, and pervasive throughout the brain tissue. This combination often makes them difficult to treat. In some cases, it may be preferred to use various combinations of therapeutic or imaging agents, in order to more fully target all of the cells exhibiting tumorigenic characteristics. Such combination treatments may be by administering blended antibody therapeutic or imaging compositions, individually prepared as described above, and administering the blended therapeutic to the patient as described. The skilled administering physician will be able to take such factors as combined toxicity, and individual agent efficacy, into account when administering such combined agents. Additionally, those of skill in the art will be able to screen for potential cross-reaction with each other, in order to assure full efficacy of each agent.

Alternatively, several individual brain tumor protein target compositions may be administered simultaneously or in succession for a combined therapy. This may be desirable to avoid accumulated toxicity from several antibody conjugate reagents, or to more closely monitor potential adverse reactions to the individual antibody reagents. Thus, cycles such as where a first antibody therapeutic agent is administered on day one, followed by a second on day two, then a period with out administration, followed by re-administration of the antibody therapeutics on different successive days, is comprehended within the present invention.

Cancer Vaccines

The proteins identified in this invention can be used to elicit an immune response in an autologous, allogeneic and xenogeneic host. For example where a tumor cell specifically expresses the protein, or over-expresses the protein relative to normal cells, a cytolytic immune response may be induced, where the tumor cell is preferentially killed. The antigen for such purposes may be from the same or a different species. As used herein, the term antigen is intended to refer to a molecule capable of eliciting an immune response in a mammalian host, which may be a humoral immune response, i.e. characterized by the production of antigen-specific antibodies, or a cytotoxic immune response, i.e. characterized by the production of antigen specific cytotoxic T lymphocytes.

The portion of the antigen bound by the antibody or T cell receptor is referred to as an epitope. Antigens, particular complex antigens such as polypeptides, usually comprise multiple epitopes. Where the antigen is a protein, linear epitopes range from about 5 to 20 amino acids in length. Antibodies and T cell receptor may also recognize conformational determinants formed by non-contiguous residues on an antigen, and an epitope can therefore require a larger fragment of the antigen to be present for binding, e.g. a protein domain, or substantially all of a protein sequence. It will therefore be appreciated that a therapeutic protein, which may be several hundred amino acids in length, can comprise a number of distinct epitopes.

Several methods exist which can be used to induce an immune response against weakly antigenic protein, i.e. autologous proteins, etc. The immunogen is usually delivered in vivo to elicit a response, but in some cases it is advantageous to prime antigen presenting cells, e.g. dendritic cells, ex vivo prior to introducing them into the host animal.

In order to produce an immune response, the protein may be made as a fusion protein or otherwise conjugated to another polypeptide, and may be chemically modified or mixed with an adjuvant.

Examples of conjugates, which may utilize peptide linkage or other linkage to joint the molecules, include, for example KLH, pre-S HbsAg or cytokines or chemokines such as, for example interferon inducible protein 10 (IP-10), monocyte chemotactic protein 3 (MCP-3), interleukin-1, -2 and -8, granulocyte macrophage-colony stimulating factor (GM-CSF), etc, or may be chemically modified. Examples of suitable fusion chemokines and methods for antigen preparation and immunization are provided in Biragyn et al (Immunol Rev (1990) 170:115–126); Biragyn et al (Nature Biotechnology (1999) 17:253–258 and Tao et al Nature (1993) 362:755–695).

The polypeptide antigens may be mixed with an adjuvant that will augment specific immune reponses to the antigen. Many different types of adjuvants are known in the art and may include e.g. alum, stearyl tyrosine, saponin, monophosphoryl lipid A (MPL-A), muramyl tripeptide phosphatidylethanolamine (MTP-PE) etc. Adjuvants may also contain cytokines, such as interleukin 1 (IL1), interleukin 2 (IL2) other interleukins, TNFα, and γ-interferon, granulocyte macrophage-colony stimulating factor, tumor necrosis factor etc. Adjuvants may also contain other moieties such as cholera toxin B subunit, whole cell killed mycobacteria, *Bordetella pertussis* components, diptheria toxins and the like. Vaccine antigens may be presented using microspheres, liposomes, may be produced using an immunostimulating complex (ISCOM), as is known in the art.

Where an ex vivo antigen loading step is included, dendritic cells are isolated from an individual, using known methods, and incubated with the peptide antigen, preferably fused to a cytokine such as GM-CSF. The dendritic cell preparation may then be fractionated and administered to the host by intravenous or central injection according to established procedures (e.g., infusion over 30 to 60 minutes). The responsiveness of the subject to this treatment may be measured by monitoring the induction of a cytolytic T-cell response, a helper T-cell response and antibody response towards the antigen in peripheral blood mononuclear cells by methods well known in the art. The disclosures of U.S. Pat. Nos. 5,851,756, 6,080,409, 5,994,126 and 5, 972,334 are herein incorporated by reference in their entirety.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Identification of Differentially Expressed Sequences

Brain Tumors: Tumor tissue, confirmed as glioblastoma grade IV by neuropathology, from an unknown patient was snap frozen in the operation hall and served as experimental sample. Human whole brain tissue (Clontech Laboratories, Palo Alto, USA) served as control sample. Poly-A$^+$ RNA prepared from the cells was converted into double-stranded cDNA (dscDNA). Subtractive hybridization was carried out using the dscDNA from tumors with an excess of dscDNA prepared from the same region of a non-cancerous brain. Differentially expressed gene fragments were cloned into a plasmid vector, and the resulting library was transformed into *E. Coli* cells. Inserts of recombinant clones were amplified by the polymerase chain reaction (PCR). The PCR products (fragments of 200–2000 bp in size) were sequenced using an oligonucleotide complementary to common vector sequences. The resulting sequence information was compared to public databases using the BLAST (blastn) and Smith Waterman algorithm. The differentially expressed sequences thus identified are listed in Table 1.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

What is claimed is:

1. A method for the diagnosis or staging of a brain tumor, the method comprising:
   determining the upregulation or downregulation of expression of the sequence set forth in SEQ ID NO:8.

2. The method according to claim 1, wherein said brain tumor is an astrocytoma.

3. The method according to claim 2, wherein said astrocytoma is a glioblastoma.

4. The method according to claim 1, wherein said determining comprises detecting increased or decreased amounts of polypeptide in brain tumor cells.

5. A method of imaging a brain tumor, the method comprising:
   administering to a patient an effective amount of a compound comprising an antibody that specifically binds the polypeptide set forth in SEQ ID NO:8, wherein said compound antibody is conjugated to an imaging moiety; and
   visualizing the imaging moiety of said conjugate.

6. The method of claim 5 wherein said antibody is administered by intrathecal administration.

7. The method of claim 5 wherein said antibody is administered by intravascular administration.

8. The method of claim 5 wherein the brain tumor is an astrocytoma.

9. The method of claim 8, wherein said astrocytoma is a glioblastoma.

10. The method of claim 5, wherein said imaging moiety is selected from the group consisting of a radiographic moiety, a positron-emitting moiety, an optically visible dye, an optically visible particle, and a magnetic spin contrast moiety.

11. A method to treat a brain tumor, the method comprising:
    administering a therapeutic amount of an antibody that specifically binds a the polypeptide set forth in SEQ ID NO:8, wherein said antibody is conjugated to one or more cytotoxic moieties.

12. The method of claim 11 wherein said antibody is administered by intrathecal administration.

13. The method of claim 11 wherein said antibody is administered by intravascular administration.

14. The method of claim 11 wherein the brain tumor is an astrocytoma.

15. The method of claim 14, wherein said astrocytoma is a glioblastoma.

16. The method of claim 11, wherein said cytotoxic moiety is selected from the group consisting of a radioactive moiety, a chemotoxic moiety, and a toxin protein moiety.

17. A method for generating an immune response to a brain tumor, comprising:
    (a) administering to a host an immunogenic composition comprising the polypeptide set forth in SEQ ID NO:8;
    (b) monitoring the induction of an immune response.

18. The method of claim 17, wherein the host is suffering from a brain tumor.

19. The method of claim 17, wherein said administering step further comprises incubating isolated dendritic cells with the polypeptide.

20. A screening method for developing biologically active agents that inhibit or increase activity of a brain tumor protein target ($T_{BT}$) gene or gene product, the method comprising:
    combining a candidate biologically active agent with:
    a polypeptide encoded by the sequence set forth in SEQ ID NO:8; and
    determining the effect of said agent on brain tumor induced molecular and cellular changes.

* * * * *

SEQUENCE LISTING

```
<160> NUMBER OF SEQ ID NOS: 29

<210> SEQ ID NO 1
<211> LENGTH: 3774
<212> TYPE: DNA
<213> ORGANISM: Homo sapiens
<220> FEATURE:
<221> NAME/KEY: CDS
<222> LOCATION: (1505)..(2461)
<223> OTHER INFORMATION:
<220> FEATURE:
<221> NAME/KEY: misc_feature
<222> LOCATION: (71)..(71)
<223> OTHER INFORMATION: A, C, T or G
<220> FEATURE:
<221> NAME/KEY: misc_feature
<222> LOCATION: (74)..(74)
<223> OTHER INFORMATION: A, C, T or G
<220> FEATURE:
<221> NAME/KEY: misc_feature
<222> LOCATION: (123)..(123)
<223> OTHER INFORMATION: A, C, T or G
<220> FEATURE:
<221> NAME/KEY: misc_feature
<222> LOCATION: (124)..(126)
<223> OTHER INFORMATION: A, C, T or G
<220> FEATURE:
<221> NAME/KEY: misc_feature
<222> LOCATION: (129)..(132)
<223> OTHER INFORMATION: A, C, T or G
<220> FEATURE:
<221> NAME/KEY: misc_feature
<222> LOCATION: (135)..(138)
<223> OTHER INFORMATION: A, C, T or G
<220> FEATURE:
<221> NAME/KEY: misc_feature
<222> LOCATION: (145)..(145)
<223> OTHER INFORMATION: A, C, T or G
<220> FEATURE:
<221> NAME/KEY: misc_feature
<222> LOCATION: (159)..(159)
<223> OTHER INFORMATION: A, C, T or G
<220> FEATURE:
<221> NAME/KEY: misc_feature
<222> LOCATION: (163)..(163)
<223> OTHER INFORMATION: A, C, T or G
<220> FEATURE:
<221> NAME/KEY: misc_feature
<222> LOCATION: (720)..(720)
```

```
<223> OTHER INFORMATION: A, C, T or G
<220> FEATURE:
<221> NAME/KEY: misc_feature
<222> LOCATION: (1140)..(1140)
<223> OTHER INFORMATION: A, C, T or G
<220> FEATURE:
<221> NAME/KEY: misc_feature
<222> LOCATION: (1344)..(1344)
<223> OTHER INFORMATION: A, C, T or G
<220> FEATURE:
<221> NAME/KEY: misc_feature
<222> LOCATION: (1354)..(1354)
<223> OTHER INFORMATION: A, C, T or G
<220> FEATURE:
<221> NAME/KEY: misc_feature
<222> LOCATION: (1475)..(1475)
<223> OTHER INFORMATION: A, C, T or G
<220> FEATURE:
<221> NAME/KEY: misc_feature
<222> LOCATION: (1534)..(1534)
<223> OTHER INFORMATION: A, C, T or G
<220> FEATURE:
<221> NAME/KEY: misc_feature
<222> LOCATION: (1544)..(1544)
<223> OTHER INFORMATION: A, C, T or G
<220> FEATURE:
<221> NAME/KEY: misc_feature
<222> LOCATION: (1552)..(1552)
<223> OTHER INFORMATION: A, C, T or G
<220> FEATURE:
<221> NAME/KEY: misc_feature
<222> LOCATION: (1709)..(1709)
<223> OTHER INFORMATION: A, C, T or G
<220> FEATURE:
<221> NAME/KEY: misc_feature
<222> LOCATION: (1776)..(1780)
<223> OTHER INFORMATION: A, C, T or G
<220> FEATURE:
<221> NAME/KEY: misc_feature
<222> LOCATION: (1782)..(1783)
<223> OTHER INFORMATION: A, C, T or G
<220> FEATURE:
<221> NAME/KEY: misc_feature
<222> LOCATION: (1785)..(1788)
<223> OTHER INFORMATION: A, C, T or G
<220> FEATURE:
<221> NAME/KEY: misc_feature
<222> LOCATION: (1792)..(1792)
<223> OTHER INFORMATION: A, C, T or G
<220> FEATURE:
<221> NAME/KEY: misc_feature
<222> LOCATION: (1837)..(1837)
<223> OTHER INFORMATION: A, C, T or G
<220> FEATURE:
<221> NAME/KEY: misc_feature
<222> LOCATION: (1933)..(1933)
<223> OTHER INFORMATION: A, C, T or G
<220> FEATURE:
<221> NAME/KEY: misc_feature
<222> LOCATION: (2144)..(2148)
<223> OTHER INFORMATION: A, C, T or G
<220> FEATURE:
<221> NAME/KEY: misc_feature
<222> LOCATION: (2151)..(2151)
<223> OTHER INFORMATION: A, C, T or G
<220> FEATURE:
<221> NAME/KEY: misc_feature
<222> LOCATION: (2154)..(2161)
<223> OTHER INFORMATION: A, C, T or G
<220> FEATURE:
<221> NAME/KEY: misc_feature
<222> LOCATION: (2293)..(2293)
<223> OTHER INFORMATION: A, C, T or G
<220> FEATURE:
<221> NAME/KEY: misc_feature
<222> LOCATION: (2543)..(2543)
<223> OTHER INFORMATION: A, C, T or G
<220> FEATURE:
<221> NAME/KEY: misc_feature
```

<222> LOCATION: (2723)..(2723)
<223> OTHER INFORMATION: A, C, T or G
<220> FEATURE:
<221> NAME/KEY: misc_feature
<222> LOCATION: (2782)..(2782)
<223> OTHER INFORMATION: A, C, T or G
<220> FEATURE:
<221> NAME/KEY: misc_feature
<222> LOCATION: (2925)..(2925)
<223> OTHER INFORMATION: A, C, T or G
<220> FEATURE:
<221> NAME/KEY: misc_feature
<222> LOCATION: (3498)..(3498)
<223> OTHER INFORMATION: A, C, T or G
<220> FEATURE:
<221> NAME/KEY: misc_feature
<222> LOCATION: (3627)..(3627)
<223> OTHER INFORMATION: A, C, T or G
<220> FEATURE:
<221> NAME/KEY: misc_feature
<222> LOCATION: (3714)..(3714)
<223> OTHER INFORMATION: A, C, T or G

<400> SEQUENCE: 1

```
agaaggccat cgcccagagt ggcaccgcca tttcccagct ggtctgtcaa ctaccagccg      60
ctcaagtaca ncgncggctg ctggcagcca aggtgggctg tgaccgagag gacagtgctg     120
aannnngcnn nntgnnnntg gagtngtctg cgccggaang ccntcccggg agctggtgga     180
ccaggacgtg cagcctgccc gctaccacat cgcctttggg cccgtggtgg atggcgacgt     240
ggtccccgat gaccctgaga tcctcatgca gcagggagaa ttcctcaact acgacatgct     300
catcggtgtc aaccagggag agggcctcaa gttcgtggag gactctgcag agagcgagga     360
cggtgtgtct gccagcgcct ttgacttcac tgtctccaac tttgtggaca acctgtatgg     420
ctacccggaa ggcaaggatg tgcttcggga gaccatcaag tttatgtaca cagactgggc     480
cgaccgggac aatggcgaaa tgcgccgcaa acccctgct ggcgctcttt actgaccacc     540
aatgggtggc accagctgtg gccactgcca agctgcacgc cgactaccag tctcccgtct     600
acttttacac cttctaccac cactgccagg cggagggccg gcctgagtgg gcagatgcgg     660
cgcacgggga tgaactgccc tatgtctttg gcgtgcccat ggtgggtgcc accgacctcn     720
ttcccctgta acttctccaa gaatgacgtc atgctcagtg ccgtggtcat gacctactgg     780
accaacttcg ccaagactgg ggaccccaac cagccggtgc gcagataac caagttcatc     840
cacaccaagc ccaatcgctt cgaggaggtg gtgtggagca aattcaacag caaggagaag     900
cagtatctgc acataggcct gaagccacgc gtgcgtgaca actaccgcgc caacaaggtg     960
gccttctggc tggagctcgt gccccacctg cacaacctgc acacggagct tttcaccacc    1020
accacgcgcc tgcctcccta cgccacgcgc tggccgcctc gtccccccg tggcgccccg    1080
ggcacaacgc cgcccccgcc gcctgccacc ctgcctcccg agcccgagcc cgagcccccn    1140
ccaagggcct atgaccgctt ccccggggac tcacggggact actccacgga gctgagcgtc    1200
accgtggccg tgggtgcctc cctcctcttc ctcaacatcc tggcctttgc tgccctctac    1260
tacaagcggg accggcggca ggagctgcgg tgcaggcggc ttagcccacc tggcggctca    1320
ggctctggcg tgcctggtgg gggncccccct gctncccgc cgcgggccgt gagctgccac    1380
cagaggagga gctggtgtca ctgcagctga agcggggtgg tggcgtcggg gcggaccctg    1440
ccgaggctct gcgccctgcc tgcccgcccg actancaccc tggccctgcg ccgggcaccg    1500
gacg atg tgc ctc ttc ttt gcc ccg ggg ccc tgn acc ctg ctg ncc cag    1549
     Met Cys Leu Phe Phe Ala Pro Gly Pro Xaa Thr Leu Leu Xaa Gln
     1               5                  10                  15
```

-continued

```
tgn cct ggg gcc acc gcc acc ccc acc gcc ccc ctc ccc ttc aat ctt    1597
Xaa Pro Gly Ala Thr Ala Thr Pro Thr Ala Pro Leu Pro Phe Asn Leu
             20                  25                  30 cgg gcc ctt ccc ccc gcc ccc tcc cac cgc tac cag cca caa caa cac    1645
Arg Ala Leu Pro Pro Ala Pro Ser His Arg Tyr Gln Pro Gln Gln His
 35                  40                  45 gct acc cca ccc cca ctc cac cac tcg ggt ata ggg ggt ggg tgg gga    1693
Ala Thr Pro Pro Pro Leu His His Ser Gly Ile Gly Gly Gly Trp Gly
         50                  55                  60 ggc cct cct ccc ccg ncc ctc cct ggc ccg gcc act ccg aag gca ggg    1741
Gly Pro Pro Pro Pro Xaa Leu Pro Gly Pro Ala Thr Pro Lys Ala Gly
 65                  70                  75 agg agg act tgg caa ctg gct ttt ctc ctg tgg ann nnn gnn tnn nnc    1789
Arg Arg Thr Trp Gln Leu Ala Phe Leu Leu Trp Xaa Xaa Xaa Xaa Xaa
 80                  85                  90                  95 gtn cac acg cca tcc agc agc gct aag gtg gac atg gga ttc ctc ccn    1837
Val His Thr Pro Ser Ser Ser Ala Lys Val Asp Met Gly Phe Leu Pro
                100                 105                 110 tgc gat gcg tgt ctt tcc cac gca gag aag ccc agt ctc ttc tct gga    1885
Cys Asp Ala Cys Leu Ser His Ala Glu Lys Pro Ser Leu Phe Ser Gly
        115                 120                 125 tct ggg cct ttg aac aac tgg ggg gcg ttt tct ccc ccc cat tgg gan    1933
Ser Gly Pro Leu Asn Asn Trp Gly Ala Phe Ser Pro Pro His Trp Xaa
130                 135                 140 cac cag tct tcg gtg tgt gga atg tgg tat ttt ccc gcg tgg agg tgt    1981
His Gln Ser Ser Val Cys Gly Met Trp Tyr Phe Pro Ala Trp Arg Cys
    145                 150                 155 gct ttc tca caa cgg ggt gtg ttt tcc cat gtg cag ggt gag gtt ttt    2029
Ala Phe Ser Gln Arg Gly Val Phe Ser His Val Gln Gly Glu Val Phe
160                 165                 170                 175 ttt tgc cac cct gga cac atg ttg gcc ccc tca aag aat ttc tgt ggg    2077
Phe Cys His Pro Gly His Met Leu Ala Pro Ser Lys Asn Phe Cys Gly
            180                 185                 190 gat ttg tac ccc aga atc ctg ttc ccc cat ccc ttc tcc cac ctc ctc    2125
Asp Leu Tyr Pro Arg Ile Leu Phe Pro His Pro Phe Ser His Leu Leu
        195                 200                 205 ccc tct ccc tcc ccc tgg nnn nna gna cnn nnn nnn cct gga agt ggt    2173
Pro Ser Pro Ser Pro Trp Xaa Xaa Xaa Xaa Xaa Xaa Pro Gly Ser Gly
    210                 215                 220 gtg ttc aca tac agt gac cct tgg cca cca gac cac aga gga tgg agc    2221
Val Phe Thr Tyr Ser Asp Pro Trp Pro Pro Asp His Arg Gly Trp Ser
225                 230                 235 ctg gga agc agc gag gaa atc aca gcc ccc tcg ccc ctg cct ccc ttg    2269
Leu Gly Ser Ser Glu Glu Ile Thr Ala Pro Ser Pro Leu Pro Pro Leu
240                 245                 250                 255 ccc cta ccc cgg cga agc atg ttn ccc ccc gac gcc ccc ctt ggc aca    2317
Pro Leu Pro Arg Arg Ser Met Xaa Pro Pro Asp Ala Pro Leu Gly Thr
                260                 265                 270 agt cag atg aag cac gtt ctg ccg ggg agg ccc tca cct tcc aga gag    2365
Ser Gln Met Lys His Val Leu Pro Gly Arg Pro Ser Pro Ser Arg Glu
        275                 280                 285 gac aga cac aga ttt cct gct ggg gga ggg agg agt cca cgc atc ctg    2413
Asp Arg His Arg Phe Pro Ala Gly Gly Gly Arg Ser Pro Arg Ile Leu
    290                 295                 300 atg ctg cct gga agc tta ttt tcc cgt ggc cag gat gca ttt ctc tga    2461
Met Leu Pro Gly Ser Leu Phe Ser Arg Gly Gln Asp Ala Phe Leu
305                 310                 315 gtggaaacag gttcttgcat gtggatgtgt gtttccccag gcagacggcc cctctcttcc   2521
cagcacttcc ctgcctcccc cnaggcctca ggcccagcac ccagttcctc ctcacatggc   2581
```

```
aggtgagcac agacttctag ttggcaggag ctgaggaggg tgaacaaacc ccgagggagg    2641
cccggccctt gctcccgagt tggggggagg gggtgtggca acgtgccccc cgcagaggcc    2701
acgcatgttt gaccaaagcc cntcattgtg gtccgaggac agccttttcc ccaggcctca    2761
gagcattgct catccgtgcc naaactgggt aggtggattt gagcggaaag actcccaaaa    2821
tgtgccaaga atttcccagt cccaggcagg cagggggaaa ctaagggcaa caggataca    2881 gggcgaggga tgtggcaggt gaggggggctc ccgcctgtgc cccnttctcc tcaccatgtc    2941
tcccccaccc tgcctcagtt ctccgttccc cttcatctcc gtcccctct ttgaagctgt    3001 ccccatctca gtgtcagacc agccttctcc tcagctgacc accctcctct gacccacgcc    3061
ccctccttgt ctgaaagaaa ggagccttga atggtggagg gaggcagtgg ggagaaaggt    3121
ctcaccggac aggttgggag aatgaggtca gcggtgctgg ggaacagatg gaggggggcag    3181 tggggacagg gcttgggcag acaccagcag gaataatttg aaatgtgtga ggtgactccc    3241
cggagggcct tgggcttggg catttgggaa aagaatgatg tctggaaggg cttaagggac    3301
acagtggacg agggggagagt cctcatctgc tggcattttg tggggtgtta gtgccaaact    3361
tgaatagggg ctggggtgct gtcttccact gacacccaaa tccagaatcc ctggtcttga    3421
gtccccagaa ctttgcctct tgactgtccc ttctcttcct acctccatcc atggaaaatt    3481
agttattttc tgatccnttt cccctgcctg gtctagctcc tctccaaaca gccatgccct    3541
ccaaatgcta gagacctggg ccctgaaccc tgtagacaga tgccctcaga attggggcat    3601 gggaggggggg ctgggggacc ccatgnattc agccacggac tccaatgccc agctcctctc    3661
cccaaaacaa tcccgacaat cccttatccc taccccaacc ctttgcggct ctngtacaca    3721
ttttaaaacc tggcaaaaga tgaagagaat attgtaaata taaagtttta act           3774
```

<210> SEQ ID NO 2
<211> LENGTH: 318
<212> TYPE: PRT
<213> ORGANISM: Homo sapiens
<220> FEATURE:
<221> NAME/KEY: misc_feature
<222> LOCATION: (10)..(10)
<223> OTHER INFORMATION: The 'Xaa' at location 10 stands for Trp, or
      Cys.
<220> FEATURE:
<221> NAME/KEY: misc_feature
<222> LOCATION: (14)..(14)
<223> OTHER INFORMATION: The 'Xaa' at location 14 stands for Thr, Ala,
      Pro, or Ser.
<220> FEATURE:
<221> NAME/KEY: misc_feature
<222> LOCATION: (16)..(16)
<223> OTHER INFORMATION: The 'Xaa' at location 16 stands for Trp, or
      Cys.
<220> FEATURE:
<221> NAME/KEY: misc_feature
<222> LOCATION: (69)..(69)
<223> OTHER INFORMATION: The 'Xaa' at location 69 stands for Thr, Ala,
      Pro, or Ser.
<220> FEATURE:
<221> NAME/KEY: misc_feature
<222> LOCATION: (91)..(91)
<223> OTHER INFORMATION: The 'Xaa' at location 91 stands for Lys, Asn,
      Arg, Ser, Thr, Ile, or Met.
<220> FEATURE:
<221> NAME/KEY: misc_feature
<222> LOCATION: (92)..(92)
<223> OTHER INFORMATION: The 'Xaa' at location 92 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature -continued

```
<222> LOCATION: (93)..(93)
<223> OTHER INFORMATION: The 'Xaa' at location 93 stands for Glu, Asp,
      Gly, Ala, or Val.
<220> FEATURE:
<221> NAME/KEY: misc_feature
<222> LOCATION: (94)..(94)
<223> OTHER INFORMATION: The 'Xaa' at location 94 stands for Tyr, Trp,
      Cys, Ser, Leu, or Phe.
<220> FEATURE:
<221> NAME/KEY: misc_feature
<222> LOCATION: (95)..(95)
<223> OTHER INFORMATION: The 'Xaa' at location 95 stands for Asn, Ser,
      Thr, Ile, Asp, Gly, Ala, Val, His, Arg, Pro, Leu, Tyr, Cys, or
      Phe.
<220> FEATURE:
<221> NAME/KEY: misc_feature
<222> LOCATION: (143)..(143)
<223> OTHER INFORMATION: The 'Xaa' at location 143 stands for Glu, or
      Asp.
<220> FEATURE:
<221> NAME/KEY: misc_feature
<222> LOCATION: (214)..(214)
<223> OTHER INFORMATION: The 'Xaa' at location 214 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (215)..(215)
<223> OTHER INFORMATION: The 'Xaa' at location 215 stands for Lys, Arg,
      Thr, Ile, Glu, Gly, Ala, Val, Gln, Pro, Leu, or Ser.
<220> FEATURE:
<221> NAME/KEY: misc_feature
<222> LOCATION: (216)..(216)
<223> OTHER INFORMATION: The 'Xaa' at location 216 stands for Glu, Gly,
      Ala, or Val.
<220> FEATURE:
<221> NAME/KEY: misc_feature
<222> LOCATION: (217)..(217)
<223> OTHER INFORMATION: The 'Xaa' at location 217 stands for Gln, His,
      Arg, Pro, or Leu.
<220> FEATURE:
<221> NAME/KEY: misc_feature
<222> LOCATION: (218)..(218)
<223> OTHER INFORMATION: The 'Xaa' at location 218 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (219)..(219)
<223> OTHER INFORMATION: The 'Xaa' at location 219 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (263)..(263)
<223> OTHER INFORMATION: The 'Xaa' at location 263 stands for Leu, or
      Phe.

<400> SEQUENCE: 2

Met Cys Leu Phe Phe Ala Pro Gly Pro Xaa Thr Leu Leu Xaa Gln Xaa
1               5                   10                  15

Pro Gly Ala Thr Ala Thr Pro Thr Ala Pro Leu Pro Phe Asn Leu Arg
            20                  25                  30

Ala Leu Pro Pro Ala Pro Ser His Arg Tyr Gln Pro Gln Gln His Ala
        35                  40                  45

Thr Pro Pro Leu His His Ser Gly Ile Gly Gly Gly Trp Gly Gly
    50                  55                  60

Pro Pro Pro Pro Xaa Leu Pro Gly Pro Ala Thr Pro Lys Ala Gly Arg
65                  70                  75                  80

Arg Thr Trp Gln Leu Ala Phe Leu Leu Trp Xaa Xaa Xaa Xaa Xaa Val
                85                  90                  95

His Thr Pro Ser Ser Ser Ala Lys Val Asp Met Gly Phe Leu Pro Cys
```

-continued

```
                    100                 105                 110
Asp Ala Cys Leu Ser His Ala Glu Lys Pro Ser Leu Phe Ser Gly Ser
                115                 120                 125

Gly Pro Leu Asn Asn Trp Gly Ala Phe Ser Pro His Trp Xaa His
    130                 135                 140

Gln Ser Ser Val Cys Gly Met Trp Tyr Phe Pro Ala Trp Arg Cys Ala
145                 150                 155                 160

Phe Ser Gln Arg Gly Val Phe Ser His Val Gln Gly Glu Val Phe Phe
                165                 170                 175

Cys His Pro Gly His Met Leu Ala Pro Ser Lys Asn Phe Cys Gly Asp
            180                 185                 190

Leu Tyr Pro Arg Ile Leu Phe Pro His Pro Phe Ser His Leu Leu Pro
        195                 200                 205

Ser Pro Ser Pro Trp Xaa Xaa Xaa Xaa Xaa Pro Gly Ser Gly Val
    210                 215                 220

Phe Thr Tyr Ser Asp Pro Trp Pro Pro Asp His Arg Gly Trp Ser Leu
225                 230                 235                 240

Gly Ser Ser Glu Glu Ile Thr Ala Pro Ser Pro Leu Pro Pro Leu Pro
                245                 250                 255

Leu Pro Arg Arg Ser Met Xaa Pro Pro Asp Ala Pro Leu Gly Thr Ser
            260                 265                 270

Gln Met Lys His Val Leu Pro Gly Arg Pro Pro Ser Arg Glu Asp
        275                 280                 285

Arg His Arg Phe Pro Ala Gly Gly Arg Ser Pro Arg Ile Leu Met
    290                 295                 300

Leu Pro Gly Ser Leu Phe Ser Arg Gly Gln Asp Ala Phe Leu
305                 310                 315

<210> SEQ ID NO 3
<211> LENGTH: 1137
<212> TYPE: DNA
<213> ORGANISM: Homo sapiens
<220> FEATURE:
<221> NAME/KEY: CDS
<222> LOCATION: (125)..(1078)
<223> OTHER INFORMATION:

<400> SEQUENCE: 3 ggcgggggc tttctctct ctctttcact gcaaggcggc ggcaggagag gttgtggtgc      60
tagtttctct aagccatcca gtgccatcct cgtcgctgca gcgacacacg ctctcgccgc    120 cgcc atg act gag cag atg acc ctt cgt ggc acc ctc aag ggc cac aac    169
     Met Thr Glu Gln Met Thr Leu Arg Gly Thr Leu Lys Gly His Asn
     1               5                   10                  15 ggc tgg gta acc cag atc gct act acc ccg cag ttc ccg gac atg atc    217
Gly Trp Val Thr Gln Ile Ala Thr Thr Pro Gln Phe Pro Asp Met Ile
            20                  25                  30 ctc tcc gcc tct cga gat aag acc atc atc atg tgg aaa ctg acc agg    265
Leu Ser Ala Ser Arg Asp Lys Thr Ile Ile Met Trp Lys Leu Thr Arg
        35                  40                  45 gat gag acc aac tat gga att cca cag cgt gct ctg cgg ggt cac tcc    313
Asp Glu Thr Asn Tyr Gly Ile Pro Gln Arg Ala Leu Arg Gly His Ser
    50                  55                  60 cac ttt gtt agt gat gtg gtt atc tcc tca gat ggc cag ttt gcc ctc    361
His Phe Val Ser Asp Val Val Ile Ser Ser Asp Gly Gln Phe Ala Leu
65                  70                  75 tca ggc tcc tgg gat gga acc ctg cgc ctc tgg gat ctc aca acg ggc    409
Ser Gly Ser Trp Asp Gly Thr Leu Arg Leu Trp Asp Leu Thr Thr Gly
```

|   |   |   |   |   |   |   |   |   |   |   |   |   |   |   |   |     |
|---|---|---|---|---|---|---|---|---|---|---|---|---|---|---|---|-----|
| 80 |   |   |   |   | 85 |   |   |   |   | 90 |   |   |   |   | 95 |     |
| acc | acc | acg | agg | cga | ttt | gtg | ggc | cat | acc | aag | gat | gtg | ctg | agt | gtg | 457 |
| Thr | Thr | Thr | Arg | Arg | Phe | Val | Gly | His | Thr | Lys | Asp | Val | Leu | Ser | Val |   |
|     |     |     |     | 100 |     |     |     |     | 105 |     |     |     |     | 110 |     |   |
| gcc | ttc | tcc | tct | gac | aac | cgg | cag | att | gtc | tct | gga | tct | cga | gat | aaa | 505 |
| Ala | Phe | Ser | Ser | Asp | Asn | Arg | Gln | Ile | Val | Ser | Gly | Ser | Arg | Asp | Lys |   |
|     |     |     | 115 |     |     |     |     | 120 |     |     |     |     | 125 |     |     |   |
| acc | atc | aag | cta | tgg | aat | acc | ctg | ggt | gtg | tgc | aaa | tac | act | gtc | cag | 553 |
| Thr | Ile | Lys | Leu | Trp | Asn | Thr | Leu | Gly | Val | Cys | Lys | Tyr | Thr | Val | Gln |   |
|     |     | 130 |     |     |     |     | 135 |     |     |     |     | 140 |     |     |     |   |
| gat | gag | agc | cac | tca | gag | tgg | gtg | tct | tgt | gtc | cgc | ttc | tcg | ccc | aac | 601 |
| Asp | Glu | Ser | His | Ser | Glu | Trp | Val | Ser | Cys | Val | Arg | Phe | Ser | Pro | Asn |   |
|     | 145 |     |     |     |     | 150 |     |     |     |     | 155 |     |     |     |     |   |
| agc | agc | aac | cct | atc | atc | gtc | tcc | tgt | ggc | tgg | gac | aag | ctg | gtc | aag | 649 |
| Ser | Ser | Asn | Pro | Ile | Ile | Val | Ser | Cys | Gly | Trp | Asp | Lys | Leu | Val | Lys |   |
| 160 |     |     |     |     | 165 |     |     |     |     | 170 |     |     |     |     | 175 |   |
| gta | tgg | aac | ctg | gct | aac | tgc | aag | ctg | aag | acc | aac | cac | att | ggc | cac | 697 |
| Val | Trp | Asn | Leu | Ala | Asn | Cys | Lys | Leu | Lys | Thr | Asn | His | Ile | Gly | His |   |
|     |     |     |     | 180 |     |     |     |     | 185 |     |     |     |     | 190 |     |   |
| aca | ggc | tat | ctg | aac | acg | gtg | act | gtc | tct | cca | gat | gga | tcc | ctc | tgt | 745 |
| Thr | Gly | Tyr | Leu | Asn | Thr | Val | Thr | Val | Ser | Pro | Asp | Gly | Ser | Leu | Cys |   |
|     |     |     | 195 |     |     |     |     | 200 |     |     |     |     | 205 |     |     |   |
| gct | tct | gga | ggc | aag | gat | ggc | cag | gcc | atg | tta | tgg | gat | ctc | aac | gaa | 793 |
| Ala | Ser | Gly | Gly | Lys | Asp | Gly | Gln | Ala | Met | Leu | Trp | Asp | Leu | Asn | Glu |   |
|     |     | 210 |     |     |     |     | 215 |     |     |     |     | 220 |     |     |     |   |
| ggc | aaa | cac | ctt | tac | acg | cta | gat | ggt | ggg | gac | atc | atc | aac | gcc | ctg | 841 |
| Gly | Lys | His | Leu | Tyr | Thr | Leu | Asp | Gly | Gly | Asp | Ile | Ile | Asn | Ala | Leu |   |
|     | 225 |     |     |     |     | 230 |     |     |     |     | 235 |     |     |     |     |   |
| tgc | ttc | agc | cct | aac | cgc | tac | tgg | ctg | tgt | gct | gcc | aca | ggc | ccc | agc | 889 |
| Cys | Phe | Ser | Pro | Asn | Arg | Tyr | Trp | Leu | Cys | Ala | Ala | Thr | Gly | Pro | Ser |   |
| 240 |     |     |     |     | 245 |     |     |     |     | 250 |     |     |     |     | 255 |   |
| atc | aag | atc | tgg | gat | tta | gag | gga | aag | atc | att | gta | gat | gaa | ctg | aag | 937 |
| Ile | Lys | Ile | Trp | Asp | Leu | Glu | Gly | Lys | Ile | Ile | Val | Asp | Glu | Leu | Lys |   |
|     |     |     |     | 260 |     |     |     |     | 265 |     |     |     |     | 270 |     |   |
| caa | gaa | gtt | atc | agt | acc | agc | agc | aag | gca | gaa | cca | ccc | cag | tgc | acc | 985 |
| Gln | Glu | Val | Ile | Ser | Thr | Ser | Ser | Lys | Ala | Glu | Pro | Pro | Gln | Cys | Thr |   |
|     |     |     | 275 |     |     |     |     | 280 |     |     |     |     | 285 |     |     |   |
| tcc | ctg | gcc | tgg | tct | gct | gat | ggc | cag | act | ctg | ttt | gct | ggc | tac | acg | 1033 |
| Ser | Leu | Ala | Trp | Ser | Ala | Asp | Gly | Gln | Thr | Leu | Phe | Ala | Gly | Tyr | Thr |   |
|     |     | 290 |     |     |     |     | 295 |     |     |     |     | 300 |     |     |     |   |
| gac | aac | ctg | gtg | cga | gtg | tgg | cag | gtg | acc | att | ggc | aca | cgc | tag |     | 1078 |
| Asp | Asn | Leu | Val | Arg | Val | Trp | Gln | Val | Thr | Ile | Gly | Thr | Arg |     |     |   |
|     | 305 |     |     |     |     | 310 |     |     |     |     | 315 |     |     |     |     |   | aagtttatgg cagagcttta caaataaaaa aaaaactgg caaaaaaaaa aaaaaaaa    1137

<210> SEQ ID NO 4
<211> LENGTH: 317
<212> TYPE: PRT
<213> ORGANISM: Homo sapiens

<400> SEQUENCE: 4

Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
            20                  25                  30

Ser Ala Ser Arg Asp Lys Thr Ile Ile Met Trp Lys Leu Thr Arg Asp
        35                  40                  45

Glu Thr Asn Tyr Gly Ile Pro Gln Arg Ala Leu Arg Gly His Ser His
    50                  55                  60

-continued

```
Phe Val Ser Asp Val Val Ile Ser Ser Asp Gly Gln Phe Ala Leu Ser
 65                  70                  75                  80

Gly Ser Trp Asp Gly Thr Leu Arg Leu Trp Asp Leu Thr Thr Gly Thr
                 85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
        115                 120                 125

Ile Lys Leu Trp Asn Thr Leu Gly Val Cys Lys Tyr Thr Val Gln Asp
130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
        195                 200                 205

Ser Gly Gly Lys Asp Gly Gln Ala Met Leu Trp Asp Leu Asn Glu Gly
    210                 215                 220

Lys His Leu Tyr Thr Leu Asp Gly Gly Asp Ile Ile Asn Ala Leu Cys
225                 230                 235                 240

Phe Ser Pro Asn Arg Tyr Trp Leu Cys Ala Ala Thr Gly Pro Ser Ile
                245                 250                 255

Lys Ile Trp Asp Leu Glu Gly Lys Ile Ile Val Asp Glu Leu Lys Gln
            260                 265                 270

Glu Val Ile Ser Thr Ser Ser Lys Ala Glu Pro Gln Cys Thr Ser
        275                 280                 285

Leu Ala Trp Ser Ala Asp Gly Gln Thr Leu Phe Ala Gly Tyr Thr Asp
    290                 295                 300

Asn Leu Val Arg Val Trp Gln Val Thr Ile Gly Thr Arg
305                 310                 315
```

<210> SEQ ID NO 5
<211> LENGTH: 4602
<212> TYPE: DNA
<213> ORGANISM: Homo sapiens
<220> FEATURE:
<221> NAME/KEY: CDS
<222> LOCATION: (1)..(2796)
<223> OTHER INFORMATION:

<400> SEQUENCE: 5

```
atg aaa gcg agc tca ggg agg tgc ggg ctg gtg cgg tgg ctg cag gta    48
Met Lys Ala Ser Ser Gly Arg Cys Gly Leu Val Arg Trp Leu Gln Val
1               5                   10                  15 ctg ttg ccc ttc ctg ttg tct ttg ttc ccc ggg gct ctc cca gtc cag    96
Leu Leu Pro Phe Leu Leu Ser Leu Phe Pro Gly Ala Leu Pro Val Gln
            20                  25                  30 atc cgc tat tca att cca gag gag ctg gcc aaa aac tcg gtc gta gga    144
Ile Arg Tyr Ser Ile Pro Glu Glu Leu Ala Lys Asn Ser Val Val Gly
        35                  40                  45 aac ctc gcc aag gat ctg ggg ctc agc gtc cgg gac ttg cca gcc cgg    192
Asn Leu Ala Lys Asp Leu Gly Leu Ser Val Arg Asp Leu Pro Ala Arg
    50                  55                  60 aag ctg cgg gtt agc gcg gag aag gaa tat ttc aca gta aac cca gaa    240
Lys Leu Arg Val Ser Ala Glu Lys Glu Tyr Phe Thr Val Asn Pro Glu
```

-continued

| | | | |
|---|---|---|---|
| agc gga gac tta ctt gtg agt gac aga ata gac cga gaa cag ata tgc<br>Ser Gly Asp Leu Leu Val Ser Asp Arg Ile Asp Arg Glu Gln Ile Cys<br>                        85                                    90                                  95 | 288 |

```
                65                  70                  75                  80
agc gga gac tta ctt gtg agt gac aga ata gac cga gaa cag ata tgc       288
Ser Gly Asp Leu Leu Val Ser Asp Arg Ile Asp Arg Glu Gln Ile Cys
                85                  90                  95 ggg aag cag cct ctg tgt gtt ctg gat ttc gat act gtc gct gaa aat       336
Gly Lys Gln Pro Leu Cys Val Leu Asp Phe Asp Thr Val Ala Glu Asn
            100                 105                 110 cca cta aat att ttc tac ata gca gta att gtg cag gat ata aat gat       384
Pro Leu Asn Ile Phe Tyr Ile Ala Val Ile Val Gln Asp Ile Asn Asp
        115                 120                 125 aat acc ccg cta ttc aaa cag act aag att aat tta aaa att ggc gaa       432
Asn Thr Pro Leu Phe Lys Gln Thr Lys Ile Asn Leu Lys Ile Gly Glu
    130                 135                 140 tcc act aag cca ggt aca aca ttt cca ctt gac cca gcc ctg gat tca       480
Ser Thr Lys Pro Gly Thr Thr Phe Pro Leu Asp Pro Ala Leu Asp Ser
145                 150                 155                 160 gat gtt ggt cct aac tca cta caa aga tac cac ctt aat gac aac gag       528
Asp Val Gly Pro Asn Ser Leu Gln Arg Tyr His Leu Asn Asp Asn Glu
                165                 170                 175 tac ttt gat ctc gct gag aaa cag act cca gat ggt cgt aaa tat cct       576
Tyr Phe Asp Leu Ala Glu Lys Gln Thr Pro Asp Gly Arg Lys Tyr Pro
            180                 185                 190 gag ttg att cta aaa cac tct ctg gac aga gaa gag cac agt tta cat       624
Glu Leu Ile Leu Lys His Ser Leu Asp Arg Glu Glu His Ser Leu His
        195                 200                 205 caa ttg gtc ctc aca gct gtg gat ggc gga gac cca cct caa agt ggc       672
Gln Leu Val Leu Thr Ala Val Asp Gly Gly Asp Pro Pro Gln Ser Gly
    210                 215                 220 acg acc caa atc cga atc aaa gtc acg gat gcc aac gat aac cct cca       720
Thr Thr Gln Ile Arg Ile Lys Val Thr Asp Ala Asn Asp Asn Pro Pro
225                 230                 235                 240 gtg ttc agc cag gac gtg tac agg gtc acc ctg agg gag gac gtg ccg       768
Val Phe Ser Gln Asp Val Tyr Arg Val Thr Leu Arg Glu Asp Val Pro
                245                 250                 255 ccg ggc ttc ttt gtg ctt caa gtg aca gcc acc gac cgg gat gaa ggc       816
Pro Gly Phe Phe Val Leu Gln Val Thr Ala Thr Asp Arg Asp Glu Gly
            260                 265                 270 ata aac gca gag atc acc tac tcc ttt cat aat gtg gac gaa caa gtg       864
Ile Asn Ala Glu Ile Thr Tyr Ser Phe His Asn Val Asp Glu Gln Val
        275                 280                 285 aaa cac ttt ttc aac tta aat gaa aaa aca gga gaa atc acg aca aag       912
Lys His Phe Phe Asn Leu Asn Glu Lys Thr Gly Glu Ile Thr Thr Lys
    290                 295                 300 gat gat ttg gat ttt gag att gca agt agt tac act ctg agt atc gaa       960
Asp Asp Leu Asp Phe Glu Ile Ala Ser Ser Tyr Thr Leu Ser Ile Glu
305                 310                 315                 320 gca aaa gat cct gga gat cta gca gcc cac tgc agt atc caa gtt gaa      1008
Ala Lys Asp Pro Gly Asp Leu Ala Ala His Cys Ser Ile Gln Val Glu
                325                 330                 335 att ctt gat gac aac gat tgt gca cct gaa gtt att gtg act tca gta      1056
Ile Leu Asp Asp Asn Asp Cys Ala Pro Glu Val Ile Val Thr Ser Val
            340                 345                 350 tct act ccc cta ccg gag gat tcg cca cca gga aca gtg atc gcc ttg      1104
Ser Thr Pro Leu Pro Glu Asp Ser Pro Pro Gly Thr Val Ile Ala Leu
        355                 360                 365 ata aaa acg aga gac aga gac tct gga gaa aat gga gaa gtt tac tgc      1152
Ile Lys Thr Arg Asp Arg Asp Ser Gly Glu Asn Gly Glu Val Tyr Cys
    370                 375                 380 caa gtg ttg gga aat gcc aag ttt att ttg aaa tct tcc tca aag aac      1200
```

```
Gln Val Leu Gly Asn Ala Lys Phe Ile Leu Lys Ser Ser Lys Asn
385                 390                 395                 400 tat tac aaa cta gtg aca gac ggc gct ctg gac cgg gag gag atc cca    1248
Tyr Tyr Lys Leu Val Thr Asp Gly Ala Leu Asp Arg Glu Glu Ile Pro
                405                 410                 415 gaa tac aat ctc acc atc aca gcc acc gac ggg ggc aag ccg ccc ctc    1296
Glu Tyr Asn Leu Thr Ile Thr Ala Thr Asp Gly Gly Lys Pro Pro Leu
            420                 425                 430 tcc tcc agc ata att gtc acc ctg cac atc tcc gac gtc aac gat aat    1344
Ser Ser Ser Ile Ile Val Thr Leu His Ile Ser Asp Val Asn Asp Asn
        435                 440                 445 gcc cca gtt ttc caa cag act tcc tac atg gtt cac gtg gca gag aac    1392
Ala Pro Val Phe Gln Gln Thr Ser Tyr Met Val His Val Ala Glu Asn
    450                 455                 460 aat cct cct ggc gcc tct atc gct caa atc agt gcc tct gac cct gac    1440
Asn Pro Pro Gly Ala Ser Ile Ala Gln Ile Ser Ala Ser Asp Pro Asp
465                 470                 475                 480 ttg ggc ccc agt ggc caa gtt tcc tac tcc atc gta gcg agc gac ctg    1488
Leu Gly Pro Ser Gly Gln Val Ser Tyr Ser Ile Val Ala Ser Asp Leu
                485                 490                 495 aag ccg cgg gag att tta tcc tac gtg tcc gtg agc gcg cag agc ggg    1536
Lys Pro Arg Glu Ile Leu Ser Tyr Val Ser Val Ser Ala Gln Ser Gly
            500                 505                 510 gtg gtg ttc gcg cag cgc gcc ttc gat cat gag cag ctg cgc gcc ttc    1584
Val Val Phe Ala Gln Arg Ala Phe Asp His Glu Gln Leu Arg Ala Phe
        515                 520                 525 gag ctc aca ctg cag gcc cgc gac cag ggc tcg ccc gcg ctc agc gcc    1632
Glu Leu Thr Leu Gln Ala Arg Asp Gln Gly Ser Pro Ala Leu Ser Ala
    530                 535                 540 aac gtg agc ctg cgc gtg tta gtg ggc gac ctc aat gac aat gcg cca    1680
Asn Val Ser Leu Arg Val Leu Val Gly Asp Leu Asn Asp Asn Ala Pro
545                 550                 555                 560 cgg gtg ctg tac ccc gcg ctg ggg cct gat ggc tcc gcc ctc ttc gat    1728
Arg Val Leu Tyr Pro Ala Leu Gly Pro Asp Gly Ser Ala Leu Phe Asp
                565                 570                 575 atg gtg cca cgc gcc gca gag ccc ggc tac ctg gtg acc aag gtg gtg    1776
Met Val Pro Arg Ala Ala Glu Pro Gly Tyr Leu Val Thr Lys Val Val
            580                 585                 590 gcg gtg gac gca gac tca gga cac aac gct tgg ctg tcc tac cac gtg    1824
Ala Val Asp Ala Asp Ser Gly His Asn Ala Trp Leu Ser Tyr His Val
        595                 600                 605 ctg cag gcc agc gag ccc ggg ctc ttc agc ctg ggg ttg cgc acg ggt    1872
Leu Gln Ala Ser Glu Pro Gly Leu Phe Ser Leu Gly Leu Arg Thr Gly
    610                 615                 620 gag gtg cgc aca gcg cgt gcc ttg ggc gac agg gac gcg gcc cgc cag    1920
Glu Val Arg Thr Ala Arg Ala Leu Gly Asp Arg Asp Ala Ala Arg Gln
625                 630                 635                 640 cgc ctg ctg gtc gct gtg cgt gat gga gga cag ccg cca ctc tcc gct    1968
Arg Leu Leu Val Ala Val Arg Asp Gly Gly Gln Pro Pro Leu Ser Ala
                645                 650                 655 acg gcc acg ctg cac cta atc ttc gcg gat agc ctg caa gag gta ttg    2016
Thr Ala Thr Leu His Leu Ile Phe Ala Asp Ser Leu Gln Glu Val Leu
            660                 665                 670 cca gac ctc agc gac cgc cgg gag ccc tct gac ccc cag gca aaa ctg    2064
Pro Asp Leu Ser Asp Arg Arg Glu Pro Ser Asp Pro Gln Ala Lys Leu
        675                 680                 685 cag ttt tac ctg gtt gtg gcc ttg gcc ttg atc tca gtg ctc ttc ttc    2112
Gln Phe Tyr Leu Val Val Ala Leu Ala Leu Ile Ser Val Leu Phe Phe
    690                 695                 700
```

-continued

| | | |
|---|---|---|
| ctc gcg gtg att ctg gca atc tcc ctg cgc ctg cga ctc tct tcc agg<br>Leu Ala Val Ile Leu Ala Ile Ser Leu Arg Leu Arg Leu Ser Ser Arg<br>705                      710                      715                      720 | 2160 |
| tca gat gct tgg gac tgt ttt cag cct ggt ctc agc tcc aag cct gga<br>Ser Asp Ala Trp Asp Cys Phe Gln Pro Gly Leu Ser Ser Lys Pro Gly<br>                      725                      730                      735 | 2208 |
| cct ggg gtt ctc ccc aat tac agt gag ggt aca ttg ccc tat tcc tac<br>Pro Gly Val Leu Pro Asn Tyr Ser Glu Gly Thr Leu Pro Tyr Ser Tyr<br>                    740                      745                      750 | 2256 |
| aac ctg tgt gtt gcc tca caa tca gcc aag aca gag ttc aat ttt ctg<br>Asn Leu Cys Val Ala Ser Gln Ser Ala Lys Thr Glu Phe Asn Phe Leu<br>755                      760                      765 | 2304 |
| aac ata acc ccg gaa ttg gtt ccc gcg caa gat ctc gtc tgt gac aat<br>Asn Ile Thr Pro Glu Leu Val Pro Ala Gln Asp Leu Val Cys Asp Asn<br>770                      775                      780 | 2352 |
| gcc tct tgg gaa caa aat aca aat cat gga gcc gct ggg gtc cct ttt<br>Ala Ser Trp Glu Gln Asn Thr Asn His Gly Ala Ala Gly Val Pro Phe<br>785                      790                      795                      800 | 2400 |
| gcc tca gat act att ttg aag caa gcc ccg ccc aac acg gac tgg cgt<br>Ala Ser Asp Thr Ile Leu Lys Gln Ala Pro Pro Asn Thr Asp Trp Arg<br>                      805                      810                      815 | 2448 |
| ttc tct cag gcc cag aga ccc ggc acc agc ggc tcc caa aat ggc gat<br>Phe Ser Gln Ala Gln Arg Pro Gly Thr Ser Gly Ser Gln Asn Gly Asp<br>820                      825                      830 | 2496 |
| gac acc ggc acc tgg ccc aac aac cag ttt gac aca gag atg ctg caa<br>Asp Thr Gly Thr Trp Pro Asn Asn Gln Phe Asp Thr Glu Met Leu Gln<br>                      835                      840                      845 | 2544 |
| gcc atg atc ttg gcg tcc gcc agt gaa gct gct gat ggg agc tcc acc<br>Ala Met Ile Leu Ala Ser Ala Ser Glu Ala Ala Asp Gly Ser Ser Thr<br>850                      855                      860 | 2592 |
| ctg gga ggg ggt gcc ggc acc atg gga ttg agc gcc cgc tac gga ccc<br>Leu Gly Gly Gly Ala Gly Thr Met Gly Leu Ser Ala Arg Tyr Gly Pro<br>865                      870                      875                      880 | 2640 |
| cag ttc acc ctg cag cac gtg ccc gac tac cgc cag aat gtc tac atc<br>Gln Phe Thr Leu Gln His Val Pro Asp Tyr Arg Gln Asn Val Tyr Ile<br>                      885                      890                      895 | 2688 |
| cca ggc agc aat gcc aca ctg acc aac gca gct ggc aag cgg gat ggc<br>Pro Gly Ser Asn Ala Thr Leu Thr Asn Ala Ala Gly Lys Arg Asp Gly<br>900                      905                      910 | 2736 |
| aag gcc cca gca ggt ggc aat ggc aac aag aag aag tcg ggc aag aag<br>Lys Ala Pro Ala Gly Gly Asn Gly Asn Lys Lys Lys Ser Gly Lys Lys<br>                      915                      920                      925 | 2784 |
| gag aag aag taa catggaggcc aggccaagag ccacagggcg ccctctcccc<br>Glu Lys Lys<br>930 | 2836 |
| aaccagccca gcttctcctt acctgcaccc aggcctcaga gtttcagggc taaccccag | 2896 |
| aatactggta ggggccaagg ccatgctccc cttgggaaac agaaacaagt gcccagtcag | 2956 |
| cacctacccc ttcccccca gggggttgaa tatgcaaaag cagttccgct gggaaccccc | 3016 |
| atccaatcaa ctgctgtacc catgggggta gtggggttac tgtagacacc aagaaccatt | 3076 |
| tgccacaccc cgtttagtta cagctgaact cctccatctt ccaaatcaat caggcccatc | 3136 |
| catcccatgc ctccctcctc cccaccccac tccaacagtt cctctttccc gagtaaggtg | 3196 |
| gttgggtgt tgaagtacca agtaacctac aagcctccta gttctgaaaa gttggaaggg | 3256 |
| catcatgacc tcttggcctc tcctttgatt ctcaatcttc cccaaagca tggtttggtg | 3316 |
| ccagcccctt cacctccttc cagagcccaa gatcaatgct caagttttgg aggacatgat | 3376 |
| caccatcccc atggtactga tgcttgctgg atttagggag ggcatttttgc taccaagcct | 3436 |

```
cttcccaacg ccctggggac cagtcttctg ttttgttttt cattgtttga cgtttccact    3496
gcatgccttg acttccccca cctcctcctc aaacaagaga ctccactgca tgttccaaga    3556
cagtatgggg tggtaagata aggaagggaa gtgtgtggat gtggatggtg ggggcatgga    3616
caaagcttga cacatcaagt tatcaaggcc ttggaggagg ctctgtatgt cctcagggga    3676
ctgacaacat cctccagatt ccagccataa accaataact aggctggacc cttcccacta    3736
cataataggg ctcagcccag gcagccagct ttgggctgag ctaacaggac caatggatta    3796
aactggcatt tcagtccaag gaagctcgaa gcaggtttag gaccaggtcc ccttgagagg    3856
tcagaggggc ctctgtgggt gctgggtact ccagaggtgc cactggtgga agggtcagcg    3916
gagccccagc aggaagggtg ggccagccag gccattctta gtccctgggt tggggaggca    3976
gggagctagg gcagggacca aatgaacaga aagtctcagc ccaggatggg gcttcttcaa    4036
cagggcccct gccctcctga agcctcagtc cttcaccttg ccaggtgccg tttctcttcc    4096
gtgaaggcca ctgcccaggt ccccagtgcg cccctagtg gccatagcct ggttaaagtt     4156
ccccagtgcc tccttgtgca tagaccttct tctcccaccc ccttctgccc ctgggtcccc    4216
ggccatccag cggggctgcc agagaacccc agacctgccc ttacagtagt gtagcgcccc    4276
ctccctcttt cggctggtgt agaatagcca gtagtgtagt gcggtgtgct tttacgtgat    4336
ggcgggtggg cagcgggcgg cgggctccgc gcagccgtct gtccttgatc tgcccgcggc    4396
ggcccgtgtt gtgttttgtg ctgtgtccac gcgctaaggc gacccctcc cccgtactga     4456 cttctcctat aagcgcttct cttcgcatag tcacgtagcc cccaccccac cctcttcctg    4516
tgtctcacgc aagttttata ctctaatatt tatatggctt tttttcttcg acaaaaaaat    4576
aataaaacgt ttcttctgaa aagctg                                         4602
```

<210> SEQ ID NO 6
<211> LENGTH: 931
<212> TYPE: PRT
<213> ORGANISM: Homo sapiens

<400> SEQUENCE: 6

```
Met Lys Ala Ser Ser Gly Arg Cys Gly Leu Val Arg Trp Leu Gln Val
1               5                   10                  15

Leu Leu Pro Phe Leu Leu Ser Leu Phe Pro Gly Ala Leu Pro Val Gln
            20                  25                  30

Ile Arg Tyr Ser Ile Pro Glu Glu Leu Ala Lys Asn Ser Val Val Gly
        35                  40                  45

Asn Leu Ala Lys Asp Leu Gly Leu Ser Val Arg Asp Leu Pro Ala Arg
    50                  55                  60

Lys Leu Arg Val Ser Ala Glu Lys Glu Tyr Phe Thr Val Asn Pro Glu
65                  70                  75                  80

Ser Gly Asp Leu Leu Val Ser Asp Arg Ile Asp Arg Glu Gln Ile Cys
                85                  90                  95

Gly Lys Gln Pro Leu Cys Val Leu Asp Phe Asp Thr Val Ala Glu Asn
            100                 105                 110

Pro Leu Asn Ile Phe Tyr Ile Ala Val Ile Val Gln Asp Ile Asn Asp
        115                 120                 125

Asn Thr Pro Leu Phe Lys Gln Thr Lys Ile Asn Leu Lys Ile Gly Glu
    130                 135                 140

Ser Thr Lys Pro Gly Thr Thr Phe Pro Leu Asp Pro Ala Leu Asp Ser
145                 150                 155                 160
```

```
Asp Val Gly Pro Asn Ser Leu Gln Arg Tyr His Leu Asn Asp Asn Glu
            165                 170                 175

Tyr Phe Asp Leu Ala Glu Lys Gln Thr Pro Asp Gly Arg Lys Tyr Pro
            180                 185                 190

Glu Leu Ile Leu Lys His Ser Leu Asp Arg Glu His Ser Leu His
            195                 200                 205

Gln Leu Val Leu Thr Ala Val Asp Gly Gly Asp Pro Pro Gln Ser Gly
210                 215                 220

Thr Thr Gln Ile Arg Ile Lys Val Thr Asp Ala Asn Asp Asn Pro Pro
225                 230                 235                 240

Val Phe Ser Gln Asp Val Tyr Arg Val Thr Leu Arg Glu Asp Val Pro
                245                 250                 255

Pro Gly Phe Phe Val Leu Gln Val Thr Ala Thr Asp Arg Asp Glu Gly
            260                 265                 270

Ile Asn Ala Glu Ile Thr Tyr Ser Phe His Asn Val Asp Glu Gln Val
            275                 280                 285

Lys His Phe Phe Asn Leu Asn Glu Lys Thr Gly Glu Ile Thr Thr Lys
290                 295                 300

Asp Asp Leu Asp Phe Glu Ile Ala Ser Ser Tyr Thr Leu Ser Ile Glu
305                 310                 315                 320

Ala Lys Asp Pro Gly Asp Leu Ala Ala His Cys Ser Ile Gln Val Glu
                325                 330                 335

Ile Leu Asp Asp Asn Asp Cys Ala Pro Glu Val Ile Val Thr Ser Val
            340                 345                 350

Ser Thr Pro Leu Pro Glu Asp Ser Pro Gly Thr Val Ile Ala Leu
            355                 360                 365

Ile Lys Thr Arg Asp Arg Asp Ser Gly Glu Asn Gly Glu Val Tyr Cys
            370                 375                 380

Gln Val Leu Gly Asn Ala Lys Phe Ile Leu Lys Ser Ser Ser Lys Asn
385                 390                 395                 400

Tyr Tyr Lys Leu Val Thr Asp Gly Ala Leu Asp Arg Glu Glu Ile Pro
                405                 410                 415

Glu Tyr Asn Leu Thr Ile Thr Ala Thr Asp Gly Gly Lys Pro Pro Leu
            420                 425                 430

Ser Ser Ser Ile Ile Val Thr Leu His Ile Ser Asp Val Asn Asp Asn
            435                 440                 445

Ala Pro Val Phe Gln Gln Thr Ser Tyr Met Val His Val Ala Glu Asn
450                 455                 460

Asn Pro Pro Gly Ala Ser Ile Ala Gln Ile Ser Ala Ser Asp Pro Asp
465                 470                 475                 480

Leu Gly Pro Ser Gly Gln Val Ser Tyr Ser Ile Val Ala Ser Asp Leu
                485                 490                 495

Lys Pro Arg Glu Ile Leu Ser Tyr Val Ser Val Ser Ala Gln Ser Gly
            500                 505                 510

Val Val Phe Ala Gln Arg Ala Phe Asp His Glu Gln Leu Arg Ala Phe
            515                 520                 525

Glu Leu Thr Leu Gln Ala Arg Asp Gln Gly Ser Pro Ala Leu Ser Ala
            530                 535                 540

Asn Val Ser Leu Arg Val Leu Gly Asp Leu Asn Asp Asn Ala Pro
545                 550                 555                 560

Arg Val Leu Tyr Pro Ala Leu Gly Pro Asp Gly Ser Ala Leu Phe Asp
                565                 570                 575

Met Val Pro Arg Ala Ala Glu Pro Gly Tyr Leu Val Thr Lys Val Val
```

-continued

Ala Val Asp Ala Asp Ser Gly His Asn Ala Trp Leu Ser Tyr His Val
        595                 600                 605

Leu Gln Ala Ser Glu Pro Gly Leu Phe Ser Leu Gly Leu Arg Thr Gly
    610                 615                 620

Glu Val Arg Thr Ala Arg Ala Leu Gly Asp Arg Asp Ala Ala Arg Gln
625                 630                 635                 640

Arg Leu Leu Val Ala Val Arg Asp Gly Gly Gln Pro Pro Leu Ser Ala
                645                 650                 655

Thr Ala Thr Leu His Leu Ile Phe Ala Asp Ser Leu Gln Glu Val Leu
            660                 665                 670

Pro Asp Leu Ser Asp Arg Arg Glu Pro Ser Asp Pro Gln Ala Lys Leu
        675                 680                 685

Gln Phe Tyr Leu Val Val Ala Leu Ala Leu Ile Ser Val Leu Phe Phe
    690                 695                 700

Leu Ala Val Ile Leu Ala Ile Ser Leu Arg Leu Arg Leu Ser Ser Arg
705                 710                 715                 720

Ser Asp Ala Trp Asp Cys Phe Gln Pro Gly Leu Ser Ser Lys Pro Gly
                725                 730                 735

Pro Gly Val Leu Pro Asn Tyr Ser Glu Gly Thr Leu Pro Tyr Ser Tyr
            740                 745                 750

Asn Leu Cys Val Ala Ser Gln Ser Ala Lys Thr Glu Phe Asn Phe Leu
        755                 760                 765

Asn Ile Thr Pro Glu Leu Val Pro Ala Gln Asp Leu Val Cys Asp Asn
    770                 775                 780

Ala Ser Trp Glu Gln Asn Thr Asn His Gly Ala Ala Gly Val Pro Phe
785                 790                 795                 800

Ala Ser Asp Thr Ile Leu Lys Gln Ala Pro Pro Asn Thr Asp Trp Arg
                805                 810                 815

Phe Ser Gln Ala Gln Arg Pro Gly Thr Ser Gly Ser Gln Asn Gly Asp
            820                 825                 830

Asp Thr Gly Thr Trp Pro Asn Asn Gln Phe Asp Thr Glu Met Leu Gln
        835                 840                 845

Ala Met Ile Leu Ala Ser Ala Ser Glu Ala Ala Asp Gly Ser Ser Thr
    850                 855                 860

Leu Gly Gly Gly Ala Gly Thr Met Gly Leu Ser Ala Arg Tyr Gly Pro
865                 870                 875                 880

Gln Phe Thr Leu Gln His Val Pro Asp Tyr Arg Gln Asn Val Tyr Ile
                885                 890                 895

Pro Gly Ser Asn Ala Thr Leu Thr Asn Ala Ala Gly Lys Arg Asp Gly
            900                 905                 910

Lys Ala Pro Ala Gly Gly Asn Gly Asn Lys Lys Ser Gly Lys Lys
        915                 920                 925

Glu Lys Lys
    930

<210> SEQ ID NO 7
<211> LENGTH: 2991
<212> TYPE: DNA
<213> ORGANISM: Homo sapiens
<220> FEATURE:
<221> NAME/KEY: CDS
<222> LOCATION: (61)..(858)
<223> OTHER INFORMATION:

<400> SEQUENCE: 7

```
ccgccggccg gggccgctgg ctgcactcag cgccggagcc gggagctagc ggccgccgcc        60 atg tcc cac cag acc ggc atc caa gca agt gaa gat gtt aaa gag atc        108
Met Ser His Gln Thr Gly Ile Gln Ala Ser Glu Asp Val Lys Glu Ile
1               5                   10                  15 ttt gcc aga gcc aga aat gga aag tac aga ctt ctg aaa ata tct att        156
Phe Ala Arg Ala Arg Asn Gly Lys Tyr Arg Leu Leu Lys Ile Ser Ile
            20                  25                  30 gaa aat gag caa ctt gtg att gga tca tat agt cag cct tca gat tcc        204
Glu Asn Glu Gln Leu Val Ile Gly Ser Tyr Ser Gln Pro Ser Asp Ser
        35                  40                  45 tgg gat aag gat tat gat tcc ttt gtt tta ccc ctg ttg gag gac aaa        252
Trp Asp Lys Asp Tyr Asp Ser Phe Val Leu Pro Leu Leu Glu Asp Lys
    50                  55                  60 caa cca tgc tat ata tta ttc agg tta gat tct cag aat gcc cag gga        300
Gln Pro Cys Tyr Ile Leu Phe Arg Leu Asp Ser Gln Asn Ala Gln Gly
65                  70                  75                  80 tat gaa tgg ata ttc att gca tgg tct cca gat cat tct cat gtt cgt        348
Tyr Glu Trp Ile Phe Ile Ala Trp Ser Pro Asp His Ser His Val Arg
                85                  90                  95 caa aaa atg ttg tat gca gca aca aga gca act ctg aag aag gaa ttt        396
Gln Lys Met Leu Tyr Ala Ala Thr Arg Ala Thr Leu Lys Lys Glu Phe
            100                 105                 110 gga ggt ggc cac att aaa gat gaa ata ttt gga aca gta aag gaa gat        444
Gly Gly Gly His Ile Lys Asp Glu Ile Phe Gly Thr Val Lys Glu Asp
        115                 120                 125 gta tca tta cat gga tat aaa aaa tac ttg ctg tca caa tct tcc cct        492
Val Ser Leu His Gly Tyr Lys Lys Tyr Leu Leu Ser Gln Ser Ser Pro
    130                 135                 140 gcc cca ctg act gca gct gag gaa gaa tta cga cag att aaa atc aat        540
Ala Pro Leu Thr Ala Ala Glu Glu Glu Leu Arg Gln Ile Lys Ile Asn
145                 150                 155                 160 gag gta cag act gac gtg ggt gtg gac act aag cat caa aca cta caa        588
Glu Val Gln Thr Asp Val Gly Val Asp Thr Lys His Gln Thr Leu Gln
                165                 170                 175 gga gta gca ttt ccc att tct cga gaa gcc ttt cag gct ttg gaa aaa        636
Gly Val Ala Phe Pro Ile Ser Arg Glu Ala Phe Gln Ala Leu Glu Lys
            180                 185                 190 ttg aat aac aga cag ctc aac tat gtg cag ttg gaa ata gat ata aaa        684
Leu Asn Asn Arg Gln Leu Asn Tyr Val Gln Leu Glu Ile Asp Ile Lys
        195                 200                 205 aat gaa att ata att ttg gcc aac aca aca aat aca gaa ctg aaa gat        732
Asn Glu Ile Ile Ile Leu Ala Asn Thr Thr Asn Thr Glu Leu Lys Asp
    210                 215                 220 ttg cca aag agg att ccc aag gat tca gct cgt tac cat ttc ttt ctg        780
Leu Pro Lys Arg Ile Pro Lys Asp Ser Ala Arg Tyr His Phe Phe Leu
225                 230                 235                 240 tat aaa cat tcc cat gaa gga gac tat tta gag tcc ata gtt tta ttt        828
Tyr Lys His Ser His Glu Gly Asp Tyr Leu Glu Ser Ile Val Leu Phe
                245                 250                 255 att caa tgc ctg gat aca cat gca gta taa gagagcggat gctgtattct          878
Ile Gln Cys Leu Asp Thr His Ala Val
            260                 265 agctgcaaga gccctctgct agaaattgta gaaagacaac tacaaatgga tgtaattaga      938
aagatcgaga tagacaatgg ggatgagttg actgcagact tcctttatga agaagtacat      998
cccaagcagc aggcacacaa gcaaagtttt gcaaaaccaa aggtcctgc aggaaaaaga      1058 ggaattcgaa gactaattag gggcccagcg gaaactgaag ctactactga ttaaagtcgt     1118
```

```
cacattaaac attgcaatac tagttttta  aaagtccagc ttttagtaca ggagaactga    1178
aatcattcca tgttgatata agtagggaa  aaacattgta cttttggaa  aatagcactt    1238 ttcacttctg tgtgtttta  aaattaatgt tatagaagac tcatgattc  tattttgag     1298 ttaaagctag aaaagggttc aacataatgt ttaattttgt cacactgttt tcatagtgtt    1358
gattccacac ttcaaatact tcttaaaatt ttatacagtt gggccagctc tagaaagtct    1418
gatgtctcaa agggtaaact tactactttc ttgtgggaca aaggacctt  aaaatattca    1478 tattacttaa tgaatatgtt aaggaccagg ctagagtatt ttctaagctg gaaacttagt    1538
gtgcctcgga aaaggccgca agttgcttac tccgagtagc tgtgctagct ctgtcagact    1598
gtaggatcat gtctgcaact tttagaaata gtgctttata ttgcagcagt cttttatatt    1658
tgactttttt tttaatagca ttaaaattgc agatcagctc actctgaaac tttaagggta    1718
ccagatattt tctatactgc aggatttcta atgacattga agactttta  aacagcctta    1778 gtaaattatc tttctaatgc tctgtgaggc caaacattta tgttcagatt gaaatttaaa    1838
ttaatatcat tcaaaaggaa acaaaaatg  ttgagttta  aaaatcagga ttgactttt     1898 tctccaaaac catacattta taggcaaatt gtgttcttta tcacttctga gcaaatactc    1958
agatttaaaa ttactttaaa gtcctggtac ttaacaggct aacgtagata aacaccttaa    2018
taatctcagt taatactgta tttcaaaaca catttaactg ttttctaatg ctttgcatta    2078
tcagttacaa cctagagaga ttttgagcct catatttctt tgatacttga aatagaggga    2138 gctagaaacac ttaatgttta atctgttaaa cctgctgcaa gagccataac tttgaggcat   2198
tttctaaatg aactgtgggg atccaggatt tgtaatttct tgatctaaac tttatgctgc    2258
ataaatcact tatcggaaat gcacatttca tagtgtgaag cactcatttc taaaccttat    2318
tatctaaggt aatatatgca cctttcagaa atttgtgttc gagtaagtaa agcatattag    2378
aataattatg ggttgacaga ttttaaaat  agaatttaga gtatttgtgt ggggttttgt    2438
ttgtttacaa ataatcagac tataatattt aaacatgcaa ataactgag  aataatgttg    2498 cacttgttta ctaaagatat aagttgttcc atgggtgtac acgtagacag acacacatac    2558
acccaaatta ttgcattaag aatcctggag cagaccatag ctgaagctgt tattttcagt    2618
caggaagact acctgtcatg aaggtataca ataatttaga agtgaatgtt tttctgtacc    2678
atctatgtgc aattatactc taaattccac tacactacat taaagtaaat ggacattcca    2738
gaatatagat gtgattatag tcttaaacta attattaaac caatgattgc tgaaaatcag    2798
tgatgcattt gttatagagt ataactcatc gtttacagta tgttttagtt ggcagtatca    2858
tacctagatg gtgaataaca tattcccagt aaatttatat agcagtgaag aattacatgc    2918
cttctggtgg acattttata agtgcatttt atatcacaat aaaatttttt ctctttacaa    2978
aaaaaaaaaa aga                                                       2991
```

<210> SEQ ID NO 8
<211> LENGTH: 265
<212> TYPE: PRT
<213> ORGANISM: Homo sapiens

<400> SEQUENCE: 8

```
Met Ser His Gln Thr Gly Ile Gln Ala Ser Glu Asp Val Lys Glu Ile
1               5                   10                  15

Phe Ala Arg Ala Arg Asn Gly Lys Tyr Arg Leu Leu Lys Ile Ser Ile
            20                  25                  30

Glu Asn Glu Gln Leu Val Ile Gly Ser Tyr Ser Gln Pro Ser Asp Ser
```

```
                  35                  40                  45
Trp Asp Lys Asp Tyr Asp Ser Phe Val Leu Pro Leu Leu Glu Asp Lys
 50                  55                  60

Gln Pro Cys Tyr Ile Leu Phe Arg Leu Asp Ser Gln Asn Ala Gln Gly
 65                  70                  75                  80

Tyr Glu Trp Ile Phe Ile Ala Trp Ser Pro Asp His Ser His Val Arg
                 85                  90                  95

Gln Lys Met Leu Tyr Ala Ala Thr Arg Ala Thr Leu Lys Lys Glu Phe
            100                 105                 110

Gly Gly Gly His Ile Lys Asp Glu Ile Phe Gly Thr Val Lys Glu Asp
            115                 120                 125

Val Ser Leu His Gly Tyr Lys Lys Tyr Leu Ser Gln Ser Ser Pro
130                 135                 140

Ala Pro Leu Thr Ala Ala Glu Glu Leu Arg Gln Ile Lys Ile Asn
145                 150                 155                 160

Glu Val Gln Thr Asp Val Gly Val Asp Thr Lys His Gln Thr Leu Gln
                165                 170                 175

Gly Val Ala Phe Pro Ile Ser Arg Glu Ala Phe Gln Ala Leu Glu Lys
            180                 185                 190

Leu Asn Asn Arg Gln Leu Asn Tyr Val Gln Leu Glu Ile Asp Ile Lys
            195                 200                 205

Asn Glu Ile Ile Ile Leu Ala Asn Thr Thr Asn Thr Glu Leu Lys Asp
            210                 215                 220

Leu Pro Lys Arg Ile Pro Lys Asp Ser Ala Arg Tyr His Phe Phe Leu
225                 230                 235                 240

Tyr Lys His Ser His Glu Gly Asp Tyr Leu Glu Ser Ile Val Leu Phe
                245                 250                 255

Ile Gln Cys Leu Asp Thr His Ala Val
            260                 265

<210> SEQ ID NO 9
<211> LENGTH: 4231
<212> TYPE: DNA
<213> ORGANISM: Homo sapiens
<220> FEATURE:
<221> NAME/KEY: CDS
<222> LOCATION: (116)..(4093)
<223> OTHER INFORMATION:

<400> SEQUENCE: 9
ggacaggcgt ggcggccgga gccccagcat ccctgcttga gtccaggag cggagcccgc        60 ggccaccgcc gcctgatcag cgcgaccccg gcccgcgccc gccccgcccg gcaag atg      118
                                                              Met
                                                               1 ctg ccc gtg tac cag gag gtg aag ccc aac ccg ctg cag gac gcg aac      166
Leu Pro Val Tyr Gln Glu Val Lys Pro Asn Pro Leu Gln Asp Ala Asn
           5                  10                  15 atc tgc tca cgc gtg ttc ttc tgg tgg ctc aat ccc ttg ttt aaa att      214
Ile Cys Ser Arg Val Phe Phe Trp Trp Leu Asn Pro Leu Phe Lys Ile
         20                  25                  30 ggc cat aaa cgg aga tta gag gaa gat gat atg tat tca gtg ctg cca      262
Gly His Lys Arg Arg Leu Glu Glu Asp Asp Met Tyr Ser Val Leu Pro
 35                  40                  45 gaa gac cgc tca cag cac ctt gga gag gag ttg caa ggg ttc tgg gat      310
Glu Asp Arg Ser Gln His Leu Gly Glu Glu Leu Gln Gly Phe Trp Asp
 50                  55                  60                  65 aaa gaa gtt tta aga gct gag aat gac gca cag aag cct tct tta aca      358
```

```
Lys Glu Val Leu Arg Ala Glu Asn Asp Ala Gln Lys Pro Ser Leu Thr
                70              75              80 aga gca atc ata aag tgt tac tgg aaa tct tat tta gtt ttg gga att    406
Arg Ala Ile Ile Lys Cys Tyr Trp Lys Ser Tyr Leu Val Leu Gly Ile
            85              90              95 ttt acg tta att gag gaa agt gcc aaa gta atc cag ccc ata ttt ttg    454
Phe Thr Leu Ile Glu Glu Ser Ala Lys Val Ile Gln Pro Ile Phe Leu
        100             105             110 gga aaa att att aat tat ttt gaa aat tat gat ccc atg gat tct gtg    502
Gly Lys Ile Ile Asn Tyr Phe Glu Asn Tyr Asp Pro Met Asp Ser Val
    115             120             125 gct ttg aac aca gcg tac gcc tat gcc acg gtg ctg act ttt tgc acg    550
Ala Leu Asn Thr Ala Tyr Ala Tyr Ala Thr Val Leu Thr Phe Cys Thr
130             135             140             145 ctc att ttg gct ata ctg cat cac tta tat ttt tat cac gtt cag tgt    598
Leu Ile Leu Ala Ile Leu His His Leu Tyr Phe Tyr His Val Gln Cys
            150             155             160 gct ggg atg agg tta cga gta gcc atg tgc cat atg att tat cgg aag    646
Ala Gly Met Arg Leu Arg Val Ala Met Cys His Met Ile Tyr Arg Lys
        165             170             175 gca ctt cgt ctt agt aac atg gcc atg ggg aag aca acc aca ggc cag    694
Ala Leu Arg Leu Ser Asn Met Ala Met Gly Lys Thr Thr Thr Gly Gln
    180             185             190 ata gtc aat ctg ctg tcc aat gat gtg aac aag ttt gat cag gtg aca    742
Ile Val Asn Leu Leu Ser Asn Asp Val Asn Lys Phe Asp Gln Val Thr
195             200             205 gtg ttc tta cac ttc ctg tgg gca gga cca ctg cag gcg atc gca gtg    790
Val Phe Leu His Phe Leu Trp Ala Gly Pro Leu Gln Ala Ile Ala Val
210             215             220             225 act gcc cta ctc tgg atg gag ata gga ata tcg tgc ctt gct ggg atg    838
Thr Ala Leu Leu Trp Met Glu Ile Gly Ile Ser Cys Leu Ala Gly Met
            230             235             240 gca gtt cta atc att ctc ctg ccc ttg caa agc tgt ttt ggg aag ttg    886
Ala Val Leu Ile Ile Leu Leu Pro Leu Gln Ser Cys Phe Gly Lys Leu
        245             250             255 ttc tca tca ctg agg agt aaa act gca act ttc acg gat gcc agg atc    934
Phe Ser Ser Leu Arg Ser Lys Thr Ala Thr Phe Thr Asp Ala Arg Ile
    260             265             270 agg acc atg aat gaa gtt ata act ggt ata agg ata ata aaa atg tac    982
Arg Thr Met Asn Glu Val Ile Thr Gly Ile Arg Ile Ile Lys Met Tyr
275             280             285 gcc tgg gaa aag tca ttt tca aat ctt att acc aat ttg aga aag aag    1030
Ala Trp Glu Lys Ser Phe Ser Asn Leu Ile Thr Asn Leu Arg Lys Lys
290             295             300             305 gag att tcc aag att ctg aga agt tcc tgc ctc agg ggg atg aat ttg    1078
Glu Ile Ser Lys Ile Leu Arg Ser Ser Cys Leu Arg Gly Met Asn Leu
            310             315             320 gct tcg ttt ttc agt gca agc aaa atc atc gtg ttt gtg acc ttc acc    1126
Ala Ser Phe Phe Ser Ala Ser Lys Ile Ile Val Phe Val Thr Phe Thr
        325             330             335 acc tac gtg ctc ctc ggc agt gtg atc aca gcc agc cgc gtg ttc gtg    1174
Thr Tyr Val Leu Leu Gly Ser Val Ile Thr Ala Ser Arg Val Phe Val
    340             345             350 gca gtg acg ctg tat ggg gct gtg cgg ctg acg gtt acc ctc ttc ttc    1222
Ala Val Thr Leu Tyr Gly Ala Val Arg Leu Thr Val Thr Leu Phe Phe
355             360             365 ccc tca gcc att gag agg gtg tca gag gca atc gtc agc atc cga aga    1270
Pro Ser Ala Ile Glu Arg Val Ser Glu Ala Ile Val Ser Ile Arg Arg
370             375             380             385
```

-continued

| | |
|---|---|
| atc cag acc ttt ttg cta ctt gat gag ata tca cag cgc aac cgt cag<br>Ile Gln Thr Phe Leu Leu Leu Asp Glu Ile Ser Gln Arg Asn Arg Gln<br>390                                395                      400 | 1318 |
| ctg ccg tca gat ggt aaa aag atg gtg cat gtg cag gat ttt act gct<br>Leu Pro Ser Asp Gly Lys Lys Met Val His Val Gln Asp Phe Thr Ala<br>             405                      410                      415 | 1366 |
| ttt tgg gat aag gca tca gag acc cca act cta caa ggc ctt tcc ttt<br>Phe Trp Asp Lys Ala Ser Glu Thr Pro Thr Leu Gln Gly Leu Ser Phe<br>420                                425                      430 | 1414 |
| act gtc aga cct ggc gaa ttg tta gct gtg gtc ggc ccc gtg gga gca<br>Thr Val Arg Pro Gly Glu Leu Leu Ala Val Val Gly Pro Val Gly Ala<br>             435                      440                      445 | 1462 |
| ggg aag tca tca ctg tta agt gcc gtg ctc ggg gaa ttg gcc cca agt<br>Gly Lys Ser Ser Leu Leu Ser Ala Val Leu Gly Glu Leu Ala Pro Ser<br>450                                455                      460                      465 | 1510 |
| cac ggg ctg gtc agc gtg cat gga aga att gcc tat gtg tct cag cag<br>His Gly Leu Val Ser Val His Gly Arg Ile Ala Tyr Val Ser Gln Gln<br>             470                      475                      480 | 1558 |
| ccc tgg gtg ttc tcg gga act ctg agg agt aat att tta ttt ggg aag<br>Pro Trp Val Phe Ser Gly Thr Leu Arg Ser Asn Ile Leu Phe Gly Lys<br>485                                490                      495 | 1606 |
| aaa tat gaa aag gaa cga tat gaa aaa gtc ata aag gct tgt gct ctg<br>Lys Tyr Glu Lys Glu Arg Tyr Glu Lys Val Ile Lys Ala Cys Ala Leu<br>             500                      505                      510 | 1654 |
| aaa aag gat tta cag ctg ttg gag gat ggt gat ctg act gtg ata gga<br>Lys Lys Asp Leu Gln Leu Leu Glu Asp Gly Asp Leu Thr Val Ile Gly<br>515                                520                      525 | 1702 |
| gat cgg gga acc acg ctg agt gga ggg cag aaa gca cgg gta aac ctt<br>Asp Arg Gly Thr Thr Leu Ser Gly Gly Gln Lys Ala Arg Val Asn Leu<br>530                                535                      540                      545 | 1750 |
| gca aga gca gtg tat caa gat gct gac atc tat ctc ctg gac gat cct<br>Ala Arg Ala Val Tyr Gln Asp Ala Asp Ile Tyr Leu Leu Asp Asp Pro<br>             550                      555                      560 | 1798 |
| ctc agt gca gta gat gcg gaa gtt agc aga cac ttg ttc gaa ctg tgt<br>Leu Ser Ala Val Asp Ala Glu Val Ser Arg His Leu Phe Glu Leu Cys<br>             565                      570                      575 | 1846 |
| att tgt caa att ttg cat gag aag atc aca att tta gtg act cat cag<br>Ile Cys Gln Ile Leu His Glu Lys Ile Thr Ile Leu Val Thr His Gln<br>                  580                      585                      590 | 1894 |
| ttg cag tac ctc aaa gct gca agt cag att ctg ata ttg aaa gat ggt<br>Leu Gln Tyr Leu Lys Ala Ala Ser Gln Ile Leu Ile Leu Lys Asp Gly<br>595                                600                      605 | 1942 |
| aaa atg gtg cag aag ggg act tac act gag ttc cta aaa tct ggt ata<br>Lys Met Val Gln Lys Gly Thr Tyr Thr Glu Phe Leu Lys Ser Gly Ile<br>610                                615                      620                      625 | 1990 |
| gat ttt ggc tcc ctt tta aag aag gat aat gag gaa agt gaa caa cct<br>Asp Phe Gly Ser Leu Leu Lys Lys Asp Asn Glu Glu Ser Glu Gln Pro<br>             630                      635                      640 | 2038 |
| cca gtt cca gga act ccc aca cta agg aat cgt acc ttc tca gag tct<br>Pro Val Pro Gly Thr Pro Thr Leu Arg Asn Arg Thr Phe Ser Glu Ser<br>             645                      650                      655 | 2086 |
| tcg gtt tgg tct caa caa tct tct aga ccc tcc ttg aaa gat ggt gct<br>Ser Val Trp Ser Gln Gln Ser Ser Arg Pro Ser Leu Lys Asp Gly Ala<br>             660                      665                      670 | 2134 |
| ctg gag agc caa gat aca gag aat gtc cca gtt aca cta tca gag gag<br>Leu Glu Ser Gln Asp Thr Glu Asn Val Pro Val Thr Leu Ser Glu Glu<br>675                                680                      685 | 2182 |
| aac cgt tct gaa gga aaa gtt ggt ttt cag gcc tat aag aat tac ttc<br>Asn Arg Ser Glu Gly Lys Val Gly Phe Gln Ala Tyr Lys Asn Tyr Phe<br>690                                695                      700                      705 | 2230 |

```
aga gct ggt gct cac tgg att gtc ttc att ttc ctt att ctc cta aac    2278
Arg Ala Gly Ala His Trp Ile Val Phe Ile Phe Leu Ile Leu Leu Asn
            710                 715                 720 act gca gct cag gtt gcc tat gtg ctt caa gat tgg tgg ctt tca tac    2326
Thr Ala Ala Gln Val Ala Tyr Val Leu Gln Asp Trp Trp Leu Ser Tyr
            725                 730                 735 tgg gca aac aaa caa agt atg cta aat gtc act gta aat gga gga gga    2374
Trp Ala Asn Lys Gln Ser Met Leu Asn Val Thr Val Asn Gly Gly Gly
            740                 745                 750 aat gta acc gag aag cta gat ctt aac tgg tac tta gga att tat tca    2422
Asn Val Thr Glu Lys Leu Asp Leu Asn Trp Tyr Leu Gly Ile Tyr Ser
755                 760                 765 ggt tta act gta gct acc gtt ctt ttt ggc ata gca aga tct cta ttg    2470
Gly Leu Thr Val Ala Thr Val Leu Phe Gly Ile Ala Arg Ser Leu Leu
770                 775                 780                 785 gta ttc tac gtc ctt gtt aac tct tca caa act ttg cac aac aaa atg    2518
Val Phe Tyr Val Leu Val Asn Ser Ser Gln Thr Leu His Asn Lys Met
                790                 795                 800 ttt gag tca att ctg aaa gct ccg gta tta ttc ttt gat aga aat cca    2566
Phe Glu Ser Ile Leu Lys Ala Pro Val Leu Phe Phe Asp Arg Asn Pro
            805                 810                 815 ata gga aga att tta aat cgt ttc tcc aaa gac att gga cac ttg gat    2614
Ile Gly Arg Ile Leu Asn Arg Phe Ser Lys Asp Ile Gly His Leu Asp
            820                 825                 830 gat ttg ctg ccg ctg acg ttt tta gat ttc atc cag aca ttg cta caa    2662
Asp Leu Leu Pro Leu Thr Phe Leu Asp Phe Ile Gln Thr Leu Leu Gln
835                 840                 845 gtg gtt ggt gtg gtc tct gtg gct gtg gcc gtg att cct tgg atc gca    2710
Val Val Gly Val Val Ser Val Ala Val Ala Val Ile Pro Trp Ile Ala
850                 855                 860                 865 ata ccc ttg gtt ccc ctt gga atc att ttc att ttt ctt cgg cga tat    2758
Ile Pro Leu Val Pro Leu Gly Ile Ile Phe Ile Phe Leu Arg Arg Tyr
                870                 875                 880 ttt ttg gaa acg tca aga gat gtg aag cgc ctg gaa tct aca act cgg    2806
Phe Leu Glu Thr Ser Arg Asp Val Lys Arg Leu Glu Ser Thr Thr Arg
            885                 890                 895 agt cca gtg ttt tcc cac ttg tca tct tct ctc cag ggg ctc tgg acc    2854
Ser Pro Val Phe Ser His Leu Ser Ser Ser Leu Gln Gly Leu Trp Thr
        900                 905                 910 atc cgg gca tac aaa gca gaa gag agg tgt cag gaa ctg ttt gat gca    2902
Ile Arg Ala Tyr Lys Ala Glu Glu Arg Cys Gln Glu Leu Phe Asp Ala
        915                 920                 925 cac cag gat tta cat tca gag gct tgg ttc ttg ttt ttg aca acg tcc    2950
His Gln Asp Leu His Ser Glu Ala Trp Phe Leu Phe Leu Thr Thr Ser
930                 935                 940                 945 cgc tgg ttc gcc gtc cgt ctg gat gcc atc tgt gcc atg ttt gtc atc    2998
Arg Trp Phe Ala Val Arg Leu Asp Ala Ile Cys Ala Met Phe Val Ile
                950                 955                 960 atc gtt gcc ttt ggg tcc ctg att ctg gca aaa act ctg gat gcc ggg    3046
Ile Val Ala Phe Gly Ser Leu Ile Leu Ala Lys Thr Leu Asp Ala Gly
            965                 970                 975 cag gtt ggt ttg gca ctg tcc tat gcc ctc acg ctc atg ggg atg ttt    3094
Gln Val Gly Leu Ala Leu Ser Tyr Ala Leu Thr Leu Met Gly Met Phe
        980                 985                 990 cag tgg tgt gtt cga caa agt  gct gaa gtt gag aat  atg atg atc tca  3142
Gln Trp Cys Val Arg Gln Ser  Ala Glu Val Glu Asn  Met Met Ile Ser
995                 1000                1005 gta  gaa agg gtc att gaa  tac aca gac ctt gaa  aaa gaa gca cct     3187
Val  Glu Arg Val Ile Glu  Tyr Thr Asp Leu Glu  Lys Glu Ala Pro
```

-continued

| | | | | | | | | | | | | | | |
|---|---|---|---|---|---|---|---|---|---|---|---|---|---|---|
| | 1010 | | | | 1015 | | | | 1020 | | | | | |
| tgg | gaa | tat | cag | aaa | cgc | cca | cca | cca | gcc | tgg | ccc | cat | gaa | gga | 3232 |
| Trp | Glu | Tyr | Gln | Lys | Arg | Pro | Pro | Pro | Ala | Trp | Pro | His | Glu | Gly | |
| 1025 | | | | | 1030 | | | | | 1035 | | | | | |
| gtg | ata | atc | ttt | gac | aat | gtg | aac | ttc | atg | tac | agt | cca | ggt | ggg | 3277 |
| Val | Ile | Ile | Phe | Asp | Asn | Val | Asn | Phe | Met | Tyr | Ser | Pro | Gly | Gly | |
| 1040 | | | | | 1045 | | | | | 1050 | | | | | |
| cct | ctg | gta | ctg | aag | cat | ctg | aca | gca | ctc | att | aaa | tca | caa | gaa | 3322 |
| Pro | Leu | Val | Leu | Lys | His | Leu | Thr | Ala | Leu | Ile | Lys | Ser | Gln | Glu | |
| 1055 | | | | | 1060 | | | | | 1065 | | | | | |
| aag | gtt | ggc | att | gtg | gga | aga | acc | gga | gct | gga | aaa | agt | tcc | ctc | 3367 |
| Lys | Val | Gly | Ile | Val | Gly | Arg | Thr | Gly | Ala | Gly | Lys | Ser | Ser | Leu | |
| 1070 | | | | | 1075 | | | | | 1080 | | | | | |
| atc | tca | gcc | ctt | ttt | aga | ttg | tca | gaa | ccc | gaa | ggt | aaa | att | tgg | 3412 |
| Ile | Ser | Ala | Leu | Phe | Arg | Leu | Ser | Glu | Pro | Glu | Gly | Lys | Ile | Trp | |
| 1085 | | | | | 1090 | | | | | 1095 | | | | | |
| att | gat | aag | atc | ttg | aca | act | gaa | att | gga | ctt | cac | gat | tta | agg | 3457 |
| Ile | Asp | Lys | Ile | Leu | Thr | Thr | Glu | Ile | Gly | Leu | His | Asp | Leu | Arg | |
| 1100 | | | | | 1105 | | | | | 1110 | | | | | |
| aag | aaa | atg | tca | atc | ata | cct | cag | gaa | cct | gtt | ttg | ttc | act | gga | 3502 |
| Lys | Lys | Met | Ser | Ile | Ile | Pro | Gln | Glu | Pro | Val | Leu | Phe | Thr | Gly | |
| 1115 | | | | | 1120 | | | | | 1125 | | | | | |
| aca | atg | agg | aaa | aac | ctg | gat | ccc | ttt | aag | gag | cac | acg | gat | gag | 3547 |
| Thr | Met | Arg | Lys | Asn | Leu | Asp | Pro | Phe | Lys | Glu | His | Thr | Asp | Glu | |
| 1130 | | | | | 1135 | | | | | 1140 | | | | | |
| gaa | ctg | tgg | aat | gcc | tta | caa | gag | gta | caa | ctt | aaa | gaa | acc | att | 3592 |
| Glu | Leu | Trp | Asn | Ala | Leu | Gln | Glu | Val | Gln | Leu | Lys | Glu | Thr | Ile | |
| 1145 | | | | | 1150 | | | | | 1155 | | | | | |
| gaa | gat | ctt | cct | ggt | aaa | atg | gat | act | gaa | tta | gca | gaa | tca | gga | 3637 |
| Glu | Asp | Leu | Pro | Gly | Lys | Met | Asp | Thr | Glu | Leu | Ala | Glu | Ser | Gly | |
| 1160 | | | | | 1165 | | | | | 1170 | | | | | |
| tcc | aat | ttt | agt | gtt | gga | caa | aga | caa | ctg | gtg | tgc | ctt | gcc | agg | 3682 |
| Ser | Asn | Phe | Ser | Val | Gly | Gln | Arg | Gln | Leu | Val | Cys | Leu | Ala | Arg | |
| 1175 | | | | | 1180 | | | | | 1185 | | | | | |
| gca | att | ctc | agg | aaa | aat | cag | ata | ttg | att | att | gat | gaa | gcg | acg | 3727 |
| Ala | Ile | Leu | Arg | Lys | Asn | Gln | Ile | Leu | Ile | Ile | Asp | Glu | Ala | Thr | |
| 1190 | | | | | 1195 | | | | | 1200 | | | | | |
| gca | aat | gtg | gat | cca | aga | act | gat | gag | tta | ata | caa | aaa | aaa | atc | 3772 |
| Ala | Asn | Val | Asp | Pro | Arg | Thr | Asp | Glu | Leu | Ile | Gln | Lys | Lys | Ile | |
| 1205 | | | | | 1210 | | | | | 1215 | | | | | |
| cgg | gag | aaa | ttt | gcc | cac | tgc | acc | gtg | cta | acc | att | gca | cac | aga | 3817 |
| Arg | Glu | Lys | Phe | Ala | His | Cys | Thr | Val | Leu | Thr | Ile | Ala | His | Arg | |
| 1220 | | | | | 1225 | | | | | 1230 | | | | | |
| ttg | aac | acc | att | att | gac | agc | gac | aag | ata | atg | gtt | tta | gat | tca | 3862 |
| Leu | Asn | Thr | Ile | Ile | Asp | Ser | Asp | Lys | Ile | Met | Val | Leu | Asp | Ser | |
| 1235 | | | | | 1240 | | | | | 1245 | | | | | |
| gga | aga | ctg | aaa | gaa | tat | gat | gag | ccg | tat | gtt | ttg | ctg | caa | aat | 3907 |
| Gly | Arg | Leu | Lys | Glu | Tyr | Asp | Glu | Pro | Tyr | Val | Leu | Leu | Gln | Asn | |
| 1250 | | | | | 1255 | | | | | 1260 | | | | | |
| aaa | gag | agc | cta | ttt | tac | aag | atg | gtg | caa | caa | ctg | ggc | aag | gca | 3952 |
| Lys | Glu | Ser | Leu | Phe | Tyr | Lys | Met | Val | Gln | Gln | Leu | Gly | Lys | Ala | |
| 1265 | | | | | 1270 | | | | | 1275 | | | | | |
| gaa | gcc | gct | gcc | ctc | act | gaa | aca | gca | aaa | cag | gta | tac | ttc | aaa | 3997 |
| Glu | Ala | Ala | Ala | Leu | Thr | Glu | Thr | Ala | Lys | Gln | Val | Tyr | Phe | Lys | |
| 1280 | | | | | 1285 | | | | | 1290 | | | | | |
| aga | aat | tat | cca | cat | att | ggt | cac | act | gac | cac | atg | gtt | aca | aac | 4042 |
| Arg | Asn | Tyr | Pro | His | Ile | Gly | His | Thr | Asp | His | Met | Val | Thr | Asn | |
| 1295 | | | | | 1300 | | | | | 1305 | | | | | |
| act | tcc | aat | gga | cag | ccc | tcg | acc | tta | act | att | ttc | gag | aca | gca | 4087 |

```
Thr  Ser  Asn  Gly  Gln  Pro  Ser  Thr  Leu  Thr  Ile  Phe  Glu  Thr  Ala
1310                1315                     1320 ctg  tga atccaaccaa aatgtcaagt ccgttccgaa ggcatttttcc actagttttt      4143
Leu
1325 ggactatgta aaccacattg tactttttttt tactttggca acaaatattt atacatacaa   4203 gatgctagtt catttgaata tttctccc                                       4231

<210> SEQ ID NO 10
<211> LENGTH: 1325
<212> TYPE: PRT
<213> ORGANISM: Homo sapiens

<400> SEQUENCE: 10

Met  Leu  Pro  Val  Tyr  Gln  Glu  Val  Lys  Pro  Asn  Pro  Leu  Gln  Asp  Ala
1                 5                        10                      15

Asn  Ile  Cys  Ser  Arg  Val  Phe  Phe  Trp  Trp  Leu  Asn  Pro  Leu  Phe  Lys
             20                      25                      30

Ile  Gly  His  Lys  Arg  Arg  Leu  Glu  Glu  Asp  Asp  Met  Tyr  Ser  Val  Leu
             35                      40                      45

Pro  Glu  Asp  Arg  Ser  Gln  His  Leu  Gly  Glu  Glu  Leu  Gln  Gly  Phe  Trp
50                      55                      60

Asp  Lys  Glu  Val  Leu  Arg  Ala  Glu  Asn  Asp  Ala  Gln  Lys  Pro  Ser  Leu
65                      70                      75                      80

Thr  Arg  Ala  Ile  Ile  Lys  Cys  Tyr  Trp  Lys  Ser  Tyr  Leu  Val  Leu  Gly
                 85                      90                      95

Ile  Phe  Thr  Leu  Ile  Glu  Glu  Ser  Ala  Lys  Val  Ile  Gln  Pro  Ile  Phe
                 100                     105                     110

Leu  Gly  Lys  Ile  Ile  Asn  Tyr  Phe  Glu  Asn  Tyr  Asp  Pro  Met  Asp  Ser
             115                     120                     125

Val  Ala  Leu  Asn  Thr  Ala  Tyr  Ala  Tyr  Ala  Thr  Val  Leu  Thr  Phe  Cys
130                     135                     140

Thr  Leu  Ile  Leu  Ala  Ile  Leu  His  His  Leu  Tyr  Phe  Tyr  His  Val  Gln
145                     150                     155                     160

Cys  Ala  Gly  Met  Arg  Leu  Arg  Val  Ala  Met  Cys  His  Met  Ile  Tyr  Arg
                 165                     170                     175

Lys  Ala  Leu  Arg  Leu  Ser  Asn  Met  Ala  Met  Gly  Lys  Thr  Thr  Thr  Gly
             180                     185                     190

Gln  Ile  Val  Asn  Leu  Leu  Ser  Asn  Asp  Val  Asn  Lys  Phe  Asp  Gln  Val
             195                     200                     205

Thr  Val  Phe  Leu  His  Phe  Leu  Trp  Ala  Gly  Pro  Leu  Gln  Ala  Ile  Ala
210                     215                     220

Val  Thr  Ala  Leu  Leu  Trp  Met  Glu  Ile  Gly  Ile  Ser  Cys  Leu  Ala  Gly
225                     230                     235                     240

Met  Ala  Val  Leu  Ile  Ile  Leu  Leu  Pro  Leu  Gln  Ser  Cys  Phe  Gly  Lys
                 245                     250                     255

Leu  Phe  Ser  Ser  Leu  Arg  Ser  Lys  Thr  Ala  Thr  Phe  Thr  Asp  Ala  Arg
             260                     265                     270

Ile  Arg  Thr  Met  Asn  Glu  Val  Ile  Thr  Gly  Ile  Arg  Ile  Ile  Lys  Met
             275                     280                     285

Tyr  Ala  Trp  Glu  Lys  Ser  Phe  Ser  Asn  Leu  Ile  Thr  Asn  Leu  Arg  Lys
             290                     295                     300

Lys  Glu  Ile  Ser  Lys  Ile  Leu  Arg  Ser  Ser  Cys  Leu  Arg  Gly  Met  Asn
305                     310                     315                     320
```

-continued

```
Leu Ala Ser Phe Phe Ser Ala Ser Lys Ile Ile Val Phe Val Thr Phe
                325                 330                 335

Thr Thr Tyr Val Leu Leu Gly Ser Val Ile Thr Ala Ser Arg Val Phe
            340                 345                 350

Val Ala Val Thr Leu Tyr Gly Ala Val Arg Leu Thr Val Thr Leu Phe
        355                 360                 365

Phe Pro Ser Ala Ile Glu Arg Val Ser Glu Ala Ile Val Ser Ile Arg
    370                 375                 380

Arg Ile Gln Thr Phe Leu Leu Asp Glu Ile Ser Gln Arg Asn Arg
385                 390                 395                 400

Gln Leu Pro Ser Asp Gly Lys Lys Met Val His Val Gln Asp Phe Thr
                405                 410                 415

Ala Phe Trp Asp Lys Ala Ser Glu Thr Pro Thr Leu Gln Gly Leu Ser
            420                 425                 430

Phe Thr Val Arg Pro Gly Glu Leu Leu Ala Val Val Gly Pro Val Gly
        435                 440                 445

Ala Gly Lys Ser Ser Leu Leu Ser Ala Val Leu Gly Glu Leu Ala Pro
    450                 455                 460

Ser His Gly Leu Val Ser Val His Gly Arg Ile Ala Tyr Val Ser Gln
465                 470                 475                 480

Gln Pro Trp Val Phe Ser Gly Thr Leu Arg Ser Asn Ile Leu Phe Gly
                485                 490                 495

Lys Lys Tyr Glu Lys Glu Arg Tyr Glu Lys Val Ile Lys Ala Cys Ala
            500                 505                 510

Leu Lys Lys Asp Leu Gln Leu Leu Glu Asp Gly Asp Leu Thr Val Ile
        515                 520                 525

Gly Asp Arg Gly Thr Thr Leu Ser Gly Gly Gln Lys Ala Arg Val Asn
    530                 535                 540

Leu Ala Arg Ala Val Tyr Gln Asp Ala Asp Ile Tyr Leu Leu Asp Asp
545                 550                 555                 560

Pro Leu Ser Ala Val Asp Ala Glu Val Ser Arg His Leu Phe Glu Leu
                565                 570                 575

Cys Ile Cys Gln Ile Leu His Glu Lys Ile Thr Ile Leu Val Thr His
            580                 585                 590

Gln Leu Gln Tyr Leu Lys Ala Ala Ser Gln Ile Leu Ile Leu Lys Asp
        595                 600                 605

Gly Lys Met Val Gln Lys Gly Thr Tyr Thr Glu Phe Leu Lys Ser Gly
    610                 615                 620

Ile Asp Phe Gly Ser Leu Leu Lys Lys Asp Asn Glu Glu Ser Glu Gln
625                 630                 635                 640

Pro Pro Val Pro Gly Thr Pro Thr Leu Arg Asn Arg Thr Phe Ser Glu
                645                 650                 655

Ser Ser Val Trp Ser Gln Gln Ser Ser Arg Pro Ser Leu Lys Asp Gly
            660                 665                 670

Ala Leu Glu Ser Gln Asp Thr Glu Asn Val Pro Val Thr Leu Ser Glu
        675                 680                 685

Glu Asn Arg Ser Glu Gly Lys Val Gly Phe Gln Ala Tyr Lys Asn Tyr
    690                 695                 700

Phe Arg Ala Gly Ala His Trp Ile Val Phe Ile Phe Leu Ile Leu Leu
705                 710                 715                 720

Asn Thr Ala Ala Gln Val Ala Tyr Val Leu Gln Asp Trp Trp Leu Ser
                725                 730                 735

Tyr Trp Ala Asn Lys Gln Ser Met Leu Asn Val Thr Val Asn Gly Gly
```

-continued

```
                740                 745                 750
Gly Asn Val Thr Glu Lys Leu Asp Leu Asn Trp Tyr Leu Gly Ile Tyr
            755                 760                 765
Ser Gly Leu Thr Val Ala Thr Val Leu Phe Gly Ile Ala Arg Ser Leu
        770                 775                 780
Leu Val Phe Tyr Val Leu Val Asn Ser Ser Gln Thr Leu His Asn Lys
785                 790                 795                 800
Met Phe Glu Ser Ile Leu Lys Ala Pro Val Leu Phe Phe Asp Arg Asn
                805                 810                 815
Pro Ile Gly Arg Ile Leu Asn Arg Phe Ser Lys Asp Ile Gly His Leu
            820                 825                 830
Asp Asp Leu Leu Pro Leu Thr Phe Leu Asp Phe Ile Gln Thr Leu Leu
        835                 840                 845
Gln Val Val Gly Val Val Ser Val Ala Val Ala Val Ile Pro Trp Ile
    850                 855                 860
Ala Ile Pro Leu Val Pro Leu Gly Ile Ile Phe Ile Phe Leu Arg Arg
865                 870                 875                 880
Tyr Phe Leu Glu Thr Ser Arg Asp Val Lys Arg Leu Glu Ser Thr Thr
                885                 890                 895
Arg Ser Pro Val Phe Ser His Leu Ser Ser Ser Leu Gln Gly Leu Trp
            900                 905                 910
Thr Ile Arg Ala Tyr Lys Ala Glu Glu Arg Cys Gln Glu Leu Phe Asp
        915                 920                 925
Ala His Gln Asp Leu His Ser Glu Ala Trp Phe Leu Phe Leu Thr Thr
    930                 935                 940
Ser Arg Trp Phe Ala Val Arg Leu Asp Ala Ile Cys Ala Met Phe Val
945                 950                 955                 960
Ile Ile Val Ala Phe Gly Ser Leu Ile Leu Ala Lys Thr Leu Asp Ala
                965                 970                 975
Gly Gln Val Gly Leu Ala Leu Ser Tyr Ala Leu Thr Leu Met Gly Met
            980                 985                 990
Phe Gln Trp Cys Val Arg Gln Ser  Ala Glu Val Glu Asn  Met Met Ile
        995                 1000                1005
Ser Val  Glu Arg Val Ile Glu  Tyr Thr Asp Leu Glu  Lys Glu Ala
    1010                1015                1020
Pro Trp  Glu Tyr Gln Lys Arg  Pro Pro Ala Trp  Pro His Glu
    1025                1030                1035
Gly Val  Ile Ile Phe Asp Asn  Val Asn Phe Met Tyr  Ser Pro Gly
    1040                1045                1050
Gly Pro  Leu Val Leu Lys His  Leu Thr Ala Leu Ile  Lys Ser Gln
    1055                1060                1065
Glu Lys  Val Gly Ile Val Gly  Arg Thr Gly Ala Gly  Lys Ser Ser
    1070                1075                1080
Leu Ile  Ser Ala Leu Phe Arg  Leu Ser Glu Pro Glu  Gly Lys Ile
    1085                1090                1095
Trp Ile  Asp Lys Ile Leu Thr  Thr Glu Ile Gly Leu  His Asp Leu
    1100                1105                1110
Arg Lys  Lys Met Ser Ile Ile  Pro Gln Glu Pro Val  Leu Phe Thr
    1115                1120                1125
Gly Thr  Met Arg Lys Asn Leu  Asp Pro Phe Lys Glu  His Thr Asp
    1130                1135                1140
Glu Glu  Leu Trp Asn Ala Leu  Gln Glu Val Gln Leu  Lys Glu Thr
    1145                1150                1155
```

```
Ile Glu Asp Leu Pro Gly Lys Met Asp Thr Leu Ala Glu Ser
    1160                1165                1170

Gly Ser Asn Phe Ser Val Gly Gln Arg Gln Leu Val Cys Leu Ala
    1175                1180                1185

Arg Ala Ile Leu Arg Lys Asn Gln Ile Leu Ile Ile Asp Glu Ala
    1190                1195                1200

Thr Ala Asn Val Asp Pro Arg Thr Asp Glu Leu Ile Gln Lys Lys
    1205                1210                1215

Ile Arg Glu Lys Phe Ala His Cys Thr Val Leu Thr Ile Ala His
    1220                1225                1230

Arg Leu Asn Thr Ile Ile Asp Ser Asp Lys Ile Met Val Leu Asp
    1235                1240                1245

Ser Gly Arg Leu Lys Glu Tyr Asp Glu Pro Tyr Val Leu Leu Gln
    1250                1255                1260

Asn Lys Glu Ser Leu Phe Tyr Lys Met Val Gln Gln Leu Gly Lys
    1265                1270                1275

Ala Glu Ala Ala Ala Leu Thr Glu Thr Ala Lys Gln Val Tyr Phe
    1280                1285                1290

Lys Arg Asn Tyr Pro His Ile Gly His Thr Asp His Met Val Thr
    1295                1300                1305

Asn Thr Ser Asn Gly Gln Pro Ser Thr Leu Thr Ile Phe Glu Thr
    1310                1315                1320

Ala Leu
    1325

<210> SEQ ID NO 11
<211> LENGTH: 3429
<212> TYPE: DNA
<213> ORGANISM: Homo sapiens
<220> FEATURE:
<221> NAME/KEY: CDS
<222> LOCATION: (67)..(2787)
<223> OTHER INFORMATION:

<400> SEQUENCE: 11
gagacaaagc agcgcccgtc tgcttcgggc tctggaatt tagcgctcgc ccagctagcc      60 gcagaa atg act gct gtc cat gca ggc aac ata aac ttc aag tgg gat      108
       Met Thr Ala Val His Ala Gly Asn Ile Asn Phe Lys Trp Asp
         1               5                  10 cct aaa agt cta gag atc agg act ctg gca gtt gag aga ctg ttg gag   156
Pro Lys Ser Leu Glu Ile Arg Thr Leu Ala Val Glu Arg Leu Leu Glu
 15              20                  25                  30 cct ctt gtt aca cag gtt aca acc ctt gta aac acc aat agt aaa ggg   204
Pro Leu Val Thr Gln Val Thr Thr Leu Val Asn Thr Asn Ser Lys Gly
                 35                  40                  45 ccc tct aat aag aag aga ggt cgt tct aag aag gcc cat gtt ttg gct   252
Pro Ser Asn Lys Lys Arg Gly Arg Ser Lys Lys Ala His Val Leu Ala
             50                  55                  60 gca tct gtt gaa caa gca act gag aat ttc ttg gag aag ggg gat aaa   300
Ala Ser Val Glu Gln Ala Thr Glu Asn Phe Leu Glu Lys Gly Asp Lys
         65                  70                  75 att gcg aag gag agc cag ttt ctc aag gag gag ctt gtg gct gct gta   348
Ile Ala Lys Glu Ser Gln Phe Leu Lys Glu Glu Leu Val Ala Ala Val
     80                  85                  90 gaa gat gtt cga aaa caa ggt gat ttg atg aag gct gct gca gga gag   396
Glu Asp Val Arg Lys Gln Gly Asp Leu Met Lys Ala Ala Ala Gly Glu
 95                 100                 105                 110
```

-continued

| | |
|---|---|
| ttc gca gat gat ccc tgc tct tct gtg aag cga ggc aac atg gtt cgg<br>Phe Ala Asp Asp Pro Cys Ser Ser Val Lys Arg Gly Asn Met Val Arg<br>115                       120                   125 | 444 |
| gca gct cga gct ttg ctc tct gct gtt acc cgg ttg ctg att ttg gct<br>Ala Ala Arg Ala Leu Leu Ser Ala Val Thr Arg Leu Leu Ile Leu Ala<br>130                     135                      140 | 492 |
| gac atg gca gat gtc tac aaa tta ctt gtt cag ctg aaa gtt gtg gaa<br>Asp Met Ala Asp Val Tyr Lys Leu Leu Val Gln Leu Lys Val Val Glu<br>145                   150                   155 | 540 |
| gat ggt atc ttg aag ttg agg aat gct ggc aat gaa caa gac tta gga<br>Asp Gly Ile Leu Lys Leu Arg Asn Ala Gly Asn Glu Gln Asp Leu Gly<br>160                   165                   170 | 588 |
| atc cag tat aaa gcc cta aaa cct gaa gtg gat aag ctg aac att atg<br>Ile Gln Tyr Lys Ala Leu Lys Pro Glu Val Asp Lys Leu Asn Ile Met<br>175                   180                   185                   190 | 636 |
| gca gcc aaa aga caa cag gaa ttg aaa gat gtt ggc cat cgt gat cag<br>Ala Ala Lys Arg Gln Gln Glu Leu Lys Asp Val Gly His Arg Asp Gln<br>195                   200                   205 | 684 |
| atg gct gca gct aga gga atc ctg cag aag aac gtt ccg atc ctc tat<br>Met Ala Ala Ala Arg Gly Ile Leu Gln Lys Asn Val Pro Ile Leu Tyr<br>210                   215                   220 | 732 |
| act gca tcc cag gca tgc cta cag cac cct gat gtc gca gcc tat aag<br>Thr Ala Ser Gln Ala Cys Leu Gln His Pro Asp Val Ala Ala Tyr Lys<br>225                   230                   235 | 780 |
| gcc aac agg gac ctg ata tac aag cag ctg cag cag gcg gtc aca ggc<br>Ala Asn Arg Asp Leu Ile Tyr Lys Gln Leu Gln Gln Ala Val Thr Gly<br>240                   245                   250 | 828 |
| att tcc aat gca gcc cag gcc act gcc tca gac gat gcc tca cag cac<br>Ile Ser Asn Ala Ala Gln Ala Thr Ala Ser Asp Asp Ala Ser Gln His<br>255                   260                   265                   270 | 876 |
| cag ggt gga gga gga gga gaa ctg gca tat gca ctc aat aac ttt gac<br>Gln Gly Gly Gly Gly Gly Glu Leu Ala Tyr Ala Leu Asn Asn Phe Asp<br>275                   280                   285 | 924 |
| aaa caa atc att gtg gac ccc ttg agc ttc agc gag gag cgc ttt agg<br>Lys Gln Ile Ile Val Asp Pro Leu Ser Phe Ser Glu Glu Arg Phe Arg<br>290                   295                   300 | 972 |
| cct tcc ctg gag gag cgt ctg gaa agc atc att agt ggg gct gcc ttg<br>Pro Ser Leu Glu Glu Arg Leu Glu Ser Ile Ile Ser Gly Ala Ala Leu<br>305                   310                   315 | 1020 |
| atg gcc gac tcg tcc tgc acg cgt gat gac cgt cgt gag cga att gtg<br>Met Ala Asp Ser Ser Cys Thr Arg Asp Asp Arg Arg Glu Arg Ile Val<br>320                   325                   330 | 1068 |
| gca gag tgt aat gct gtc cgc cag gcc ctg cag gac ctg ctt tcg gag<br>Ala Glu Cys Asn Ala Val Arg Gln Ala Leu Gln Asp Leu Leu Ser Glu<br>335                   340                   345                   350 | 1116 |
| tac atg ggc aat gct gga cgt aaa gaa aga agt gat gca ctc aat tct<br>Tyr Met Gly Asn Ala Gly Arg Lys Glu Arg Ser Asp Ala Leu Asn Ser<br>355                   360                   365 | 1164 |
| gca ata gat aaa atg acc aag aag acc agg gac ttg cgt aga cag ctc<br>Ala Ile Asp Lys Met Thr Lys Lys Thr Arg Asp Leu Arg Arg Gln Leu<br>370                   375                   380 | 1212 |
| cgc aaa gct gtc atg gac cac gtt tca gat tct ttc ctg gaa acc aat<br>Arg Lys Ala Val Met Asp His Val Ser Asp Ser Phe Leu Glu Thr Asn<br>385                   390                   395 | 1260 |
| gtt cca ctt ttg gta ttg att gaa gct gca aag aat gga aat gag aaa<br>Val Pro Leu Leu Val Leu Ile Glu Ala Ala Lys Asn Gly Asn Glu Lys<br>400                   405                   410 | 1308 |
| gaa gtt aag gag tat gcc caa gtt ttc cgt gaa cat gcc aac aaa ttg<br>Glu Val Lys Glu Tyr Ala Gln Val Phe Arg Glu His Ala Asn Lys Leu<br>415                   420                   425                   430 | 1356 |

-continued

```
att gag gtt gcc aac ttg gcc tgt tcc atc tca aat aat gaa gaa ggt    1404
Ile Glu Val Ala Asn Leu Ala Cys Ser Ile Ser Asn Asn Glu Glu Gly
            435                 440                 445 gta aag ctt gtt cga atg tct gca agc cag tta gaa gcc ctc tgt cct    1452
Val Lys Leu Val Arg Met Ser Ala Ser Gln Leu Glu Ala Leu Cys Pro
        450                 455                 460 cag gtt att aat gct gca ctg gct tta gca gca aaa cca cag agt aaa    1500
Gln Val Ile Asn Ala Ala Leu Ala Leu Ala Ala Lys Pro Gln Ser Lys
    465                 470                 475 ctg gcc caa gag aac atg gat ctt ttt aaa gaa caa tgg gaa aaa caa    1548
Leu Ala Gln Glu Asn Met Asp Leu Phe Lys Glu Gln Trp Glu Lys Gln
480                 485                 490 gtc cgt gtt ctc aca gat gct gtc gat gac att act tcc att gat gac    1596
Val Arg Val Leu Thr Asp Ala Val Asp Asp Ile Thr Ser Ile Asp Asp
495                 500                 505                 510 ttc ttg gct gtc tca gag aat cac att ttg gaa gat gtg aac aaa tgt    1644
Phe Leu Ala Val Ser Glu Asn His Ile Leu Glu Asp Val Asn Lys Cys
                515                 520                 525 gtc att gct ctc caa gag aag gat gtg gat ggc ctg gac cgc aca gct    1692
Val Ile Ala Leu Gln Glu Lys Asp Val Asp Gly Leu Asp Arg Thr Ala
            530                 535                 540 ggt gca att cga ggc cgg gca gcc cgg gtc att cac gta gtc acc tca    1740
Gly Ala Ile Arg Gly Arg Ala Ala Arg Val Ile His Val Val Thr Ser
        545                 550                 555 gag atg gac aac tat gag cca gga gtc tac aca gag aag gtt ctg gaa    1788
Glu Met Asp Asn Tyr Glu Pro Gly Val Tyr Thr Glu Lys Val Leu Glu
    560                 565                 570 gcc act aag ctg ctc tcc aac aca gtc atg cca cgt ttt act gag caa    1836
Ala Thr Lys Leu Leu Ser Asn Thr Val Met Pro Arg Phe Thr Glu Gln
575                 580                 585                 590 gta gaa gca gcc gtg gaa gcc ctc agc tcg gac cct gcc cag ccc atg    1884
Val Glu Ala Ala Val Glu Ala Leu Ser Ser Asp Pro Ala Gln Pro Met
                595                 600                 605 gat gag aat gag ttt atc gat gct tcc cgc ctg gta tat gat ggc atc    1932
Asp Glu Asn Glu Phe Ile Asp Ala Ser Arg Leu Val Tyr Asp Gly Ile
            610                 615                 620 cgg gac atc agg aaa gca gtg ctg atg ata agg acc cct gag gag ttg    1980
Arg Asp Ile Arg Lys Ala Val Leu Met Ile Arg Thr Pro Glu Glu Leu
        625                 630                 635 gat gac tct gac ttt gag aca gaa gat ttt gat gtc aga agc agg acg    2028
Asp Asp Ser Asp Phe Glu Thr Glu Asp Phe Asp Val Arg Ser Arg Thr
    640                 645                 650 agc gtc cag aca gaa gac gat cag ctg ata gct ggc cag agt gcc cgg    2076
Ser Val Gln Thr Glu Asp Asp Gln Leu Ile Ala Gly Gln Ser Ala Arg
655                 660                 665                 670 gcg atc atg gct cag ctt ccc cag gag caa aaa gcg aag att gcg gaa    2124
Ala Ile Met Ala Gln Leu Pro Gln Glu Gln Lys Ala Lys Ile Ala Glu
                675                 680                 685 cag gtg gcc agc ttc cag gaa gaa aag agc aag ctg gat gct gaa gtg    2172
Gln Val Ala Ser Phe Gln Glu Glu Lys Ser Lys Leu Asp Ala Glu Val
            690                 695                 700 tcc aaa tgg gac gac agt ggc aat gac atc att gtg ctg gcc aag cag    2220
Ser Lys Trp Asp Asp Ser Gly Asn Asp Ile Ile Val Leu Ala Lys Gln
        705                 710                 715 atg tgc atg att atg atg gag atg aca gac ttt acc cga ggt aaa gga    2268
Met Cys Met Ile Met Met Glu Met Thr Asp Phe Thr Arg Gly Lys Gly
    720                 725                 730 cca ctc aaa aat aca tcg gat gtc atc agt gct gcc aag aaa att gct    2316
Pro Leu Lys Asn Thr Ser Asp Val Ile Ser Ala Ala Lys Lys Ile Ala
```

```
                735                 740                 745                 750
gag gca gga tcc agg atg gac aag ctt ggc cgc acc att gca gac cat      2364
Glu Ala Gly Ser Arg Met Asp Lys Leu Gly Arg Thr Ile Ala Asp His
                755                 760                 765 tgc ccc gac tcg gct tgc aag cag gac ctg ctg gcc tac ctg caa cgc      2412
Cys Pro Asp Ser Ala Cys Lys Gln Asp Leu Leu Ala Tyr Leu Gln Arg
            770                 775                 780 atc gcc ctc tac tgc cac cag ctg aac atc tgc agc aag gtc aag gcc      2460
Ile Ala Leu Tyr Cys His Gln Leu Asn Ile Cys Ser Lys Val Lys Ala
            785                 790                 795 gag gtg cag aat ctc ggc ggg gag ctt gtt gtc tct ggg gtg gac agc      2508
Glu Val Gln Asn Leu Gly Gly Glu Leu Val Val Ser Gly Val Asp Ser
        800                 805                 810 gcc atg tcc ctg atc cag gca gcc aag aac ttg atg aat gct gtg gtg      2556
Ala Met Ser Leu Ile Gln Ala Ala Lys Asn Leu Met Asn Ala Val Val
815                 820                 825                 830 cag aca gtg aag gca tcc tac gtc gcc tct acc aaa tac caa aag tca      2604
Gln Thr Val Lys Ala Ser Tyr Val Ala Ser Thr Lys Tyr Gln Lys Ser
                835                 840                 845 cag ggt atg gct tcc ctc aac ctt cct gct gtg tca tgg aag atg aag      2652
Gln Gly Met Ala Ser Leu Asn Leu Pro Ala Val Ser Trp Lys Met Lys
            850                 855                 860 gca cca gag aaa aag cca ttg gtg aag aga gag aaa cag gat gag aca      2700
Ala Pro Glu Lys Lys Pro Leu Val Lys Arg Glu Lys Gln Asp Glu Thr
            865                 870                 875 cag acc aag att aaa cgg gca tct cag aag aag cac gtg aac ccg gtg      2748
Gln Thr Lys Ile Lys Arg Ala Ser Gln Lys Lys His Val Asn Pro Val
        880                 885                 890 cag gcc ctc agc gag ttc aaa gct atg gac agc atc taa gtctgcccag       2797
Gln Ala Leu Ser Glu Phe Lys Ala Met Asp Ser Ile
895                 900                 905 gccggccgcc cccacccctc ggggctcctg aatatcagtc actgttcgtc actcaaatga    2857
atttgctaaa tacaacactg atactagatt ccacagggaa atgggcagac tgaaccagtc    2917
caggtggtga attttccaag aacatagttt aagttgatta aaaatgcttt tagaatgcag    2977
gagcctactt ctagctgtat tttttgtatg cttaaataaa aataaaaatt cataaccaaa    3037
gagaatccca cattagcttg ttagtaatgc tctgaccaag ccgagatgcc cattctctta    3097
gtgatggcgg cgttagggtt tgagagaagg gaatttggct caacttcagt tgagagggtg    3157
cagtccagac agcttgactg cttttaaatg accaaagatg acctgtggta agcaacctgg    3217
gcatcttaga agcagtccct ggagaaggca tgttcccaga aaggtctctg gagggacaaa    3277
ctcactcagt aaaacataat gtatcatcat gaagaaaact gattctctat gacatgaaat    3337
gaaaatttta atgcattgtt ataattacta atgtacgctg ctgcaggaca ttaataaagt    3397 tgcttttta ggctacagtg tctcgatgcc at                                   3429
```

<210> SEQ ID NO 12
<211> LENGTH: 906
<212> TYPE: PRT
<213> ORGANISM: Homo sapiens

<400> SEQUENCE: 12

```
Met Thr Ala Val His Ala Gly Asn Ile Asn Phe Lys Trp Asp Pro Lys
1               5                   10                  15

Ser Leu Glu Ile Arg Thr Leu Ala Val Glu Arg Leu Leu Glu Pro Leu
            20                  25                  30

Val Thr Gln Val Thr Thr Leu Val Asn Thr Asn Ser Lys Gly Pro Ser
```

```
                35                  40                  45
Asn Lys Lys Arg Gly Arg Ser Lys Lys Ala His Val Leu Ala Ala Ser
 50                  55                  60

Val Glu Gln Ala Thr Glu Asn Phe Leu Glu Lys Gly Asp Lys Ile Ala
 65                  70                  75                  80

Lys Glu Ser Gln Phe Leu Lys Glu Glu Leu Val Ala Ala Val Glu Asp
                 85                  90                  95

Val Arg Lys Gln Gly Asp Leu Met Lys Ala Ala Gly Glu Phe Ala
                100                 105                 110

Asp Asp Pro Cys Ser Ser Val Lys Arg Gly Asn Met Val Arg Ala Ala
                115                 120                 125

Arg Ala Leu Leu Ser Ala Val Thr Arg Leu Leu Ile Leu Ala Asp Met
130                 135                 140

Ala Asp Val Tyr Lys Leu Leu Val Gln Leu Lys Val Val Glu Asp Gly
145                 150                 155                 160

Ile Leu Lys Leu Arg Asn Ala Gly Asn Glu Gln Asp Leu Gly Ile Gln
                165                 170                 175

Tyr Lys Ala Leu Lys Pro Glu Val Asp Lys Leu Asn Ile Met Ala Ala
                180                 185                 190

Lys Arg Gln Gln Glu Leu Lys Asp Val Gly His Arg Asp Gln Met Ala
                195                 200                 205

Ala Ala Arg Gly Ile Leu Gln Lys Asn Val Pro Ile Leu Tyr Thr Ala
210                 215                 220

Ser Gln Ala Cys Leu Gln His Pro Asp Val Ala Ala Tyr Lys Ala Asn
225                 230                 235                 240

Arg Asp Leu Ile Tyr Lys Gln Leu Gln Gln Ala Val Thr Gly Ile Ser
                245                 250                 255

Asn Ala Ala Gln Ala Thr Ala Ser Asp Asp Ala Ser Gln His Gln Gly
                260                 265                 270

Gly Gly Gly Gly Glu Leu Ala Tyr Ala Leu Asn Asn Phe Asp Lys Gln
                275                 280                 285

Ile Ile Val Asp Pro Leu Ser Phe Ser Glu Glu Arg Phe Arg Pro Ser
290                 295                 300

Leu Glu Glu Arg Leu Glu Ser Ile Ile Ser Gly Ala Ala Leu Met Ala
305                 310                 315                 320

Asp Ser Ser Cys Thr Arg Asp Asp Arg Arg Glu Arg Ile Val Ala Glu
                325                 330                 335

Cys Asn Ala Val Arg Gln Ala Leu Gln Asp Leu Leu Ser Glu Tyr Met
                340                 345                 350

Gly Asn Ala Gly Arg Lys Glu Arg Ser Asp Ala Leu Asn Ser Ala Ile
                355                 360                 365

Asp Lys Met Thr Lys Lys Thr Arg Asp Leu Arg Arg Gln Leu Arg Lys
                370                 375                 380

Ala Val Met Asp His Val Ser Asp Ser Phe Leu Glu Thr Asn Val Pro
385                 390                 395                 400

Leu Leu Val Leu Ile Glu Ala Ala Lys Asn Gly Asn Glu Lys Glu Val
                405                 410                 415

Lys Glu Tyr Ala Gln Val Phe Arg Glu His Ala Asn Lys Leu Ile Glu
                420                 425                 430

Val Ala Asn Leu Ala Cys Ser Ile Ser Asn Asn Glu Glu Gly Val Lys
                435                 440                 445

Leu Val Arg Met Ser Ala Ser Gln Leu Glu Ala Leu Cys Pro Gln Val
450                 455                 460
```

```
Ile Asn Ala Ala Leu Ala Leu Ala Ala Lys Pro Gln Ser Lys Leu Ala
465                 470                 475                 480

Gln Glu Asn Met Asp Leu Phe Lys Glu Gln Trp Glu Lys Gln Val Arg
            485                 490                 495

Val Leu Thr Asp Ala Val Asp Asp Ile Thr Ser Ile Asp Asp Phe Leu
            500                 505                 510

Ala Val Ser Glu Asn His Ile Leu Glu Asp Val Asn Lys Cys Val Ile
            515                 520                 525

Ala Leu Gln Glu Lys Asp Val Asp Gly Leu Asp Arg Thr Ala Gly Ala
        530                 535                 540

Ile Arg Gly Arg Ala Ala Arg Val Ile His Val Val Thr Ser Glu Met
545                 550                 555                 560

Asp Asn Tyr Glu Pro Gly Val Tyr Thr Glu Lys Val Leu Glu Ala Thr
            565                 570                 575

Lys Leu Leu Ser Asn Thr Val Met Pro Arg Phe Thr Glu Gln Val Glu
            580                 585                 590

Ala Ala Val Glu Ala Leu Ser Ser Asp Pro Ala Gln Pro Met Asp Glu
        595                 600                 605

Asn Glu Phe Ile Asp Ala Ser Arg Leu Val Tyr Asp Gly Ile Arg Asp
        610                 615                 620

Ile Arg Lys Ala Val Leu Met Ile Arg Thr Pro Glu Glu Leu Asp Asp
625                 630                 635                 640

Ser Asp Phe Glu Thr Glu Asp Phe Asp Val Arg Ser Arg Thr Ser Val
            645                 650                 655

Gln Thr Glu Asp Asp Gln Leu Ile Ala Gly Gln Ser Ala Arg Ala Ile
            660                 665                 670

Met Ala Gln Leu Pro Gln Glu Gln Lys Ala Lys Ile Ala Glu Gln Val
        675                 680                 685

Ala Ser Phe Gln Glu Glu Lys Ser Lys Leu Asp Ala Glu Val Ser Lys
        690                 695                 700

Trp Asp Asp Ser Gly Asn Asp Ile Ile Val Leu Ala Lys Gln Met Cys
705                 710                 715                 720

Met Ile Met Met Glu Met Thr Asp Phe Thr Arg Gly Lys Gly Pro Leu
            725                 730                 735

Lys Asn Thr Ser Asp Val Ile Ser Ala Ala Lys Lys Ile Ala Glu Ala
            740                 745                 750

Gly Ser Arg Met Asp Lys Leu Gly Arg Thr Ile Ala Asp His Cys Pro
        755                 760                 765

Asp Ser Ala Cys Lys Gln Asp Leu Leu Ala Tyr Leu Gln Arg Ile Ala
        770                 775                 780

Leu Tyr Cys His Gln Leu Asn Ile Cys Ser Lys Val Lys Ala Glu Val
785                 790                 795                 800

Gln Asn Leu Gly Gly Glu Leu Val Val Ser Gly Val Asp Ser Ala Met
            805                 810                 815

Ser Leu Ile Gln Ala Ala Lys Asn Leu Met Asn Ala Val Val Gln Thr
            820                 825                 830

Val Lys Ala Ser Tyr Val Ala Ser Thr Lys Tyr Gln Lys Ser Gln Gly
        835                 840                 845

Met Ala Ser Leu Asn Leu Pro Ala Val Ser Trp Lys Met Lys Ala Pro
        850                 855                 860

Glu Lys Lys Pro Leu Val Lys Arg Glu Lys Gln Asp Glu Thr Gln Thr
865                 870                 875                 880
```

```
Lys Ile Lys Arg Ala Ser Gln Lys Lys His Val Asn Pro Val Gln Ala
                885                 890                 895

Leu Ser Glu Phe Lys Ala Met Asp Ser Ile
            900                 905

<210> SEQ ID NO 13
<211> LENGTH: 5298
<212> TYPE: DNA
<213> ORGANISM: Homo sapiens
<220> FEATURE:
<221> NAME/KEY: CDS
<222> LOCATION: (143)..(4819)
<223> OTHER INFORMATION:

<400> SEQUENCE: 13
aagatggccg cggcgcgcac ggctcctgcg gcggggtaga ggcggaggcg gagtcgagtc      60
actcccgcac ttcggggctc cggtgccccg cgccaggctg cagcttactg cccgccgcgg    120
ccatgcgggg ctccgtgcac gg atg aga gaa gcc gct gcc gcg ctg gtc cct    172
                         Met Arg Glu Ala Ala Ala Ala Leu Val Pro
                           1               5                  10 cct ccc gcc ttt gcc gtc acg cct gcc gcc gcc atg gag gag ccg ccg    220
Pro Pro Ala Phe Ala Val Thr Pro Ala Ala Ala Met Glu Glu Pro Pro
             15                  20                  25 cca ccg ccg ccg ccg cca cca ccg cca ccg gaa ccc gag acc gag tca    268
Pro Pro Pro Pro Pro Pro Pro Pro Pro Pro Glu Pro Glu Thr Glu Ser
         30                  35                  40 gaa ccc gag tgc tgc ttg gcg gcg agg caa gag ggc aca ttg gga gat    316
Glu Pro Glu Cys Cys Leu Ala Ala Arg Gln Glu Gly Thr Leu Gly Asp
     45                  50                  55 tca gct tgc aag agt cct gaa tct gat cta gaa gac ttc tcc gat gaa    364
Ser Ala Cys Lys Ser Pro Glu Ser Asp Leu Glu Asp Phe Ser Asp Glu
 60                  65                  70 aca aat aca gag aat ctt tat ggt acc tct ccc ccc agc aca cct cga    412
Thr Asn Thr Glu Asn Leu Tyr Gly Thr Ser Pro Pro Ser Thr Pro Arg
 75                  80                  85                  90 cag atg aaa cgc atg tca acc aaa cat cag agg aat aat gtg ggg agg    460
Gln Met Lys Arg Met Ser Thr Lys His Gln Arg Asn Asn Val Gly Arg
                 95                 100                 105 cca gcc agt cgg tct aat ttg aaa gaa aaa atg aat gca cca aat cag    508
Pro Ala Ser Arg Ser Asn Leu Lys Glu Lys Met Asn Ala Pro Asn Gln
            110                 115                 120 cct cca cat aaa gac act gga aaa aca gtg gag aat gtg gaa gaa tac    556
Pro Pro His Lys Asp Thr Gly Lys Thr Val Glu Asn Val Glu Glu Tyr
        125                 130                 135 agc tat aag cag gag aaa aag atc cga gca gct ctt aga aca aca gag    604
Ser Tyr Lys Gln Glu Lys Lys Ile Arg Ala Ala Leu Arg Thr Thr Glu
    140                 145                 150 cgt gat cgt aaa aaa aat gta cag tgc tca ttc atg tta gac tca gtg    652
Arg Asp Arg Lys Lys Asn Val Gln Cys Ser Phe Met Leu Asp Ser Val
155                 160                 165                 170 ggt gga tct ttg cca aaa aaa tca att cca gat gtg gat ctc aat aag    700
Gly Gly Ser Leu Pro Lys Lys Ser Ile Pro Asp Val Asp Leu Asn Lys
                175                 180                 185 cct tac ctc agc ctt ggc tgt agc aat gct aag ctt cca gta tct gtg    748
Pro Tyr Leu Ser Leu Gly Cys Ser Asn Ala Lys Leu Pro Val Ser Val
            190                 195                 200 ccc atg cct ata gcc aga cct gca cgc cag act tct agg act gac tgt    796
Pro Met Pro Ile Ala Arg Pro Ala Arg Gln Thr Ser Arg Thr Asp Cys
        205                 210                 215 cca gca gat cgt tta aag ttt ttt gaa act tta cga ctt ttg cta aag    844
```

```
                Pro Ala Asp Arg Leu Lys Phe Phe Glu Thr Leu Arg Leu Leu Leu Lys
                    220                 225                 230 ctt acc tca gtc tca aag aaa aaa gac agg gag caa aga gga caa gaa            892
Leu Thr Ser Val Ser Lys Lys Lys Asp Arg Glu Gln Arg Gly Gln Glu
235                 240                 245                 250 aat acg tct ggt ttc tgg ctt aac cga tct aac gaa ctg atc tgg tta            940
Asn Thr Ser Gly Phe Trp Leu Asn Arg Ser Asn Glu Leu Ile Trp Leu
                    255                 260                 265 gag cta caa gcc tgg cat gca gga cgg aca att aac gac cag gac ttc            988
Glu Leu Gln Ala Trp His Ala Gly Arg Thr Ile Asn Asp Gln Asp Phe
                270                 275                 280 ttt tta tat aca gcc cgt caa gcc atc cca gat att att aat gaa atc           1036
Phe Leu Tyr Thr Ala Arg Gln Ala Ile Pro Asp Ile Ile Asn Glu Ile
            285                 290                 295 ctt act ttc aaa gtc gac tat ggg agc ttc gcc ttt gtt aga gat aga           1084
Leu Thr Phe Lys Val Asp Tyr Gly Ser Phe Ala Phe Val Arg Asp Arg
300                 305                 310 gct ggt ttt aat ggt act tca gta gaa ggg cag tgc aaa gcc act cct           1132
Ala Gly Phe Asn Gly Thr Ser Val Glu Gly Gln Cys Lys Ala Thr Pro
315                 320                 325                 330 gga aca aag att gta ggt tac tca aca cat cat gag cat ctc caa cgc           1180
Gly Thr Lys Ile Val Gly Tyr Ser Thr His His Glu His Leu Gln Arg
                    335                 340                 345 cag agg gtc tca ttt gag cag gta aaa cgg ata atg gag ctg cta gag           1228
Gln Arg Val Ser Phe Glu Gln Val Lys Arg Ile Met Glu Leu Leu Glu
                350                 355                 360 tac ata gaa gca ctt tat cca tca ttg cag gct ctt cag aag gac tat           1276
Tyr Ile Glu Ala Leu Tyr Pro Ser Leu Gln Ala Leu Gln Lys Asp Tyr
            365                 370                 375 gaa aaa tat gct gca aaa gac ttc cag gac agg gtg cag gca ctc tgt           1324
Glu Lys Tyr Ala Ala Lys Asp Phe Gln Asp Arg Val Gln Ala Leu Cys
380                 385                 390 ttg tgg tta aac atc aca aaa gac tta aat cag aaa tta agg att atg           1372
Leu Trp Leu Asn Ile Thr Lys Asp Leu Asn Gln Lys Leu Arg Ile Met
395                 400                 405                 410 ggc act gtt ttg ggc atc aag aat tta tca gac att ggc tgg cca gtg           1420
Gly Thr Val Leu Gly Ile Lys Asn Leu Ser Asp Ile Gly Trp Pro Val
                    415                 420                 425 ttt gaa atc cct tcc cct cga cca tcc aaa ggt aat gag ccg gag tat           1468
Phe Glu Ile Pro Ser Pro Arg Pro Ser Lys Gly Asn Glu Pro Glu Tyr
                430                 435                 440 gag ggt gat gac aca gaa gga gaa tta aag gag ttg gaa agt agt acg           1516
Glu Gly Asp Asp Thr Glu Gly Glu Leu Lys Glu Leu Glu Ser Ser Thr
            445                 450                 455 gat gag agt gaa gaa gaa caa atc tct gat cct agg gta ccg gaa atc           1564
Asp Glu Ser Glu Glu Glu Gln Ile Ser Asp Pro Arg Val Pro Glu Ile
460                 465                 470 aga cag ccc ata gat aac agc ttc gac atc cag tcg cgg gac tgc ata           1612
Arg Gln Pro Ile Asp Asn Ser Phe Asp Ile Gln Ser Arg Asp Cys Ile
475                 480                 485                 490 tcc aag aag ctt gag agg ctc gaa tct gag gat gat tct ctt ggc tgg           1660
Ser Lys Lys Leu Glu Arg Leu Glu Ser Glu Asp Asp Ser Leu Gly Trp
                    495                 500                 505 gga gca cca gac tgg agc aca gaa gca ggc ttt agt aga cat tgt ctg           1708
Gly Ala Pro Asp Trp Ser Thr Glu Ala Gly Phe Ser Arg His Cys Leu
                510                 515                 520 act tct att tat aga cca ttt gta gac aaa gca ctg aag cag atg ggg           1756
Thr Ser Ile Tyr Arg Pro Phe Val Asp Lys Ala Leu Lys Gln Met Gly
            525                 530                 535
```

-continued

| | | |
|---|---|---|
| tta aga aag tta att tta aga ctt cac aag cta atg gat ggt tcc ttg<br>Leu Arg Lys Leu Ile Leu Arg Leu His Lys Leu Met Asp Gly Ser Leu<br>540                           545                       550 | 1804 |
| caa agg gca cgt ata gca ttg gta aag aac gat cgt cca gtg gag ttt<br>Gln Arg Ala Arg Ile Ala Leu Val Lys Asn Asp Arg Pro Val Glu Phe<br>555                           560                       565                570 | 1852 |
| tct gaa ttt cca gat ccc atg tgg ggt tca gat tat gtg cag ttg tca<br>Ser Glu Phe Pro Asp Pro Met Trp Gly Ser Asp Tyr Val Gln Leu Ser<br>                          575                       580                       585 | 1900 |
| agg aca cca cct tca tct gag gag aaa tgc agt gct gtg tcg tgg gag<br>Arg Thr Pro Pro Ser Ser Glu Glu Lys Cys Ser Ala Val Ser Trp Glu<br>         590                       595                       600 | 1948 |
| gag ctg aag gcc atg gat tta cct tca ttc gaa cct gcc ttc cta gtt<br>Glu Leu Lys Ala Met Asp Leu Pro Ser Phe Glu Pro Ala Phe Leu Val<br>605                           610                       615 | 1996 |
| ctc tgc cga gtc ctt ctg aat gtc ata cat gag tgt ctg aag tta aga<br>Leu Cys Arg Val Leu Leu Asn Val Ile His Glu Cys Leu Lys Leu Arg<br>620                           625                       630 | 2044 |
| ttg gag cag aga cct gct gga gaa cca tct ctc ttg agt att aag cag<br>Leu Glu Gln Arg Pro Ala Gly Glu Pro Ser Leu Leu Ser Ile Lys Gln<br>635                           640                       645                650 | 2092 |
| ctg gtg aga gag tgt aag gag gtc ctg aag ggc ggc ctg ctg atg aag<br>Leu Val Arg Glu Cys Lys Glu Val Leu Lys Gly Gly Leu Leu Met Lys<br>                          655                       660                       665 | 2140 |
| cag tac tac cag ttc atg ctg cag gag gtt ctg gag gac ttg gag aag<br>Gln Tyr Tyr Gln Phe Met Leu Gln Glu Val Leu Glu Asp Leu Glu Lys<br>         670                       675                       680 | 2188 |
| ccc gac tgc aac att gac gct ttt gaa gag gat cta cat aaa atg ctt<br>Pro Asp Cys Asn Ile Asp Ala Phe Glu Glu Asp Leu His Lys Met Leu<br>                          685                       690                       695 | 2236 |
| atg gtg tat ttt gat tac atg aga agc tgg atc caa atg cta cag caa<br>Met Val Tyr Phe Asp Tyr Met Arg Ser Trp Ile Gln Met Leu Gln Gln<br>700                           705                       710 | 2284 |
| tta cct caa gca tcg cat agt tta aaa aat ctg tta gaa gaa gaa tgg<br>Leu Pro Gln Ala Ser His Ser Leu Lys Asn Leu Leu Glu Glu Glu Trp<br>715                           720                       725                730 | 2332 |
| aat ttc acc aaa gaa ata act cat tac ata cgg gga gga gaa gca cag<br>Asn Phe Thr Lys Glu Ile Thr His Tyr Ile Arg Gly Gly Glu Ala Gln<br>                          735                       740                       745 | 2380 |
| gcc ggg aag ctt ttc tgt gac att gca gga atg ctg ctg aaa tct aca<br>Ala Gly Lys Leu Phe Cys Asp Ile Ala Gly Met Leu Leu Lys Ser Thr<br>         750                       755                       760 | 2428 |
| gga agt ttt tta gaa ttt ggc tta cag gag agc tgt gct gaa ttt tgg<br>Gly Ser Phe Leu Glu Phe Gly Leu Gln Glu Ser Cys Ala Glu Phe Trp<br>                          765                       770                       775 | 2476 |
| act agt gcg gat gac agc agt gct tcc gac gaa atc agg agg tct gtt<br>Thr Ser Ala Asp Asp Ser Ser Ala Ser Asp Glu Ile Arg Arg Ser Val<br>780                           785                       790 | 2524 |
| ata gag atc agt cga gcc ctg aag gag ctc ttc cat gaa gcc aga gaa<br>Ile Glu Ile Ser Arg Ala Leu Lys Glu Leu Phe His Glu Ala Arg Glu<br>795                           800                       805                810 | 2572 |
| agg gct tcc aaa gca ctt gga ttt gct aaa atg ttg aga aag gac ctg<br>Arg Ala Ser Lys Ala Leu Gly Phe Ala Lys Met Leu Arg Lys Asp Leu<br>                          815                       820                       825 | 2620 |
| gaa ata gca gca gaa ttc agg ctt tca gcc cca gtt aga gac ctc ctg<br>Glu Ile Ala Ala Glu Phe Arg Leu Ser Ala Pro Val Arg Asp Leu Leu<br>                          830                       835                       840 | 2668 |
| gat gtt ctg aaa tca aaa cag tat gtc aag gtg caa att cct ggg tta<br>Asp Val Leu Lys Ser Lys Gln Tyr Val Lys Val Gln Ile Pro Gly Leu<br>845                           850                       855 | 2716 |

-continued

| | |
|---|---|
| gaa aac ttg caa atg ttt gtt cca gac act ctt gct gag gag aag agt<br>Glu Asn Leu Gln Met Phe Val Pro Asp Thr Leu Ala Glu Glu Lys Ser<br>860                 865                870 | 2764 |
| att att ttg cag tta ctc aat gca gct gca gga aag gac tgt tca aaa<br>Ile Ile Leu Gln Leu Leu Asn Ala Ala Ala Gly Lys Asp Cys Ser Lys<br>875                880              885              890 | 2812 |
| gat tca gat gac gta ctc atc gat gcc tat ctg ctt ctg acc aag cac<br>Asp Ser Asp Asp Val Leu Ile Asp Ala Tyr Leu Leu Leu Thr Lys His<br>                895              900              905 | 2860 |
| ggt gat cga gcc cgt gat tca gag gac agc tgg ggc acc tgg gag gca<br>Gly Asp Arg Ala Arg Asp Ser Glu Asp Ser Trp Gly Thr Trp Glu Ala<br>910                915                920 | 2908 |
| cag cct gtc aaa gtc gtg cct cag gtg gag act gtt gac acc ctg aga<br>Gln Pro Val Lys Val Val Pro Gln Val Glu Thr Val Asp Thr Leu Arg<br>925                930              935 | 2956 |
| agc atg cag gtg gat aat ctt tta cta gtt gtc atg cag tct gcg cat<br>Ser Met Gln Val Asp Asn Leu Leu Leu Val Val Met Gln Ser Ala His<br>940                945              950 | 3004 |
| ctc aca att cag aga aaa gct ttc cag cag tcc att gag gga ctt atg<br>Leu Thr Ile Gln Arg Lys Ala Phe Gln Gln Ser Ile Glu Gly Leu Met<br>955                960              965              970 | 3052 |
| act ctg tgc cag gag cag aca tcc agt cag ccg gtc atc gcc aaa gct<br>Thr Leu Cys Gln Glu Gln Thr Ser Ser Gln Pro Val Ile Ala Lys Ala<br>                975              980              985 | 3100 |
| ttg cag cag ctg aag aat gat gca ttg gag cta tgc aac agg ata agc<br>Leu Gln Gln Leu Lys Asn Asp Ala Leu Glu Leu Cys Asn Arg Ile Ser<br>990                995              1000 | 3148 |
| aat gcc att gac cgc gtg gac cac atg ttc aca tca gaa ttt gat<br>Asn Ala Ile Asp Arg Val Asp His Met Phe Thr Ser Glu Phe Asp<br>1005                1010              1015 | 3193 |
| gct gag gtt gat gaa tct gaa tct gtc acc ttg caa cag tac tac<br>Ala Glu Val Asp Glu Ser Glu Ser Val Thr Leu Gln Gln Tyr Tyr<br>1020                1025              1030 | 3238 |
| cga gaa gca atg att cag ggg tac aat ttt gga ttt gag tat cat<br>Arg Glu Ala Met Ile Gln Gly Tyr Asn Phe Gly Phe Glu Tyr His<br>1035                1040              1045 | 3283 |
| aaa gaa gtt gtt cgt ttg atg tct ggg gag ttt aga cag aag ata<br>Lys Glu Val Val Arg Leu Met Ser Gly Glu Phe Arg Gln Lys Ile<br>1050                1055              1060 | 3328 |
| gga gac aaa tat ata agc ttt gcc cgg aag tgg atg aat tat gtc<br>Gly Asp Lys Tyr Ile Ser Phe Ala Arg Lys Trp Met Asn Tyr Val<br>1065                1070              1075 | 3373 |
| ctg act aaa tgt gag agt ggt aga ggt aca aga ccc agg tgg gcg<br>Leu Thr Lys Cys Glu Ser Gly Arg Gly Thr Arg Pro Arg Trp Ala<br>1080                1085              1090 | 3418 |
| act caa gga ttt gat ttt cta caa gca att gaa cct gcc ttt att<br>Thr Gln Gly Phe Asp Phe Leu Gln Ala Ile Glu Pro Ala Phe Ile<br>1095                1100              1105 | 3463 |
| tca gct tta cca gaa gat gac ttc ttg agt tta caa gcc ttg atg<br>Ser Ala Leu Pro Glu Asp Asp Phe Leu Ser Leu Gln Ala Leu Met<br>1110                1115              1120 | 3508 |
| aat gaa tgc att ggc cat gtc ata gga aaa cca cac agt cct gtt<br>Asn Glu Cys Ile Gly His Val Ile Gly Lys Pro His Ser Pro Val<br>1125                1130              1135 | 3553 |
| aca ggt ttg tac ctt gcc att cat cgg aac agc ccc cgt cct atg<br>Thr Gly Leu Tyr Leu Ala Ile His Arg Asn Ser Pro Arg Pro Met<br>1140                1145              1150 | 3598 |
| aag gta cct cga tgc cat agt gac cct cct aac cca cac ctc att<br>Lys Val Pro Arg Cys His Ser Asp Pro Pro Asn Pro His Leu Ile | 3643 |

-continued

| | | | | | | | | | | | |
|---|---|---|---|---|---|---|---|---|---|---|---|
| | | | | 1155 | | | 1160 | | | 1165 | |
| atc | ccc | act | cca | gag | gga | ttc | agg | ggt | tcc | agc | gtt | cct | gaa | aat | 3688 |
| Ile | Pro | Thr | Pro | Glu | Gly | Phe | Arg | Gly | Ser | Ser | Val | Pro | Glu | Asn | |
| | | | 1170 | | | | 1175 | | | | 1180 | | | | |
| gat | cga | ttg | gct | tcc | ata | gct | gct | gaa | ttg | cag | ttt | agg | tcc | ctg | 3733 |
| Asp | Arg | Leu | Ala | Ser | Ile | Ala | Ala | Glu | Leu | Gln | Phe | Arg | Ser | Leu | |
| | | 1185 | | | | | 1190 | | | | | 1195 | | | |
| agt | cgt | cac | tca | agc | ccc | acg | gag | gag | cga | gat | gaa | cca | gca | tat | 3778 |
| Ser | Arg | His | Ser | Ser | Pro | Thr | Glu | Glu | Arg | Asp | Glu | Pro | Ala | Tyr | |
| | | 1200 | | | | | 1205 | | | | | 1210 | | | |
| cca | aga | gga | gat | tca | agt | ggg | tcc | aca | aga | aga | agt | tgg | gaa | ctt | 3823 |
| Pro | Arg | Gly | Asp | Ser | Ser | Gly | Ser | Thr | Arg | Arg | Ser | Trp | Glu | Leu | |
| | | 1215 | | | | | 1220 | | | | | 1225 | | | |
| cgg | aca | cta | atc | agc | cag | agt | aaa | gat | act | gct | tct | aaa | cta | gga | 3868 |
| Arg | Thr | Leu | Ile | Ser | Gln | Ser | Lys | Asp | Thr | Ala | Ser | Lys | Leu | Gly | |
| | 1230 | | | | | 1235 | | | | | 1240 | | | | |
| ccc | ata | gaa | gct | atc | cag | aag | tca | gtc | cga | ttg | ttt | gaa | gaa | aag | 3913 |
| Pro | Ile | Glu | Ala | Ile | Gln | Lys | Ser | Val | Arg | Leu | Phe | Glu | Glu | Lys | |
| | 1245 | | | | | 1250 | | | | | 1255 | | | | |
| agg | tac | cga | gaa | atg | agg | aga | aag | aat | atc | att | ggt | caa | gtt | tgt | 3958 |
| Arg | Tyr | Arg | Glu | Met | Arg | Arg | Lys | Asn | Ile | Ile | Gly | Gln | Val | Cys | |
| | 1260 | | | | | 1265 | | | | | 1270 | | | | |
| gat | acg | cct | aag | tcc | tat | gat | aat | gtt | atg | cac | gtt | ggc | ttg | agg | 4003 |
| Asp | Thr | Pro | Lys | Ser | Tyr | Asp | Asn | Val | Met | His | Val | Gly | Leu | Arg | |
| | 1275 | | | | | 1280 | | | | | 1285 | | | | |
| aag | gtg | acc | ttc | aaa | tgg | caa | aga | gga | aac | aaa | att | gga | gaa | ggc | 4048 |
| Lys | Val | Thr | Phe | Lys | Trp | Gln | Arg | Gly | Asn | Lys | Ile | Gly | Glu | Gly | |
| | 1290 | | | | | 1295 | | | | | 1300 | | | | |
| cag | tat | ggg | aag | gtg | tac | acc | tgc | atc | agc | gtc | gac | acc | ggg | gag | 4093 |
| Gln | Tyr | Gly | Lys | Val | Tyr | Thr | Cys | Ile | Ser | Val | Asp | Thr | Gly | Glu | |
| | 1305 | | | | | 1310 | | | | | 1315 | | | | |
| ctg | atg | gcc | atg | aaa | gag | att | cga | ttt | caa | cct | aat | gac | cat | aag | 4138 |
| Leu | Met | Ala | Met | Lys | Glu | Ile | Arg | Phe | Gln | Pro | Asn | Asp | His | Lys | |
| | 1320 | | | | | 1325 | | | | | 1330 | | | | |
| act | atc | aag | gaa | act | gca | gac | gaa | ttg | aaa | ata | ttc | gaa | ggc | atc | 4183 |
| Thr | Ile | Lys | Glu | Thr | Ala | Asp | Glu | Leu | Lys | Ile | Phe | Glu | Gly | Ile | |
| | 1335 | | | | | 1340 | | | | | 1345 | | | | |
| aaa | cac | ccc | aat | ctg | gtt | cgg | tat | ttt | ggt | gtg | gag | ctc | cat | aga | 4228 |
| Lys | His | Pro | Asn | Leu | Val | Arg | Tyr | Phe | Gly | Val | Glu | Leu | His | Arg | |
| | 1350 | | | | | 1355 | | | | | 1360 | | | | |
| gaa | gaa | atg | tac | atc | ttc | atg | gag | tac | tgc | gat | gag | ggg | act | tta | 4273 |
| Glu | Glu | Met | Tyr | Ile | Phe | Met | Glu | Tyr | Cys | Asp | Glu | Gly | Thr | Leu | |
| | 1365 | | | | | 1370 | | | | | 1375 | | | | |
| gaa | gag | gtg | tca | agg | ctg | gga | ctt | cag | gaa | cat | gtg | att | agg | ctg | 4318 |
| Glu | Glu | Val | Ser | Arg | Leu | Gly | Leu | Gln | Glu | His | Val | Ile | Arg | Leu | |
| | 1380 | | | | | 1385 | | | | | 1390 | | | | |
| tat | tca | aag | cag | atc | acc | att | gcg | atc | aac | gtc | ctc | cat | gag | cat | 4363 |
| Tyr | Ser | Lys | Gln | Ile | Thr | Ile | Ala | Ile | Asn | Val | Leu | His | Glu | His | |
| | 1395 | | | | | 1400 | | | | | 1405 | | | | |
| ggc | ata | gtc | cac | cgt | gac | att | aaa | ggt | gcc | aat | atc | ttc | ctt | acc | 4408 |
| Gly | Ile | Val | His | Arg | Asp | Ile | Lys | Gly | Ala | Asn | Ile | Phe | Leu | Thr | |
| | 1410 | | | | | 1415 | | | | | 1420 | | | | |
| tca | tct | gga | tta | atc | aaa | ctg | gga | gat | ttt | gga | tgt | tca | gta | aag | 4453 |
| Ser | Ser | Gly | Leu | Ile | Lys | Leu | Gly | Asp | Phe | Gly | Cys | Ser | Val | Lys | |
| | 1425 | | | | | 1430 | | | | | 1435 | | | | |
| ctc | aaa | aac | aat | gcc | cag | acc | atg | cct | ggt | gaa | gtg | aac | agc | acc | 4498 |
| Leu | Lys | Asn | Asn | Ala | Gln | Thr | Met | Pro | Gly | Glu | Val | Asn | Ser | Thr | |
| | 1440 | | | | | 1445 | | | | | 1450 | | | | |
| ctg | ggg | aca | gca | gca | tac | atg | gca | cct | gaa | gtc | atc | act | cgt | gcc | 4543 |

```
                                                            -continued

Leu Gly Thr Ala Ala Tyr Met Ala Pro Glu Val Ile Thr Arg Ala
        1455                1460                1465 aaa gga gag ggc cat ggg cgt gcg gcc gac atc tgg agt ctg ggg    4588
Lys Gly Glu Gly His Gly Arg Ala Ala Asp Ile Trp Ser Leu Gly
        1470                1475                1480 tgt gtt gtc ata gag atg gtg act ggc aag agg cct tgg cat gag    4633
Cys Val Val Ile Glu Met Val Thr Gly Lys Arg Pro Trp His Glu
        1485                1490                1495 tat gag cac aac ttt caa att atg tat aaa gtg ggg atg gga cat    4678
Tyr Glu His Asn Phe Gln Ile Met Tyr Lys Val Gly Met Gly His
        1500                1505                1510 aag cca cca atc cct gaa aga tta agc cct gaa gga aag gac ttc    4723
Lys Pro Pro Ile Pro Glu Arg Leu Ser Pro Glu Gly Lys Asp Phe
        1515                1520                1525 ctt tct cac tgc ctt gag agt gac cca aag atg aga tgg acc gcc    4768
Leu Ser His Cys Leu Glu Ser Asp Pro Lys Met Arg Trp Thr Ala
        1530                1535                1540 agc cag ctc ctc gac cat tcg ttt gtc aag gtt tgc aca gat gaa    4813
Ser Gln Leu Leu Asp His Ser Phe Val Lys Val Cys Thr Asp Glu
        1545                1550                1555 gaa tga agcctagtag aatatggact tggaaaattc tcttaatcac tactgtatgt    4869
Glu aatatttaca taaagactgt gctgagaagc agtataagcc tttttaacct tccaagactg    4929
aagactgcac aggtgacaag cgtcacttct cctgctgctc ctgtttgtct gatgtggcaa    4989
aaggccctct ggagggctgg tggccacgag gttaaagaag ctgcatgtta agtgccatta    5049
ctactgtaca cggaccatcg cctctgtctc ctccgtgtct cgcgcgactg agaaccgtga    5109
catcagcgta gtgttttgac cttctaggt tcaaaagaag ttgtagtgtt atcaggcgtc    5169
ccatacctcg ttttaatct cctgtttgtt gagtgcactg actgtgaaac ctttacctttt    5229 tttgttgttg ttggcaagct gcaggtttgt aatgcaaaag gctgattact gaaatttaag    5289
aaaaaggtt                                                             5298

<210> SEQ ID NO 14
<211> LENGTH: 1558
<212> TYPE: PRT
<213> ORGANISM: Homo sapiens

<400> SEQUENCE: 14

Met Arg Glu Ala Ala Ala Ala Leu Val Pro Pro Pro Ala Phe Ala Val
1               5                   10                  15

Thr Pro Ala Ala Ala Met Glu Glu Pro Pro Pro Pro Pro Pro Pro Pro
            20                  25                  30

Pro Pro Pro Pro Glu Pro Glu Thr Glu Ser Glu Pro Glu Cys Cys Leu
        35                  40                  45

Ala Ala Arg Gln Glu Gly Thr Leu Gly Asp Ser Ala Cys Lys Ser Pro
    50                  55                  60

Glu Ser Asp Leu Glu Asp Phe Ser Asp Glu Thr Asn Thr Glu Asn Leu
65                  70                  75                  80

Tyr Gly Thr Ser Pro Ser Thr Pro Arg Gln Met Lys Arg Met Ser
                85                  90                  95

Thr Lys His Gln Arg Asn Asn Val Gly Arg Pro Ala Ser Arg Ser Asn
            100                 105                 110

Leu Lys Glu Lys Met Asn Ala Pro Asn Gln Pro Pro His Lys Asp Thr
        115                 120                 125

Gly Lys Thr Val Glu Asn Val Glu Glu Tyr Ser Tyr Lys Gln Glu Lys
```

-continued

```
            130                 135                 140
Lys Ile Arg Ala Ala Leu Arg Thr Thr Glu Arg Asp Arg Lys Lys Asn
145                 150                 155                 160

Val Gln Cys Ser Phe Met Leu Asp Ser Val Gly Gly Ser Leu Pro Lys
                165                 170                 175

Lys Ser Ile Pro Asp Val Asp Leu Asn Lys Pro Tyr Leu Ser Leu Gly
            180                 185                 190

Cys Ser Asn Ala Lys Leu Pro Val Ser Val Pro Met Pro Ile Ala Arg
                195                 200                 205

Pro Ala Arg Gln Thr Ser Arg Thr Asp Cys Pro Ala Asp Arg Leu Lys
210                 215                 220

Phe Phe Glu Thr Leu Arg Leu Leu Lys Leu Thr Ser Val Ser Lys
225                 230                 235                 240

Lys Lys Asp Arg Glu Gln Arg Gly Gln Glu Asn Thr Ser Gly Phe Trp
                245                 250                 255

Leu Asn Arg Ser Asn Glu Leu Ile Trp Leu Glu Leu Gln Ala Trp His
                260                 265                 270

Ala Gly Arg Thr Ile Asn Asp Gln Asp Phe Phe Leu Tyr Thr Ala Arg
            275                 280                 285

Gln Ala Ile Pro Asp Ile Ile Asn Glu Ile Leu Thr Phe Lys Val Asp
    290                 295                 300

Tyr Gly Ser Phe Ala Phe Val Arg Asp Arg Ala Gly Phe Asn Gly Thr
305                 310                 315                 320

Ser Val Glu Gly Gln Cys Lys Ala Thr Pro Gly Thr Lys Ile Val Gly
                325                 330                 335

Tyr Ser Thr His His Glu His Leu Gln Arg Gln Arg Val Ser Phe Glu
            340                 345                 350

Gln Val Lys Arg Ile Met Glu Leu Leu Glu Tyr Ile Glu Ala Leu Tyr
                355                 360                 365

Pro Ser Leu Gln Ala Leu Gln Lys Asp Tyr Glu Lys Tyr Ala Ala Lys
    370                 375                 380

Asp Phe Gln Asp Arg Val Gln Ala Leu Cys Leu Trp Leu Asn Ile Thr
385                 390                 395                 400

Lys Asp Leu Asn Gln Lys Leu Arg Ile Met Gly Thr Val Leu Gly Ile
                405                 410                 415

Lys Asn Leu Ser Asp Ile Gly Trp Pro Val Phe Glu Ile Pro Ser Pro
            420                 425                 430

Arg Pro Ser Lys Gly Asn Glu Pro Glu Tyr Gly Asp Asp Thr Glu
            435                 440                 445

Gly Glu Leu Lys Glu Leu Glu Ser Ser Thr Asp Glu Ser Glu Glu Glu
    450                 455                 460

Gln Ile Ser Asp Pro Arg Val Pro Glu Ile Arg Gln Pro Ile Asp Asn
465                 470                 475                 480

Ser Phe Asp Ile Gln Ser Arg Asp Cys Ile Ser Lys Lys Leu Glu Arg
                485                 490                 495

Leu Glu Ser Glu Asp Asp Ser Leu Gly Trp Gly Ala Pro Asp Trp Ser
            500                 505                 510

Thr Glu Ala Gly Phe Ser Arg His Cys Leu Thr Ser Ile Tyr Arg Pro
            515                 520                 525

Phe Val Asp Lys Ala Leu Lys Gln Met Gly Leu Arg Lys Leu Ile Leu
    530                 535                 540

Arg Leu His Lys Leu Met Asp Gly Ser Leu Gln Arg Ala Arg Ile Ala
545                 550                 555                 560
```

-continued

```
Leu Val Lys Asn Asp Arg Pro Val Glu Phe Ser Glu Phe Pro Asp Pro
            565                 570                 575

Met Trp Gly Ser Asp Tyr Val Gln Leu Ser Arg Thr Pro Pro Ser Ser
        580                 585                 590

Glu Glu Lys Cys Ser Ala Val Ser Trp Glu Leu Lys Ala Met Asp
        595                 600                 605

Leu Pro Ser Phe Glu Pro Ala Phe Leu Val Leu Cys Arg Val Leu Leu
        610                 615                 620

Asn Val Ile His Glu Cys Leu Lys Leu Arg Leu Glu Gln Arg Pro Ala
625                 630                 635                 640

Gly Glu Pro Ser Leu Leu Ser Ile Lys Gln Leu Val Arg Glu Cys Lys
            645                 650                 655

Glu Val Leu Lys Gly Gly Leu Leu Met Lys Gln Tyr Tyr Gln Phe Met
            660                 665                 670

Leu Gln Glu Val Leu Glu Asp Leu Glu Lys Pro Asp Cys Asn Ile Asp
            675                 680                 685

Ala Phe Glu Glu Asp Leu His Lys Met Leu Met Val Tyr Phe Asp Tyr
        690                 695                 700

Met Arg Ser Trp Ile Gln Met Leu Gln Gln Leu Pro Gln Ala Ser His
705                 710                 715                 720

Ser Leu Lys Asn Leu Leu Glu Glu Glu Trp Asn Phe Thr Lys Glu Ile
            725                 730                 735

Thr His Tyr Ile Arg Gly Gly Glu Ala Gln Ala Gly Lys Leu Phe Cys
            740                 745                 750

Asp Ile Ala Gly Met Leu Leu Lys Ser Thr Gly Ser Phe Leu Glu Phe
            755                 760                 765

Gly Leu Gln Glu Ser Cys Ala Glu Phe Trp Thr Ser Ala Asp Asp Ser
        770                 775                 780

Ser Ala Ser Asp Glu Ile Arg Arg Ser Val Ile Glu Ile Ser Arg Ala
785                 790                 795                 800

Leu Lys Glu Leu Phe His Glu Ala Arg Glu Arg Ala Ser Lys Ala Leu
            805                 810                 815

Gly Phe Ala Lys Met Leu Arg Lys Asp Leu Glu Ile Ala Ala Glu Phe
            820                 825                 830

Arg Leu Ser Ala Pro Val Arg Asp Leu Leu Asp Val Leu Lys Ser Lys
            835                 840                 845

Gln Tyr Val Lys Val Gln Ile Pro Gly Leu Glu Asn Leu Gln Met Phe
        850                 855                 860

Val Pro Asp Thr Leu Ala Glu Glu Lys Ser Ile Ile Leu Gln Leu Leu
865                 870                 875                 880

Asn Ala Ala Ala Gly Lys Asp Cys Ser Lys Asp Ser Asp Asp Val Leu
            885                 890                 895

Ile Asp Ala Tyr Leu Leu Leu Thr Lys His Gly Asp Arg Ala Arg Asp
            900                 905                 910

Ser Glu Asp Ser Trp Gly Thr Trp Glu Ala Gln Pro Val Lys Val Val
            915                 920                 925

Pro Gln Val Glu Thr Val Asp Thr Leu Arg Ser Met Gln Val Asp Asn
        930                 935                 940

Leu Leu Leu Val Val Met Gln Ser Ala His Leu Thr Ile Gln Arg Lys
945                 950                 955                 960

Ala Phe Gln Gln Ser Ile Glu Gly Leu Met Thr Leu Cys Gln Glu Gln
            965                 970                 975
```

-continued

```
Thr Ser Ser Gln Pro Val Ile Ala Lys Ala Leu Gln Gln Leu Lys Asn
            980                 985                 990

Asp Ala Leu Glu Leu Cys Asn Arg  Ile Ser Asn Ala Ile  Asp Arg Val
        995                 1000                1005

Asp His Met Phe Thr Ser Glu  Phe Asp Ala Glu Val  Asp Glu Ser
        1010                1015                1020

Glu Ser Val Thr Leu Gln Gln  Tyr Tyr Arg Glu Ala  Met Ile Gln
        1025                1030                1035

Gly Tyr Asn Phe Gly Phe Glu  Tyr His Lys Glu Val  Val Arg Leu
        1040                1045                1050

Met Ser Gly Glu Phe Arg Gln  Lys Ile Gly Asp Lys  Tyr Ile Ser
        1055                1060                1065

Phe Ala Arg Lys Trp Met Asn  Tyr Val Leu Thr Lys  Cys Glu Ser
        1070                1075                1080

Gly Arg Gly Thr Arg Pro Arg  Trp Ala Thr Gln Gly  Phe Asp Phe
        1085                1090                1095

Leu Gln Ala Ile Glu Pro Ala  Phe Ile Ser Ala Leu  Pro Glu Asp
        1100                1105                1110

Asp Phe Leu Ser Leu Gln Ala  Leu Met Asn Glu Cys  Ile Gly His
        1115                1120                1125

Val Ile Gly Lys Pro His Ser  Pro Val Thr Gly Leu  Tyr Leu Ala
        1130                1135                1140

Ile His Arg Asn Ser Pro Arg  Pro Met Lys Val Pro  Arg Cys His
        1145                1150                1155

Ser Asp Pro Pro Asn Pro His  Leu Ile Ile Pro Thr  Pro Glu Gly
        1160                1165                1170

Phe Arg Gly Ser Ser Val Pro  Glu Asn Asp Arg Leu  Ala Ser Ile
        1175                1180                1185

Ala Ala Glu Leu Gln Phe Arg  Ser Leu Ser Arg His  Ser Ser Pro
        1190                1195                1200

Thr Glu Glu Arg Asp Glu Pro  Ala Tyr Pro Arg Gly  Asp Ser Ser
        1205                1210                1215

Gly Ser Thr Arg Arg Ser Trp  Glu Leu Arg Thr Leu  Ile Ser Gln
        1220                1225                1230

Ser Lys Asp Thr Ala Ser Lys  Leu Gly Pro Ile Glu  Ala Ile Gln
        1235                1240                1245

Lys Ser Val Arg Leu Phe Glu  Glu Lys Arg Tyr Arg  Glu Met Arg
        1250                1255                1260

Arg Lys Asn Ile Ile Gly Gln  Val Cys Asp Thr Pro  Lys Ser Tyr
        1265                1270                1275

Asp Asn Val Met His Val Gly  Leu Arg Lys Val Thr  Phe Lys Trp
        1280                1285                1290

Gln Arg Gly Asn Lys Ile Gly  Glu Gly Gln Tyr Gly  Lys Val Tyr
        1295                1300                1305

Thr Cys Ile Ser Val Asp Thr  Gly Glu Leu Met Ala  Met Lys Glu
        1310                1315                1320

Ile Arg Phe Gln Pro Asn Asp  His Lys Thr Ile Lys  Glu Thr Ala
        1325                1330                1335

Asp Glu Leu Lys Ile Phe Glu  Gly Ile Lys His Pro  Asn Leu Val
        1340                1345                1350

Arg Tyr Phe Gly Val Glu Leu  His Arg Glu Glu Met  Tyr Ile Phe
        1355                1360                1365

Met Glu Tyr Cys Asp Glu Gly  Thr Leu Glu Glu Val  Ser Arg Leu
```

```
                1370                1375                1380
Gly Leu Gln Glu His Val Ile Arg Leu Tyr Ser Lys Gln Ile Thr
    1385                1390                1395

Ile Ala Ile Asn Val Leu His Glu His Gly Ile Val His Arg Asp
    1400                1405                1410

Ile Lys Gly Ala Asn Ile Phe Leu Thr Ser Ser Gly Leu Ile Lys
    1415                1420                1425

Leu Gly Asp Phe Gly Cys Ser Val Lys Leu Lys Asn Asn Ala Gln
    1430                1435                1440

Thr Met Pro Gly Glu Val Asn Ser Thr Leu Gly Thr Ala Ala Tyr
    1445                1450                1455

Met Ala Pro Glu Val Ile Thr Arg Ala Lys Gly Glu Gly His Gly
    1460                1465                1470

Arg Ala Ala Asp Ile Trp Ser Leu Gly Cys Val Val Ile Glu Met
    1475                1480                1485

Val Thr Gly Lys Arg Pro Trp His Glu Tyr Glu His Asn Phe Gln
    1490                1495                1500

Ile Met Tyr Lys Val Gly Met Gly His Lys Pro Pro Ile Pro Glu
    1505                1510                1515

Arg Leu Ser Pro Glu Gly Lys Asp Phe Leu Ser His Cys Leu Glu
    1520                1525                1530

Ser Asp Pro Lys Met Arg Trp Thr Ala Ser Gln Leu Leu Asp His
    1535                1540                1545

Ser Phe Val Lys Val Cys Thr Asp Glu Glu
    1550                1555

<210> SEQ ID NO 15
<211> LENGTH: 2966
<212> TYPE: DNA
<213> ORGANISM: Homo sapiens
<220> FEATURE:
<221> NAME/KEY: CDS
<222> LOCATION: (63)..(2891)
<223> OTHER INFORMATION:

<400> SEQUENCE: 15
acgcgcgctc ctctggccgc ccctccctcc gcgcggggac ccctggcggg cggcaggagg     60 ac atg gcc agc gac gcc gtg cag agt gag cct cgc agc tgg tcc ctg       107
   Met Ala Ser Asp Ala Val Gln Ser Glu Pro Arg Ser Trp Ser Leu
   1               5                   10                  15 cta gag cag ctg ggc ctg gcc ggg gca gac ctg gcg gcc ccc ggg gta     155
Leu Glu Gln Leu Gly Leu Ala Gly Ala Asp Leu Ala Ala Pro Gly Val
                20                  25                  30 cag cag cag ctg gag ctg gag cgg gag cgg ctg cgg cgg gaa atc cgc     203
Gln Gln Gln Leu Glu Leu Glu Arg Glu Arg Leu Arg Arg Glu Ile Arg
            35                  40                  45 aag gag ctg aag ctg aag gag ggt gct gag aac ctg cgg cgg gcc acc     251
Lys Glu Leu Lys Leu Lys Glu Gly Ala Glu Asn Leu Arg Arg Ala Thr
        50                  55                  60 act gac ctg ggc cgc agc ctg ggc ccc gta gag ctg ctg ctg cgg ggc     299
Thr Asp Leu Gly Arg Ser Leu Gly Pro Val Glu Leu Leu Leu Arg Gly
    65                  70                  75 tcc tcg cgc cgc ctc gac ctg ctg cac cag cag ctg cag gag ctg cac     347
Ser Ser Arg Arg Leu Asp Leu Leu His Gln Gln Leu Gln Glu Leu His
80                  85                  90                  95 gcc cac gtg gtg ctt ccc gac ccg gcg gcc acc cac gat ggc ccc cag     395
Ala His Val Val Leu Pro Asp Pro Ala Ala Thr His Asp Gly Pro Gln
                100                 105                 110
```

```
tcc cct ggt gcg ggt ggc ccc acc tgc tcg gcc acc aac ctg agc cgc      443
Ser Pro Gly Ala Gly Gly Pro Thr Cys Ser Ala Thr Asn Leu Ser Arg
            115                 120                 125 gtg gcg ggc ctg gag aag cag ttg gcc att gag ctg aag gtg aag cag      491
Val Ala Gly Leu Glu Lys Gln Leu Ala Ile Glu Leu Lys Val Lys Gln
        130                 135                 140 ggg gcg gag aac atg atc cag acc tac agc aat ggc agc acc aag gac      539
Gly Ala Glu Asn Met Ile Gln Thr Tyr Ser Asn Gly Ser Thr Lys Asp
    145                 150                 155 cgg aag ctg ctg ctg aca gcc cag cag atg ttg cag gac agt aag acc      587
Arg Lys Leu Leu Leu Thr Ala Gln Gln Met Leu Gln Asp Ser Lys Thr
160                 165                 170                 175 aag att gac atc atc cgc atg caa ctc cgc cgg gcg ctg cag gcc ggc      635
Lys Ile Asp Ile Ile Arg Met Gln Leu Arg Arg Ala Leu Gln Ala Gly
                180                 185                 190 cag ctg gag aac cag gca gcc ccg gat gac acc caa ggg agt cct gac      683
Gln Leu Glu Asn Gln Ala Ala Pro Asp Asp Thr Gln Gly Ser Pro Asp
            195                 200                 205 ctg ggg gct gtg gag ctg cgc atc gaa gag ctg cgg cac cac ttc cga      731
Leu Gly Ala Val Glu Leu Arg Ile Glu Glu Leu Arg His His Phe Arg
        210                 215                 220 gtg gag cac gcg gtg gcc gag ggt gcc aag aac gta ctg cgc ctg ctc      779
Val Glu His Ala Val Ala Glu Gly Ala Lys Asn Val Leu Arg Leu Leu
    225                 230                 235 agc gct gcc aag gcc ccg gac cgc aag gca gtc agc gag gcc cag gag      827
Ser Ala Ala Lys Ala Pro Asp Arg Lys Ala Val Ser Glu Ala Gln Glu
240                 245                 250                 255 aaa tta aca gaa tcc aac cag aag ctg ggg ctg ctg cgg gag gct ctg      875
Lys Leu Thr Glu Ser Asn Gln Lys Leu Gly Leu Leu Arg Glu Ala Leu
                260                 265                 270 gag cgg aga ctt ggg gag ctg ccc gcc gac cac ccc aag ggg cgg ctg      923
Glu Arg Arg Leu Gly Glu Leu Pro Ala Asp His Pro Lys Gly Arg Leu
            275                 280                 285 ctg cga gaa gag ctc gct gcg gcc tcc tcc gct gcc ttc agc acc cgc      971
Leu Arg Glu Glu Leu Ala Ala Ala Ser Ser Ala Ala Phe Ser Thr Arg
        290                 295                 300 ctg gcc ggg ccc ttt ccc gcc acg cac tac agc acc ctg tgc aag ccc     1019
Leu Ala Gly Pro Phe Pro Ala Thr His Tyr Ser Thr Leu Cys Lys Pro
    305                 310                 315 gcg ccg ctc aca ggg acc ctg gag gta cga gtg gtg ggc tgc aga gac     1067
Ala Pro Leu Thr Gly Thr Leu Glu Val Arg Val Val Gly Cys Arg Asp
320                 325                 330                 335 ctc cca gag acc atc ccg tgg aac cct acc ccc tca atg ggg gga cct     1115
Leu Pro Glu Thr Ile Pro Trp Asn Pro Thr Pro Ser Met Gly Gly Pro
                340                 345                 350 ggg acc cca gac agc cgc ccc ccc ttc ctg agc cgc cca gcc cgg ggc     1163
Gly Thr Pro Asp Ser Arg Pro Pro Phe Leu Ser Arg Pro Ala Arg Gly
            355                 360                 365 ctt tac agc cga agc gga agc ctc agt ggc cgg agc agc ctc aaa gca     1211
Leu Tyr Ser Arg Ser Gly Ser Leu Ser Gly Arg Ser Ser Leu Lys Ala
        370                 375                 380 gaa gcc gag aac acc agt gaa gtc agc act gtg ctt aag ctg gat aac     1259
Glu Ala Glu Asn Thr Ser Glu Val Ser Thr Val Leu Lys Leu Asp Asn
    385                 390                 395 aca gtg gtg ggg cag acg tct tgg aag cca tgt ggc ccc aat gcc tgg     1307
Thr Val Val Gly Gln Thr Ser Trp Lys Pro Cys Gly Pro Asn Ala Trp
400                 405                 410                 415 gac cag agc ttc act ctg gag ctg gaa agg gca cgg gaa ctg gag ttg     1355
Asp Gln Ser Phe Thr Leu Glu Leu Glu Arg Ala Arg Glu Leu Glu Leu
```

-continued

```
                420             425             430
gct gtg ttc tgg cgg gac cag cgg ggc ctg tgt gcc ctc aaa ttc ctg    1403
Ala Val Phe Trp Arg Asp Gln Arg Gly Leu Cys Ala Leu Lys Phe Leu
            435             440             445 aag ttg gag gat ttc ttg gac aat gag agg cat gag gtg cag ctg gac    1451
Lys Leu Glu Asp Phe Leu Asp Asn Glu Arg His Glu Val Gln Leu Asp
        450             455             460 atg gaa ccc cag ggc tgc ctg gtg gct gag gtc acc ttc cgc aac cct    1499
Met Glu Pro Gln Gly Cys Leu Val Ala Glu Val Thr Phe Arg Asn Pro
465             470             475 gtc att gag agg att cct cgg ctc cga cgg cag aag aaa att ttc tcc    1547
Val Ile Glu Arg Ile Pro Arg Leu Arg Arg Gln Lys Lys Ile Phe Ser
480             485             490             495 aag cag caa ggg aag gcg ttc cag cgt gct agg cag atg aac atc gat    1595
Lys Gln Gln Gly Lys Ala Phe Gln Arg Ala Arg Gln Met Asn Ile Asp
            500             505             510 gtc gcc acg tgg gtg cgg ctg ctc cgg agg ctc atc ccc aat gcc acg    1643
Val Ala Thr Trp Val Arg Leu Leu Arg Arg Leu Ile Pro Asn Ala Thr
        515             520             525 ggc aca ggc acc ttt agc cct ggg gct tct cca gga tcc gag gcc cgg    1691
Gly Thr Gly Thr Phe Ser Pro Gly Ala Ser Pro Gly Ser Glu Ala Arg
    530             535             540 acc acg ggt gac ata tcg gtg gag aag ctg aac ctc ggc act gac tcg    1739
Thr Thr Gly Asp Ile Ser Val Glu Lys Leu Asn Leu Gly Thr Asp Ser
545             550             555 gac agc tca cct cag aag agc tcg cgg gat cct cct tcc agc cca tcg    1787
Asp Ser Ser Pro Gln Lys Ser Ser Arg Asp Pro Pro Ser Ser Pro Ser
560             565             570             575 agc ctg agc tcc ccc atc cag gaa tcc act gct ccc gag ctg cct tcg    1835
Ser Leu Ser Ser Pro Ile Gln Glu Ser Thr Ala Pro Glu Leu Pro Ser
            580             585             590 gag acc cag gag acc cca ggc ccc gcc ctg tgc agc cct ctg agg aag    1883
Glu Thr Gln Glu Thr Pro Gly Pro Ala Leu Cys Ser Pro Leu Arg Lys
        595             600             605 tca cct ctg acc ctc gaa gat ttc aag ttc ctg gcg gtg ctg ggc cgg    1931
Ser Pro Leu Thr Leu Glu Asp Phe Lys Phe Leu Ala Val Leu Gly Arg
    610             615             620 ggt cat ttt ggg aag gtg ctc ctc tcc gaa ttc cgg ccc agt ggg gag    1979
Gly His Phe Gly Lys Val Leu Leu Ser Glu Phe Arg Pro Ser Gly Glu
625             630             635 ctg ttc gcc atc aag gct ctg aag aaa ggg gac att gtg gcc cga gac    2027
Leu Phe Ala Ile Lys Ala Leu Lys Lys Gly Asp Ile Val Ala Arg Asp
640             645             650             655 gag gtg gag agc ctg atg tgt gag aag cgg ata ttg gcg gca gtg acc    2075
Glu Val Glu Ser Leu Met Cys Glu Lys Arg Ile Leu Ala Ala Val Thr
            660             665             670 agt gcg gga cac ccc ttc ctg gtg aac ctc ttc ggc tgt ttc cag aca    2123
Ser Ala Gly His Pro Phe Leu Val Asn Leu Phe Gly Cys Phe Gln Thr
        675             680             685 ccg gag cac gtg tgc ttc gtg atg gag tac tcg gcc ggt ggg gac ctg    2171
Pro Glu His Val Cys Phe Val Met Glu Tyr Ser Ala Gly Gly Asp Leu
    690             695             700 atg ctg cac atc cac agc gac gtg ttc tct gag ccc cgt gcc atc ttt    2219
Met Leu His Ile His Ser Asp Val Phe Ser Glu Pro Arg Ala Ile Phe
705             710             715 tat tcc gcc tgc gtg gtg ctg ggc cta cag ttt ctt cac gaa cac aag    2267
Tyr Ser Ala Cys Val Val Leu Gly Leu Gln Phe Leu His Glu His Lys
720             725             730             735 atc gtc tac agg gac ctg aag ttg gac aat ttg ctc ctg gac acc gag    2315
```

```
Ile Val Tyr Arg Asp Leu Lys Leu Asp Asn Leu Leu Leu Asp Thr Glu
            740                 745                 750 ggc tac gtc aag atc gca gac ttt ggc ctc tgc aag gag ggg atg ggc      2363
Gly Tyr Val Lys Ile Ala Asp Phe Gly Leu Cys Lys Glu Gly Met Gly
            755                 760                 765 tat ggg gac cgg acc agc aca ttc tgt ggg acc ccg gag ttc ctg gcc      2411
Tyr Gly Asp Arg Thr Ser Thr Phe Cys Gly Thr Pro Glu Phe Leu Ala
            770                 775                 780 cct gag gtg ctg acg gac acg tcg tac acg cga gct gtg gac tgg tgg      2459
Pro Glu Val Leu Thr Asp Thr Ser Tyr Thr Arg Ala Val Asp Trp Trp
785                 790                 795 gga ctg ggt gtg ctg ctc tac gag atg ctg gtt ggc gag tcc cca ttc      2507
Gly Leu Gly Val Leu Leu Tyr Glu Met Leu Val Gly Glu Ser Pro Phe
800                 805                 810                 815 cca ggg gat gat gag gag gag gtc ttc gac agc atc gtc aac gac gag      2555
Pro Gly Asp Asp Glu Glu Glu Val Phe Asp Ser Ile Val Asn Asp Glu
            820                 825                 830 gtt cgc tac ccc cgc ttc ctg tcg gcc gaa gcc atc ggc atc atg aga      2603
Val Arg Tyr Pro Arg Phe Leu Ser Ala Glu Ala Ile Gly Ile Met Arg
            835                 840                 845 agg ctg ctt cgg agg aac cca gag cgg agg ctg gga tct agc gag aga      2651
Arg Leu Leu Arg Arg Asn Pro Glu Arg Arg Leu Gly Ser Ser Glu Arg
            850                 855                 860 gat gca gaa gat gtg aag aaa cag ccc ttc ttc agg act ctg ggc tgg      2699
Asp Ala Glu Asp Val Lys Lys Gln Pro Phe Phe Arg Thr Leu Gly Trp
865                 870                 875 gaa gcc ctg ttg gcc cgg cgc ctg cca ccg ccc ttt gtg ccc acg ctg      2747
Glu Ala Leu Leu Ala Arg Arg Leu Pro Pro Pro Phe Val Pro Thr Leu
880                 885                 890                 895 tcc ggc cgc acc gac gtc agc aac ttc gac gag gag ttc acc ggg gag      2795
Ser Gly Arg Thr Asp Val Ser Asn Phe Asp Glu Glu Phe Thr Gly Glu
                900                 905                 910 gcc ccc aca ctg agc ccg ccc cgc gac gcg cgg ccc ctc aca gcc gcg      2843
Ala Pro Thr Leu Ser Pro Pro Arg Asp Ala Arg Pro Leu Thr Ala Ala
            915                 920                 925 gag cag gca gcc ttc ctg gac ttc gac ttc gtg gcc ggg ggc tgc tag      2891
Glu Gln Ala Ala Phe Leu Asp Phe Asp Phe Val Ala Gly Gly Cys
            930                 935                 940 ccccctcccc tgccctgcc cctgccctg cccgagagct cttagttttt aaaaaggcct      2951
ttgggatttg ccgga                                                     2966

<210> SEQ ID NO 16
<211> LENGTH: 942
<212> TYPE: PRT
<213> ORGANISM: Homo sapiens

<400> SEQUENCE: 16

Met Ala Ser Asp Ala Val Gln Ser Glu Pro Arg Ser Trp Ser Leu Leu
1               5                   10                  15

Glu Gln Leu Gly Leu Ala Gly Ala Asp Leu Ala Ala Pro Gly Val Gln
            20                  25                  30

Gln Gln Leu Glu Leu Glu Arg Glu Arg Leu Arg Arg Glu Ile Arg Lys
        35                  40                  45

Glu Leu Lys Leu Lys Glu Gly Ala Glu Asn Leu Arg Arg Ala Thr Thr
    50                  55                  60

Asp Leu Gly Arg Ser Leu Gly Pro Val Glu Leu Leu Leu Arg Gly Ser
65                  70                  75                  80

Ser Arg Arg Leu Asp Leu Leu His Gln Gln Leu Gln Glu Leu His Ala
```

```
                    85                  90                  95
His Val Val Leu Pro Asp Pro Ala Ala Thr His Asp Gly Pro Gln Ser
                100                 105                 110
Pro Gly Ala Gly Gly Pro Thr Cys Ser Ala Thr Asn Leu Ser Arg Val
                115                 120                 125
Ala Gly Leu Glu Lys Gln Leu Ala Ile Glu Leu Lys Val Lys Gln Gly
                130                 135                 140
Ala Glu Asn Met Ile Gln Thr Tyr Ser Asn Gly Ser Thr Lys Asp Arg
145                 150                 155                 160
Lys Leu Leu Leu Thr Ala Gln Gln Met Leu Gln Asp Ser Lys Thr Lys
                165                 170                 175
Ile Asp Ile Ile Arg Met Gln Leu Arg Arg Ala Leu Gln Ala Gly Gln
                180                 185                 190
Leu Glu Asn Gln Ala Ala Pro Asp Asp Thr Gln Gly Ser Pro Asp Leu
                195                 200                 205
Gly Ala Val Glu Leu Arg Ile Glu Glu Leu Arg His His Phe Arg Val
                210                 215                 220
Glu His Ala Val Ala Glu Gly Ala Lys Asn Val Leu Arg Leu Leu Ser
225                 230                 235                 240
Ala Ala Lys Ala Pro Asp Arg Lys Ala Val Ser Glu Ala Gln Glu Lys
                245                 250                 255
Leu Thr Glu Ser Asn Gln Lys Leu Gly Leu Leu Arg Glu Ala Leu Glu
                260                 265                 270
Arg Arg Leu Gly Glu Leu Pro Ala Asp His Pro Lys Gly Arg Leu Leu
                275                 280                 285
Arg Glu Glu Leu Ala Ala Ala Ser Ser Ala Ala Phe Ser Thr Arg Leu
                290                 295                 300
Ala Gly Pro Phe Pro Ala Thr His Tyr Ser Thr Leu Cys Lys Pro Ala
305                 310                 315                 320
Pro Leu Thr Gly Thr Leu Glu Val Arg Val Gly Cys Arg Asp Leu
                325                 330                 335
Pro Glu Thr Ile Pro Trp Asn Pro Thr Pro Ser Met Gly Gly Pro Gly
                340                 345                 350
Thr Pro Asp Ser Arg Pro Pro Phe Leu Ser Arg Pro Ala Arg Gly Leu
                355                 360                 365
Tyr Ser Arg Ser Gly Ser Leu Ser Gly Arg Ser Ser Leu Lys Ala Glu
                370                 375                 380
Ala Glu Asn Thr Ser Glu Val Ser Thr Val Leu Lys Leu Asp Asn Thr
385                 390                 395                 400
Val Val Gly Gln Thr Ser Trp Lys Pro Cys Gly Pro Asn Ala Trp Asp
                405                 410                 415
Gln Ser Phe Thr Leu Glu Leu Glu Arg Ala Arg Glu Leu Glu Leu Ala
                420                 425                 430
Val Phe Trp Arg Asp Gln Arg Gly Leu Cys Ala Leu Lys Phe Leu Lys
                435                 440                 445
Leu Glu Asp Phe Leu Asp Asn Glu Arg His Glu Val Gln Leu Asp Met
                450                 455                 460
Glu Pro Gln Gly Cys Leu Val Ala Glu Val Thr Phe Arg Asn Pro Val
465                 470                 475                 480
Ile Glu Arg Ile Pro Arg Leu Arg Arg Gln Lys Lys Ile Phe Ser Lys
                485                 490                 495
Gln Gln Gly Lys Ala Phe Gln Arg Ala Arg Gln Met Asn Ile Asp Val
                500                 505                 510
```

-continued

```
Ala Thr Trp Val Arg Leu Leu Arg Arg Leu Ile Pro Asn Ala Thr Gly
            515                 520                 525

Thr Gly Thr Phe Ser Pro Gly Ala Ser Pro Gly Ser Glu Ala Arg Thr
        530                 535                 540

Thr Gly Asp Ile Ser Val Glu Lys Leu Asn Leu Gly Thr Asp Ser Asp
545                 550                 555                 560

Ser Ser Pro Gln Lys Ser Ser Arg Asp Pro Ser Ser Pro Ser Ser
                565                 570                 575

Leu Ser Ser Pro Ile Gln Glu Ser Thr Ala Pro Glu Leu Pro Ser Glu
            580                 585                 590

Thr Gln Glu Thr Pro Gly Pro Ala Leu Cys Ser Pro Leu Arg Lys Ser
        595                 600                 605

Pro Leu Thr Leu Glu Asp Phe Lys Phe Leu Ala Val Leu Gly Arg Gly
    610                 615                 620

His Phe Gly Lys Val Leu Leu Ser Glu Phe Arg Pro Ser Gly Glu Leu
625                 630                 635                 640

Phe Ala Ile Lys Ala Leu Lys Lys Gly Asp Ile Val Ala Arg Asp Glu
                645                 650                 655

Val Glu Ser Leu Met Cys Glu Lys Arg Ile Leu Ala Ala Val Thr Ser
            660                 665                 670

Ala Gly His Pro Phe Leu Val Asn Leu Phe Gly Cys Phe Gln Thr Pro
        675                 680                 685

Glu His Val Cys Phe Val Met Glu Tyr Ser Ala Gly Gly Asp Leu Met
    690                 695                 700

Leu His Ile His Ser Asp Val Phe Ser Glu Pro Arg Ala Ile Phe Tyr
705                 710                 715                 720

Ser Ala Cys Val Val Leu Gly Leu Gln Phe Leu His Glu His Lys Ile
                725                 730                 735

Val Tyr Arg Asp Leu Lys Leu Asp Asn Leu Leu Leu Asp Thr Glu Gly
            740                 745                 750

Tyr Val Lys Ile Ala Asp Phe Gly Leu Cys Lys Glu Gly Met Gly Tyr
        755                 760                 765

Gly Asp Arg Thr Ser Thr Phe Cys Gly Thr Pro Glu Phe Leu Ala Pro
    770                 775                 780

Glu Val Leu Thr Asp Thr Ser Tyr Thr Arg Ala Val Asp Trp Trp Gly
785                 790                 795                 800

Leu Gly Val Leu Leu Tyr Glu Met Leu Val Gly Glu Ser Pro Phe Pro
                805                 810                 815

Gly Asp Asp Glu Glu Glu Val Phe Asp Ser Ile Val Asn Asp Glu Val
            820                 825                 830

Arg Tyr Pro Arg Phe Leu Ser Ala Glu Ala Ile Gly Ile Met Arg Arg
        835                 840                 845

Leu Leu Arg Arg Asn Pro Glu Arg Arg Leu Gly Ser Ser Glu Arg Asp
    850                 855                 860

Ala Glu Asp Val Lys Lys Gln Pro Phe Phe Arg Thr Leu Gly Trp Glu
865                 870                 875                 880

Ala Leu Leu Ala Arg Arg Leu Pro Pro Pro Phe Val Pro Thr Leu Ser
                885                 890                 895

Gly Arg Thr Asp Val Ser Asn Phe Asp Glu Glu Phe Thr Gly Glu Ala
            900                 905                 910

Pro Thr Leu Ser Pro Pro Arg Asp Ala Arg Pro Leu Thr Ala Ala Glu
        915                 920                 925
```

```
Gln Ala Ala Phe Leu Asp Phe Asp Phe Val Ala Gly Gly Cys
        930             935             940

<210> SEQ ID NO 17
<211> LENGTH: 1631
<212> TYPE: DNA
<213> ORGANISM: Homo sapiens
<220> FEATURE:
<221> NAME/KEY: CDS
<222> LOCATION: (42)..(1007)
<223> OTHER INFORMATION:

<400> SEQUENCE: 17
gaaaacaggc cgcgcgggcg gcagaggagc cgggcgccgc a atg gac gtg cgg gcg    56
                                             Met Asp Val Arg Ala
                                              1               5 ctg ccg tgg ctg ccg tgg ctg ctg tgg ctg ctg tgc cgg ggc ggc ggc    104
Leu Pro Trp Leu Pro Trp Leu Leu Trp Leu Leu Cys Arg Gly Gly Gly
             10                  15                  20 gat gcg gac tcc cgc gcc ccc ttc acc ccg acc tgg ccg cgg agc cgc    152
Asp Ala Asp Ser Arg Ala Pro Phe Thr Pro Thr Trp Pro Arg Ser Arg
         25                  30                  35 gag cgt gaa gcc gcc gcc ttc cgg gaa agt ctt aat aga cat cga tac    200
Glu Arg Glu Ala Ala Ala Phe Arg Glu Ser Leu Asn Arg His Arg Tyr
     40                  45                  50 ttg aat tct tta ttt ccc agt gaa aac tcc acc gcc ttc tat gga ata    248
Leu Asn Ser Leu Phe Pro Ser Glu Asn Ser Thr Ala Phe Tyr Gly Ile
 55                  60                  65 aat cag ttt tcc tat ttg ttt cct gaa gag ttt aaa gcc att tat tta    296
Asn Gln Phe Ser Tyr Leu Phe Pro Glu Glu Phe Lys Ala Ile Tyr Leu
 70                  75                  80                  85 aga agc aaa cct tcc aag ttt ccc aga tac tca gca gaa gta cat atg    344
Arg Ser Lys Pro Ser Lys Phe Pro Arg Tyr Ser Ala Glu Val His Met
                 90                  95                 100 tcc atc ccc aat gtg tct ttg ccg tta aga ttt gac tgg agg gac aag    392
Ser Ile Pro Asn Val Ser Leu Pro Leu Arg Phe Asp Trp Arg Asp Lys
            105                 110                 115 cag gtt gtg aca caa gtg aga aac cag cag atg tgt gga gga tgc tgg    440
Gln Val Val Thr Gln Val Arg Asn Gln Gln Met Cys Gly Gly Cys Trp
        120                 125                 130 gcc ttc agc gtg gtg ggg gca gtg gaa tct gct tat gca ata aag ggg    488
Ala Phe Ser Val Val Gly Ala Val Glu Ser Ala Tyr Ala Ile Lys Gly
    135                 140                 145 aag ccc ctg gaa gac cta agt gtc cag cag gtc att gac tgt tcg tat    536
Lys Pro Leu Glu Asp Leu Ser Val Gln Gln Val Ile Asp Cys Ser Tyr
150                 155                 160                 165 aat aat tat ggc tgc aat gga ggc tct act ctc aat gct ttg aac tgg    584
Asn Asn Tyr Gly Cys Asn Gly Gly Ser Thr Leu Asn Ala Leu Asn Trp
                170                 175                 180 tta aac aag atg caa gta aaa ctg gtg aaa gat tca gaa tat cct ttt    632
Leu Asn Lys Met Gln Val Lys Leu Val Lys Asp Ser Glu Tyr Pro Phe
            185                 190                 195 aaa gca caa aat ggt ctg tgc cat tac ttt tct ggt tca cat tct gga    680
Lys Ala Gln Asn Gly Leu Cys His Tyr Phe Ser Gly Ser His Ser Gly
        200                 205                 210 ttt tca atc aaa ggt tat tct gca tat gac ttc agt gac caa gaa gat    728
Phe Ser Ile Lys Gly Tyr Ser Ala Tyr Asp Phe Ser Asp Gln Glu Asp
    215                 220                 225 gaa atg gca aaa gca ctt ctt acc ttt ggc cct ttg gta gtc ata gta    776
Glu Met Ala Lys Ala Leu Leu Thr Phe Gly Pro Leu Val Val Ile Val
230                 235                 240                 245
```

```
gat gca gtg agc tgg caa gat tat ctg gga ggc att ata cag cat cac      824
Asp Ala Val Ser Trp Gln Asp Tyr Leu Gly Gly Ile Ile Gln His His
            250                 255                 260 tgc tct agt gga gaa gca aat cat gca gtt ctc ata act ggg ttt gat      872
Cys Ser Ser Gly Glu Ala Asn His Ala Val Leu Ile Thr Gly Phe Asp
265                 270                 275 aaa aca gga agc act cca tat tgg att gtg cgg aat tcc tgg gga agt      920
Lys Thr Gly Ser Thr Pro Tyr Trp Ile Val Arg Asn Ser Trp Gly Ser
        280                 285                 290 tct tgg gga gta gat ggt tat gcc cat gtc aaa atg gga agt aat gtt      968
Ser Trp Gly Val Asp Gly Tyr Ala His Val Lys Met Gly Ser Asn Val
    295                 300                 305 tgt ggt att gca gat tcc gtt tct tct ata ttt gtg tga catgttgggc      1017
Cys Gly Ile Ala Asp Ser Val Ser Ser Ile Phe Val
310                 315                 320 agatcaagag acagctacaa aaatgaaggt tttcataatg caatgtaaca tagtacttca   1077
aagtattatt caacttcaag tttcagcaac tacctacaaa agattctaag gcctagtagt   1137
atttaaacta gtttcagaa tgttcccttc ttgtagagag atggacaacc aaagtcagtg    1197
ggacaaactc cagcacagaa gcctgcgagg aagcctatgg aatagtttcc tgtcctgaga   1257
cgaaattcag attaggagat attttaggcc cctgcaactg gggaaggcta ctgtttgttt   1317
ttgtttgctt attatttatt tgtttgttta tgtgagata tttcaggtgg atcaaagag    1377 gtcataagaa tttattttct tttgtggggt gtaactacta gctttagatt accccctac   1437 acaagaatgg ccaacctaaa attatgtgtg tcttgtacag ttagttatat tagcagccct  1497
ctgagatggc gtatctatcg gaaggatttc aaacaccaat tgctttacct gaacaaatgg  1557
tgcttaccct ttgaacagca gagtgaccac gtagaaggaa ggaaaagggc aaaatcgctt  1617
cagttaaact gaaa                                                     1631

<210> SEQ ID NO 18
<211> LENGTH: 321
<212> TYPE: PRT
<213> ORGANISM: Homo sapiens

<400> SEQUENCE: 18

Met Asp Val Arg Ala Leu Pro Trp Leu Pro Trp Leu Leu Trp Leu Leu
1               5                   10                  15

Cys Arg Gly Gly Gly Asp Ala Asp Ser Arg Ala Pro Phe Thr Pro Thr
            20                  25                  30

Trp Pro Arg Ser Arg Glu Arg Glu Ala Ala Ala Phe Arg Glu Ser Leu
        35                  40                  45

Asn Arg His Arg Tyr Leu Asn Ser Leu Phe Pro Ser Glu Asn Ser Thr
    50                  55                  60

Ala Phe Tyr Gly Ile Asn Gln Phe Ser Tyr Leu Phe Pro Glu Glu Phe
65                  70                  75                  80

Lys Ala Ile Tyr Leu Arg Ser Lys Pro Ser Lys Phe Pro Arg Tyr Ser
                85                  90                  95

Ala Glu Val His Met Ser Ile Pro Asn Val Ser Leu Pro Leu Arg Phe
            100                 105                 110

Asp Trp Arg Asp Lys Gln Val Val Thr Gln Val Arg Asn Gln Gln Met
        115                 120                 125

Cys Gly Gly Cys Trp Ala Phe Ser Val Val Gly Ala Val Glu Ser Ala
    130                 135                 140

Tyr Ala Ile Lys Gly Lys Pro Leu Glu Asp Leu Ser Val Gln Gln Val
145                 150                 155                 160
```

```
Ile Asp Cys Ser Tyr Asn Asn Tyr Gly Cys Asn Gly Gly Ser Thr Leu
            165                 170                 175

Asn Ala Leu Asn Trp Leu Asn Lys Met Gln Val Lys Leu Val Lys Asp
        180                 185                 190

Ser Glu Tyr Pro Phe Lys Ala Gln Asn Gly Leu Cys His Tyr Phe Ser
    195                 200                 205

Gly Ser His Ser Gly Phe Ser Ile Lys Gly Tyr Ser Ala Tyr Asp Phe
210                 215                 220

Ser Asp Gln Glu Asp Glu Met Ala Lys Ala Leu Leu Thr Phe Gly Pro
225                 230                 235                 240

Leu Val Val Ile Val Asp Ala Val Ser Trp Gln Asp Tyr Leu Gly Gly
                245                 250                 255

Ile Ile Gln His His Cys Ser Ser Gly Glu Ala Asn His Ala Val Leu
                260                 265                 270

Ile Thr Gly Phe Asp Lys Thr Gly Ser Thr Pro Tyr Trp Ile Val Arg
            275                 280                 285

Asn Ser Trp Gly Ser Ser Trp Gly Val Asp Gly Tyr Ala His Val Lys
        290                 295                 300

Met Gly Ser Asn Val Cys Gly Ile Ala Asp Ser Val Ser Ile Phe
305                 310                 315                 320

Val
```

<210> SEQ ID NO 19
<211> LENGTH: 1159
<212> TYPE: DNA
<213> ORGANISM: Homo sapiens
<220> FEATURE:
<221> NAME/KEY: CDS
<222> LOCATION: (7)..(1062)
<223> OTHER INFORMATION:

<400> SEQUENCE: 19

```
gcccag atg gtc atc atg ggc cag tgc tac tac aac gag acc atc ggc         48
       Met Val Ile Met Gly Gln Cys Tyr Tyr Asn Glu Thr Ile Gly
       1               5                   10 ttc ttc tat aac aac agt ggc aaa gag ctc agc tcc cac tgg cgg ccc        96
Phe Phe Tyr Asn Asn Ser Gly Lys Glu Leu Ser Ser His Trp Arg Pro
15              20                  25                  30 aag gat gtg gtc gtg gtg gca ctg ggg ctg acc gtc agc gtg ctg gtg       144
Lys Asp Val Val Val Val Ala Leu Gly Leu Thr Val Ser Val Leu Val
                35                  40                  45 ctg ctg acc aat ctg ctg gtc ata gca gcc atc gcc tcc aac cgc cgc       192
Leu Leu Thr Asn Leu Leu Val Ile Ala Ala Ile Ala Ser Asn Arg Arg
            50                  55                  60 ttc cac cag ccc atc tac tac ctg ctc ggc aat ctg gcc gcg gct gac       240
Phe His Gln Pro Ile Tyr Tyr Leu Leu Gly Asn Leu Ala Ala Ala Asp
        65                  70                  75 ctc ttc gcg ggc gtg gcc tac ctc ttc ctc atg ttc cac act ggt ccc       288
Leu Phe Ala Gly Val Ala Tyr Leu Phe Leu Met Phe His Thr Gly Pro
    80                  85                  90 cgc aca gcc cga ctt tca ctt gag ggc tgg ttc ctg cgg cag ggc ttg       336
Arg Thr Ala Arg Leu Ser Leu Glu Gly Trp Phe Leu Arg Gln Gly Leu
95                  100                 105                 110 ctg gac aca agc ctc act gcg tcg gtg gcc aca ctg ctg gcc atc gcc       384
Leu Asp Thr Ser Leu Thr Ala Ser Val Ala Thr Leu Leu Ala Ile Ala
                115                 120                 125 gtg gag cgg cac cgc agt gtg atg gcc gtg cag ctg cac agc cgc ctg       432
Val Glu Arg His Arg Ser Val Met Ala Val Gln Leu His Ser Arg Leu
```

```
                        130                 135                 140
ccc cgt ggc cgc gtg gtc atg ctc att gtg ggc gtg tgg gtg gct gcc        480
Pro Arg Gly Arg Val Val Met Leu Ile Val Gly Val Trp Val Ala Ala
        145                 150                 155 ctg ggc ctg ggg ctg ctg cct gcc cac tcc tgg cac tgc ctc tgt gcc        528
Leu Gly Leu Gly Leu Leu Pro Ala His Ser Trp His Cys Leu Cys Ala
160                 165                 170 ctg gac cgc tgc tca cgc atg gca ccc ctg ctc agc cgc tcc tat ttg        576
Leu Asp Arg Cys Ser Arg Met Ala Pro Leu Leu Ser Arg Ser Tyr Leu
175                 180                 185                 190 gcc gtc tgg gct ctg tcg agc ctg ctt gtc ttc ctc atg gtg gct            624
Ala Val Trp Ala Leu Ser Ser Leu Leu Val Phe Leu Leu Met Val Ala
                195                 200                 205 gtg tac acc cgc att ttc ttc tac gtg cgg cgg cga gtg cag cgc atg        672
Val Tyr Thr Arg Ile Phe Phe Tyr Val Arg Arg Arg Val Gln Arg Met
            210                 215                 220 gca gag cat gtc agc tgc cac ccc cgc tac cga gag acc acg ctc agc        720
Ala Glu His Val Ser Cys His Pro Arg Tyr Arg Glu Thr Thr Leu Ser
        225                 230                 235 ctg gtc aag act gtt gtc atc atc ctg ggg gcg ttc gtg gtc tgc tgg        768
Leu Val Lys Thr Val Val Ile Ile Leu Gly Ala Phe Val Val Cys Trp
    240                 245                 250 aca cca ggc cag gtg gta ctg ctc ctg gat ggt tta ggc tgt gag tcc        816
Thr Pro Gly Gln Val Val Leu Leu Leu Asp Gly Leu Gly Cys Glu Ser
255                 260                 265                 270 tgc aat gtc ctg gct gta gaa aag tac ttc cta ctg ttg gcc gag gcc        864
Cys Asn Val Leu Ala Val Glu Lys Tyr Phe Leu Leu Leu Ala Glu Ala
                275                 280                 285 aac tca ctg gtc aat gct gct gtg tac tct tgc cga gat gct gag atg        912
Asn Ser Leu Val Asn Ala Ala Val Tyr Ser Cys Arg Asp Ala Glu Met
            290                 295                 300 cgc cgc acc ttc cgc cgc ctt ctc tgc tgc gcg tgc ctc cgc cag tcc        960
Arg Arg Thr Phe Arg Arg Leu Leu Cys Cys Ala Cys Leu Arg Gln Ser
305                 310                 315 acc cgc gag tct gtc cac tat aca tcc tct gcc cag gga ggt gcc agc       1008
Thr Arg Glu Ser Val His Tyr Thr Ser Ser Ala Gln Gly Gly Ala Ser
320                 325                 330 act cgc atc atg ctt ccc gag aac ggc cac cca ctg atg gac tcc acc       1056
Thr Arg Ile Met Leu Pro Glu Asn Gly His Pro Leu Met Asp Ser Thr
335                 340                 345                 350 ctt tag ctaccttgaa cttcagcggt acgcggcaag caacaaatcc acagcccctg        1112
Leu atgacttgtg ggtgctcctg gctcaaccca accaacagga ctgactg                   1159

<210> SEQ ID NO 20
<211> LENGTH: 351
<212> TYPE: PRT
<213> ORGANISM: Homo sapiens

<400> SEQUENCE: 20

Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
            20                  25                  30

Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60
```

```
Gln Pro Ile Tyr Tyr Leu Leu Gly Asn Leu Ala Ala Asp Leu Phe
 65                  70                  75                  80

Ala Gly Val Ala Tyr Leu Phe Leu Met Phe His Thr Gly Pro Arg Thr
                 85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190

Trp Ala Leu Ser Ser Leu Leu Val Phe Leu Leu Met Val Ala Val Tyr
        195                 200                 205

Thr Arg Ile Phe Phe Tyr Val Arg Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Val Cys Trp Thr Pro
                245                 250                 255

Gly Gln Val Val Leu Leu Leu Asp Gly Leu Gly Cys Glu Ser Cys Asn
            260                 265                 270

Val Leu Ala Val Glu Lys Tyr Phe Leu Leu Leu Ala Glu Ala Asn Ser
        275                 280                 285

Leu Val Asn Ala Ala Val Tyr Ser Cys Arg Asp Ala Glu Met Arg Arg
    290                 295                 300

Thr Phe Arg Arg Leu Leu Cys Cys Ala Cys Leu Arg Gln Ser Thr Arg
305                 310                 315                 320

Glu Ser Val His Tyr Thr Ser Ser Ala Gln Gly Gly Ala Ser Thr Arg
                325                 330                 335

Ile Met Leu Pro Glu Asn Gly His Pro Leu Met Asp Ser Thr Leu
            340                 345                 350

<210> SEQ ID NO 21
<211> LENGTH: 1682
<212> TYPE: DNA
<213> ORGANISM: Homo sapiens

<400> SEQUENCE: 21
tgccgagcag gacctgccct tctgcaaagg agacgtgctc accattgtgg ccgtcaccaa    60
ggaccccaac tggtacaaag ccaaaaacaa ggtgggccgt gagggcatca tcccagccaa   120
ctacgtccag aagcgggagg gcgtgaaggc gggtaccaaa ctcagcctca tgccttggtt   180
ccacggcaag atcacacggg agcaggctga gcggcttctg tacccgccgg agacaggcct   240
gttcctggtg cgggagagca ccaactaccc ggagactac acgctgtgcg tgagctgcga   300
cggcaaggtg gagcactacc gcatcatgta ccatgccagc aagctcagca tcgacgagga   360
ggtgtacttt gagaacctca tgcagctggt ggagcactac acctcagacg cagatggact   420
ctgtacgcgc ctcattaaac caaaggtcat ggagggcaca gtggcggccc aggatgagtt   480
ctaccgcagc ggctgggccc tgaacatgaa ggagctgaag ctgctgcaga ccatcgggaa   540
```

-continued

```
gggggagttc ggagacgtga tgctgggcga ttaccgaggg aacaaagtcg ccgtcaagtg      600
cattaagaac gacgccactg cccaggcctt cctggctgaa gcctcagtca tgacgcaact      660
gcggcatagc aacctggtgc agctcctggg cgtgatcgtg gaggagaagg gcgggctcta      720
catcgtcact gagtacatgg ccaaggggag ccttgtggac tacctgcggt ctaggggtcg      780
gtcagtgctg ggcggagact gtctcctcaa gttctcgcta gatgtctgcg aggccatgga      840
atacctggag ggcaacaatt tcgtgcatcg agacctggct gcccgcaatg tgctggtgtc      900
tgaggacaac gtggccaagg tcagcgactt tggtctcacc aaggaggcgt ccagcaccca      960
ggacacgggc aagctgccag tcaagtggac agcccctgag gccctgagag agaagaaatt     1020
ctccactaag tctgacgtgt ggagtttcgg aatccttctc tgggaaatct actcctttgg     1080
gcgagtgcct tatccaagaa ttcccctgaa ggacgtcgtc cctcgggtgg agaagggcta     1140
caagatggat gccccccgacg gctgcccgcc cgcagtctat gaagtcatga gaactgctg      1200
gcacctggac gccgccatgc ggccctcctt cctacagctc cgagagcagc ttgagcacat     1260
caaaacccac gagctgcacc tgtgacggct ggcctccgcc tgggtcatgg gcctgtgggg     1320
actgaacctg gaagatcatg gacctggtgc ccctgctcac tgggcccgag cctgaactga     1380
gccccagcgg gctggcgggc cttttttcctg cgtcccagcc tgcacccctc cggccccgtc     1440
tctcttggac ccacctgtgg ggcctgggga gcccactgag gggccaggga ggaaggaggc     1500
cacggagcgg gaggcagcgc cccaccacgt cgggcttccc tggcctcccg ccactcgcct     1560
tcttagagtt ttattccttt ccttttttga gattttttt ccgtgtgttt attttttatt      1620
atttttcaag ataaggagaa agaaagtacc cagcaaatgg gcattttaaa aaaaaaaaaa     1680
aa                                                                    1682
```

<210> SEQ ID NO 22
<211> LENGTH: 3328
<212> TYPE: DNA
<213> ORGANISM: Homo sapiens
<220> FEATURE:
<221> NAME/KEY: CDS
<222> LOCATION: (75)..(3098)
<223> OTHER INFORMATION:

<400> SEQUENCE: 22

```
gtttaaaatt atccaactgc catagagcta aattcttttt tggaaaattg aaccgaactt       60
ctactgaata caag atg aaa atg tgg ttg ctg gtc agt cat ctt gtg ata        110
             Met Lys Met Trp Leu Leu Val Ser His Leu Val Ile
              1               5                  10 ata tct att act acc tgt tta gca gtt tct gag gaa gac aaa gga ttt       158
Ile Ser Ile Thr Thr Cys Leu Ala Val Ser Glu Glu Asp Lys Gly Phe
         15                  20                  25 gga cca att ttt gaa gag cag cca atc aat acc att tat cca gag gaa       206
Gly Pro Ile Phe Glu Glu Gln Pro Ile Asn Thr Ile Tyr Pro Glu Glu
     30                  35                  40 tca ctg gaa gga aaa gtc tca ctc aac tgt agg gca cga gcc agc cct       254
Ser Leu Glu Gly Lys Val Ser Leu Asn Cys Arg Ala Arg Ala Ser Pro
 45                  50                  55                  60 ttc ccg gtt tac aaa tgg aga atg aat aat ggg gac gtt gat ctc aca       302
Phe Pro Val Tyr Lys Trp Arg Met Asn Asn Gly Asp Val Asp Leu Thr
                 65                  70                  75 agt gat cga tac agt atg gta gga gga aac ctt gtt atc aac aac cct       350
Ser Asp Arg Tyr Ser Met Val Gly Gly Asn Leu Val Ile Asn Asn Pro
         80                  85                  90
```

-continued

| | | |
|---|---|---|
| gac aaa cag aaa gat gct gga ata tac tac tgt tta gca tct aat aac<br>Asp Lys Gln Lys Asp Ala Gly Ile Tyr Tyr Cys Leu Ala Ser Asn Asn<br>       95                     100                 105 | | 398 |
| tac ggg atg gtc aga agc act gaa gca acc ctg agc ttt gga tat ctt<br>Tyr Gly Met Val Arg Ser Thr Glu Ala Thr Leu Ser Phe Gly Tyr Leu<br>  110                   115                120 | | 446 |
| gat cct ttc cca cct gag gaa cgt cct gag gtc aga gta aaa gaa ggg<br>Asp Pro Phe Pro Pro Glu Glu Arg Pro Glu Val Arg Val Lys Glu Gly<br>125               130                135              140 | | 494 |
| aaa gga atg gtg ctt ctc tgt gac ccc cca tac cat ttt cca gat gat<br>Lys Gly Met Val Leu Leu Cys Asp Pro Pro Tyr His Phe Pro Asp Asp<br>               145                150              155 | | 542 |
| ctt agc tat cgc tgg ctt cta aat gaa ttt cct gta ttt atc aca atg<br>Leu Ser Tyr Arg Trp Leu Leu Asn Glu Phe Pro Val Phe Ile Thr Met<br>         160                  165              170 | | 590 |
| gat aaa cgg cga ttt gtg tct cag aca aat ggc aat ctc tac att gca<br>Asp Lys Arg Arg Phe Val Ser Gln Thr Asn Gly Asn Leu Tyr Ile Ala<br>       175                 180              185 | | 638 |
| aat gtt gag gct tcc gac aaa ggc aat tat tcc tgc ttt gtt tcc agt<br>Asn Val Glu Ala Ser Asp Lys Gly Asn Tyr Ser Cys Phe Val Ser Ser<br>   190                 195              200 | | 686 |
| cct tct att aca aag agc gtg ttc agc aaa ttc atc cca ctc att cca<br>Pro Ser Ile Thr Lys Ser Val Phe Ser Lys Phe Ile Pro Leu Ile Pro<br>205               210                215              220 | | 734 |
| ata cct gaa cga aca aca aaa cca tat cct gct gat att gta gtt cag<br>Ile Pro Glu Arg Thr Thr Lys Pro Tyr Pro Ala Asp Ile Val Val Gln<br>               225                230              235 | | 782 |
| ttc aag gat gta tat gca ttg atg ggc caa aat gtg acc tta gaa tgt<br>Phe Lys Asp Val Tyr Ala Leu Met Gly Gln Asn Val Thr Leu Glu Cys<br>         240                  245              250 | | 830 |
| ttt gca ctt gga aat cct gtt ccg gat atc cga tgg cgg aag gtt cta<br>Phe Ala Leu Gly Asn Pro Val Pro Asp Ile Arg Trp Arg Lys Val Leu<br>       255                 260              265 | | 878 |
| gaa cca atg cca agc act gct gag att agc acc tct ggg gct gtt ctt<br>Glu Pro Met Pro Ser Thr Ala Glu Ile Ser Thr Ser Gly Ala Val Leu<br>   270                 275              280 | | 926 |
| aag atc ttc aat att cag cta gaa gat gaa ggc ata tat gaa tgt gag<br>Lys Ile Phe Asn Ile Gln Leu Glu Asp Glu Gly Ile Tyr Glu Cys Glu<br>285               290                295              300 | | 974 |
| gct gag aac att aga gga aag gat aaa cat caa gca aga att tat gtt<br>Ala Glu Asn Ile Arg Gly Lys Asp Lys His Gln Ala Arg Ile Tyr Val<br>               305                310              315 | | 1022 |
| caa gca ttc cct gag tgg gta gaa cac atc aat gac aca gag gtg gac<br>Gln Ala Phe Pro Glu Trp Val Glu His Ile Asn Asp Thr Glu Val Asp<br>         320                  325              330 | | 1070 |
| ata ggc agt gat ctc tac tgg cct tgt gtg gcc aca gga aag ccc atc<br>Ile Gly Ser Asp Leu Tyr Trp Pro Cys Val Ala Thr Gly Lys Pro Ile<br>       335                 340              345 | | 1118 |
| cct aca atc cga tgg ttg aaa aat gga tat gcg tat cat aaa ggg gaa<br>Pro Thr Ile Arg Trp Leu Lys Asn Gly Tyr Ala Tyr His Lys Gly Glu<br>   350                 355              360 | | 1166 |
| tta aga ctg tat gat gtg act ttt gaa aat gcc gga atg tat cag tgc<br>Leu Arg Leu Tyr Asp Val Thr Phe Glu Asn Ala Gly Met Tyr Gln Cys<br>365               370                375              380 | | 1214 |
| ata gct gaa aac aca tat gga gcc att tat gca aat gct gag ttg aag<br>Ile Ala Glu Asn Thr Tyr Gly Ala Ile Tyr Ala Asn Ala Glu Leu Lys<br>               385                390              395 | | 1262 |
| atc ttg gcg ttg gct cca act ttt gaa atg aat cct atg aag aaa aag<br>Ile Leu Ala Leu Ala Pro Thr Phe Glu Met Asn Pro Met Lys Lys Lys<br>         400                  405              410 | | 1310 |

-continued

| | | |
|---|---|---|
| atc ctg gct gct aaa ggt gga agg gtg ata att gaa tgc aaa cct aaa<br>Ile Leu Ala Ala Lys Gly Gly Arg Val Ile Ile Glu Cys Lys Pro Lys<br>415　　　　　　　420　　　　　　　425 | | 1358 |
| gct gca ccg aaa cca aag ttt tca tgg agt aaa ggg aca gag tgg ctt<br>Ala Ala Pro Lys Pro Lys Phe Ser Trp Ser Lys Gly Thr Glu Trp Leu<br>430　　　　　　　435　　　　　　　440 | | 1406 |
| gtc aat agc agc aga ata ctc att tgg gaa gat ggt agc ttg gaa atc<br>Val Asn Ser Ser Arg Ile Leu Ile Trp Glu Asp Gly Ser Leu Glu Ile<br>445　　　　　　　450　　　　　　　455　　　　　　　460 | | 1454 |
| aac aac att aca agg aat gat gga ggt atc tat aca tgc ttt gca gaa<br>Asn Asn Ile Thr Arg Asn Asp Gly Gly Ile Tyr Thr Cys Phe Ala Glu<br>465　　　　　　　470　　　　　　　475 | | 1502 |
| aat aac aga ggg aaa gct aat agc act gga acc ctt gtt atc aca gat<br>Asn Asn Arg Gly Lys Ala Asn Ser Thr Gly Thr Leu Val Ile Thr Asp<br>480　　　　　　　485　　　　　　　490 | | 1550 |
| cct acg cga att ata ttg gcc cca att aat gcc gat atc aca gtt gga<br>Pro Thr Arg Ile Ile Leu Ala Pro Ile Asn Ala Asp Ile Thr Val Gly<br>495　　　　　　　500　　　　　　　505 | | 1598 |
| gaa aac gcc acc atg cag tgt gct gcg tcc ttt gat cct gcc ttg gat<br>Glu Asn Ala Thr Met Gln Cys Ala Ala Ser Phe Asp Pro Ala Leu Asp<br>510　　　　　　　515　　　　　　　520 | | 1646 |
| ctc aca ttt gtt tgg tcc ttc aat ggc tat gtg atc gat ttt aac aaa<br>Leu Thr Phe Val Trp Ser Phe Asn Gly Tyr Val Ile Asp Phe Asn Lys<br>525　　　　　　　530　　　　　　　535　　　　　　　540 | | 1694 |
| gag aat att cac tac cag agg aat ttt atg ctg gat tcc aat ggg gaa<br>Glu Asn Ile His Tyr Gln Arg Asn Phe Met Leu Asp Ser Asn Gly Glu<br>545　　　　　　　550　　　　　　　555 | | 1742 |
| tta cta atc cga aat gcg cag ctg aaa cat gct gga aga tac aca tgc<br>Leu Leu Ile Arg Asn Ala Gln Leu Lys His Ala Gly Arg Tyr Thr Cys<br>560　　　　　　　565　　　　　　　570 | | 1790 |
| act gcc cag aca att gtg gac aat tct tca gct tca gct gac ctt gta<br>Thr Ala Gln Thr Ile Val Asp Asn Ser Ser Ala Ser Ala Asp Leu Val<br>575　　　　　　　580　　　　　　　585 | | 1838 |
| gtg aga ggc cct cca ggc cct cca ggt ggt ctg aga ata gaa gac att<br>Val Arg Gly Pro Pro Gly Pro Pro Gly Gly Leu Arg Ile Glu Asp Ile<br>590　　　　　　　595　　　　　　　600 | | 1886 |
| aga gcc act tct gtg gca ctt act tgg agc cgt ggt tca gac aat cat<br>Arg Ala Thr Ser Val Ala Leu Thr Trp Ser Arg Gly Ser Asp Asn His<br>605　　　　　　　610　　　　　　　615　　　　　　　620 | | 1934 |
| agt cct att tct aaa tac act atc cag acc aag act att ctt tca gat<br>Ser Pro Ile Ser Lys Tyr Thr Ile Gln Thr Lys Thr Ile Leu Ser Asp<br>625　　　　　　　630　　　　　　　635 | | 1982 |
| gac tgg aaa gat gca aag aca gat ccc cca att att gaa gga aat atg<br>Asp Trp Lys Asp Ala Lys Thr Asp Pro Pro Ile Ile Glu Gly Asn Met<br>640　　　　　　　645　　　　　　　650 | | 2030 |
| gag gca gca aga gca gtg gac tta atc cca tgg atg gag tat gaa ttc<br>Glu Ala Ala Arg Ala Val Asp Leu Ile Pro Trp Met Glu Tyr Glu Phe<br>655　　　　　　　660　　　　　　　665 | | 2078 |
| cgc gta gta gca acc aat aca ctg ggt aga gga gag ccc agt ata cca<br>Arg Val Val Ala Thr Asn Thr Leu Gly Arg Gly Glu Pro Ser Ile Pro<br>670　　　　　　　675　　　　　　　680 | | 2126 |
| tct aac aga att aaa aca gac ggt gct gca cca aat gtg gct cct tca<br>Ser Asn Arg Ile Lys Thr Asp Gly Ala Ala Pro Asn Val Ala Pro Ser<br>685　　　　　　　690　　　　　　　695　　　　　　　700 | | 2174 |
| gat gta gga ggt gga ggt gga aga aac aga gag ctg acc ata aca tgg<br>Asp Val Gly Gly Gly Gly Gly Arg Asn Arg Glu Leu Thr Ile Thr Trp<br>705　　　　　　　710　　　　　　　715 | | 2222 |
| gcg cct ttg tca aga gaa tac cac tat ggc aac aat ttt ggt tac ata<br>Ala Pro Leu Ser Arg Glu Tyr His Tyr Gly Asn Asn Phe Gly Tyr Ile | | 2270 |

```
                    720              725              730
gtg gca ttt aag cca ttt gat gga gaa gaa tgg aaa aaa gtc aca gtt    2318
Val Ala Phe Lys Pro Phe Asp Gly Glu Glu Trp Lys Lys Val Thr Val
        735              740              745 act aat cct gat act ggc cga tat gtc cat aaa gat gaa acc atg agc    2366
Thr Asn Pro Asp Thr Gly Arg Tyr Val His Lys Asp Glu Thr Met Ser
750              755              760 cct tcc act gca ttt caa gtt aaa gtc aag gcc ttc aac aac aaa gga    2414
Pro Ser Thr Ala Phe Gln Val Lys Val Lys Ala Phe Asn Asn Lys Gly
765              770              775              780 gat gga cct tac agc cta gta gca gtc att aat tca gca caa gac gct    2462
Asp Gly Pro Tyr Ser Leu Val Ala Val Ile Asn Ser Ala Gln Asp Ala
            785              790              795 ccc agt gaa gcc cca aca gaa gta ggt gta aaa gtc tta tca tct tct    2510
Pro Ser Glu Ala Pro Thr Glu Val Gly Val Lys Val Leu Ser Ser Ser
        800              805              810 gag ata tct gtt cat tgg gaa cat gtt tta gaa aaa ata gtg gaa agc    2558
Glu Ile Ser Val His Trp Glu His Val Leu Glu Lys Ile Val Glu Ser
    815              820              825 tat cag att cgg tat tgg gct gcc cat gac aaa gaa gaa gct gca aac    2606
Tyr Gln Ile Arg Tyr Trp Ala Ala His Asp Lys Glu Glu Ala Ala Asn
830              835              840 aga gtt caa gtc acc agc caa gag tac tcg gcc agg ctc gag aac ctt    2654
Arg Val Gln Val Thr Ser Gln Glu Tyr Ser Ala Arg Leu Glu Asn Leu
845              850              855              860 ctg cca gac acc cag tat ttt ata gaa gtc ggg gcc tgc aat agt gca    2702
Leu Pro Asp Thr Gln Tyr Phe Ile Glu Val Gly Ala Cys Asn Ser Ala
            865              870              875 ggg tgt gga cct cca agt gac atg att gag gct ttc acc aag aaa gca    2750
Gly Cys Gly Pro Pro Ser Asp Met Ile Glu Ala Phe Thr Lys Lys Ala
        880              885              890 cct cct agc cag cct cca agg atc atc agt tca gta agg tct ggt tca    2798
Pro Pro Ser Gln Pro Pro Arg Ile Ile Ser Ser Val Arg Ser Gly Ser
    895              900              905 cgc tat ata atc acc tgg gat cat gtc gtt gca cta tca aat gaa tct    2846
Arg Tyr Ile Ile Thr Trp Asp His Val Val Ala Leu Ser Asn Glu Ser
910              915              920 aca gtg acg gga tat aag gta ctc tac aga cct gat ggc cag cat gat    2894
Thr Val Thr Gly Tyr Lys Val Leu Tyr Arg Pro Asp Gly Gln His Asp
925              930              935              940 ggc aag ctg tat tca act cac aaa cac tcc ata gaa gtc cca atc ccc    2942
Gly Lys Leu Tyr Ser Thr His Lys His Ser Ile Glu Val Pro Ile Pro
            945              950              955 aga gat gga gaa tac gtt gtg gag gtt cgc gcg cac agt gat gga gga    2990
Arg Asp Gly Glu Tyr Val Val Glu Val Arg Ala His Ser Asp Gly Gly
        960              965              970 gat gga gtg gtg tct caa gtc aaa att tca ggt gca ccc acc cta tcc    3038
Asp Gly Val Val Ser Gln Val Lys Ile Ser Gly Ala Pro Thr Leu Ser
    975              980              985 cca agt ctt ctc ggc tta ctg ctg cct gcc ttt ggc atc ctt gtc tac    3086
Pro Ser Leu Leu Gly Leu Leu Leu Pro Ala Phe Gly Ile Leu Val Tyr
990              995              1000 ttg gaa ttc tga atgtgttgtg acagctgctg ttcccatccc agctcagaag        3138
Leu Glu Phe
1005 acacccttca accctgggat gaccacaatt ccttccaatt tctgcggctc catcctaagc   3198 caaataaatt atactttaac aaactattca actgatttac aacacacatg atgactgagg   3258 cattcgggaa ccccttcatc caaaagaata aacttttaaa tggatataaa tgattttaa    3318
```
ctcgttccaa                                                                3328

<210> SEQ ID NO 23
<211> LENGTH: 1007
<212> TYPE: PRT
<213> ORGANISM: Homo sapiens

<400> SEQUENCE: 23

Met Lys Met Trp Leu Leu Val Ser His Leu Val Ile Ile Ser Ile Thr
1               5                   10                  15

Thr Cys Leu Ala Val Ser Glu Glu Asp Lys Gly Phe Gly Pro Ile Phe
            20                  25                  30

Glu Glu Gln Pro Ile Asn Thr Ile Tyr Pro Glu Glu Ser Leu Glu Gly
        35                  40                  45

Lys Val Ser Leu Asn Cys Arg Ala Arg Ala Ser Pro Phe Pro Val Tyr
    50                  55                  60

Lys Trp Arg Met Asn Asn Gly Asp Val Asp Leu Thr Ser Asp Arg Tyr
65                  70                  75                  80

Ser Met Val Gly Gly Asn Leu Val Ile Asn Asn Pro Asp Lys Gln Lys
                85                  90                  95

Asp Ala Gly Ile Tyr Tyr Cys Leu Ala Ser Asn Asn Tyr Gly Met Val
            100                 105                 110

Arg Ser Thr Glu Ala Thr Leu Ser Phe Gly Tyr Leu Asp Pro Phe Pro
        115                 120                 125

Pro Glu Glu Arg Pro Glu Val Arg Val Lys Glu Gly Lys Gly Met Val
    130                 135                 140

Leu Leu Cys Asp Pro Pro Tyr His Phe Pro Asp Asp Leu Ser Tyr Arg
145                 150                 155                 160

Trp Leu Leu Asn Glu Phe Pro Val Phe Ile Thr Met Asp Lys Arg Arg
                165                 170                 175

Phe Val Ser Gln Thr Asn Gly Asn Leu Tyr Ile Ala Asn Val Glu Ala
            180                 185                 190

Ser Asp Lys Gly Asn Tyr Ser Cys Phe Val Ser Ser Pro Ser Ile Thr
        195                 200                 205

Lys Ser Val Phe Ser Lys Phe Ile Pro Leu Ile Pro Ile Pro Glu Arg
    210                 215                 220

Thr Thr Lys Pro Tyr Pro Ala Asp Ile Val Val Gln Phe Lys Asp Val
225                 230                 235                 240

Tyr Ala Leu Met Gly Gln Asn Val Thr Leu Glu Cys Phe Ala Leu Gly
                245                 250                 255

Asn Pro Val Pro Asp Ile Arg Trp Arg Lys Val Leu Glu Pro Met Pro
            260                 265                 270

Ser Thr Ala Glu Ile Ser Thr Ser Gly Ala Val Leu Lys Ile Phe Asn
        275                 280                 285

Ile Gln Leu Glu Asp Glu Gly Ile Tyr Glu Cys Glu Ala Glu Asn Ile
    290                 295                 300

Arg Gly Lys Asp Lys His Gln Ala Arg Ile Tyr Val Gln Ala Phe Pro
305                 310                 315                 320

Glu Trp Val Glu His Ile Asn Asp Thr Glu Val Asp Ile Gly Ser Asp
                325                 330                 335

Leu Tyr Trp Pro Cys Val Ala Thr Gly Lys Pro Ile Pro Thr Ile Arg
            340                 345                 350

Trp Leu Lys Asn Gly Tyr Ala Tyr His Lys Gly Glu Leu Arg Leu Tyr
        355                 360                 365

```
Asp Val Thr Phe Glu Asn Ala Gly Met Tyr Gln Cys Ile Ala Glu Asn
    370                 375                 380
Thr Tyr Gly Ala Ile Tyr Ala Asn Ala Glu Leu Lys Ile Leu Ala Leu
385                 390                 395                 400
Ala Pro Thr Phe Glu Met Asn Pro Met Lys Lys Ile Leu Ala Ala
            405                 410                 415
Lys Gly Gly Arg Val Ile Ile Glu Cys Lys Pro Lys Ala Ala Pro Lys
                420                 425                 430
Pro Lys Phe Ser Trp Ser Lys Gly Thr Glu Trp Leu Val Asn Ser Ser
            435                 440                 445
Arg Ile Leu Ile Trp Glu Asp Gly Ser Leu Glu Ile Asn Asn Ile Thr
        450                 455                 460
Arg Asn Asp Gly Gly Ile Tyr Thr Cys Phe Ala Glu Asn Asn Arg Gly
465                 470                 475                 480
Lys Ala Asn Ser Thr Gly Thr Leu Val Ile Thr Asp Pro Thr Arg Ile
            485                 490                 495
Ile Leu Ala Pro Ile Asn Ala Asp Ile Thr Val Gly Glu Asn Ala Thr
                500                 505                 510
Met Gln Cys Ala Ala Ser Phe Asp Pro Ala Leu Asp Leu Thr Phe Val
            515                 520                 525
Trp Ser Phe Asn Gly Tyr Val Ile Asp Phe Asn Lys Glu Asn Ile His
    530                 535                 540
Tyr Gln Arg Asn Phe Met Leu Asp Ser Asn Gly Glu Leu Leu Ile Arg
545                 550                 555                 560
Asn Ala Gln Leu Lys His Ala Gly Arg Tyr Thr Cys Thr Ala Gln Thr
                565                 570                 575
Ile Val Asp Asn Ser Ser Ala Ser Ala Asp Leu Val Val Arg Gly Pro
            580                 585                 590
Pro Gly Pro Pro Gly Gly Leu Arg Ile Glu Asp Ile Arg Ala Thr Ser
        595                 600                 605
Val Ala Leu Thr Trp Ser Arg Gly Ser Asp Asn His Ser Pro Ile Ser
610                 615                 620
Lys Tyr Thr Ile Gln Thr Lys Thr Ile Leu Ser Asp Asp Trp Lys Asp
625                 630                 635                 640
Ala Lys Thr Asp Pro Pro Ile Ile Glu Gly Asn Met Glu Ala Ala Arg
            645                 650                 655
Ala Val Asp Leu Ile Pro Trp Met Glu Tyr Glu Phe Arg Val Val Ala
            660                 665                 670
Thr Asn Thr Leu Gly Arg Gly Glu Pro Ser Ile Pro Ser Asn Arg Ile
            675                 680                 685
Lys Thr Asp Gly Ala Ala Pro Asn Val Ala Pro Ser Asp Val Gly Gly
        690                 695                 700
Gly Gly Gly Arg Asn Arg Glu Leu Thr Ile Thr Trp Ala Pro Leu Ser
705                 710                 715                 720
Arg Glu Tyr His Tyr Gly Asn Asn Phe Gly Tyr Ile Val Ala Phe Lys
                725                 730                 735
Pro Phe Asp Gly Glu Glu Trp Lys Lys Val Thr Val Thr Asn Pro Asp
            740                 745                 750
Thr Gly Arg Tyr Val His Lys Asp Glu Thr Met Ser Pro Ser Thr Ala
        755                 760                 765
Phe Gln Val Lys Val Lys Ala Phe Asn Asn Lys Gly Asp Gly Pro Tyr
770                 775                 780
```

```
Ser Leu Val Ala Val Ile Asn Ser Ala Gln Asp Ala Pro Ser Glu Ala
785                 790                 795                 800

Pro Thr Glu Val Gly Val Lys Val Leu Ser Ser Glu Ile Ser Val
            805                 810                 815

His Trp Glu His Val Leu Glu Lys Ile Val Glu Ser Tyr Gln Ile Arg
820                 825                 830

Tyr Trp Ala Ala His Asp Lys Glu Glu Ala Ala Asn Arg Val Gln Val
        835                 840                 845

Thr Ser Gln Glu Tyr Ser Ala Arg Leu Glu Asn Leu Leu Pro Asp Thr
850                 855                 860

Gln Tyr Phe Ile Glu Val Gly Ala Cys Asn Ser Ala Gly Cys Gly Pro
865                 870                 875                 880

Pro Ser Asp Met Ile Glu Ala Phe Thr Lys Lys Ala Pro Pro Ser Gln
                885                 890                 895

Pro Pro Arg Ile Ile Ser Ser Val Arg Ser Gly Ser Arg Tyr Ile Ile
            900                 905                 910

Thr Trp Asp His Val Val Ala Leu Ser Asn Glu Ser Thr Val Thr Gly
        915                 920                 925

Tyr Lys Val Leu Tyr Arg Pro Asp Gly Gln His Asp Gly Lys Leu Tyr
930                 935                 940

Ser Thr His Lys His Ser Ile Glu Val Pro Ile Pro Arg Asp Gly Glu
945                 950                 955                 960

Tyr Val Val Glu Val Arg Ala His Ser Asp Gly Gly Asp Gly Val Val
                965                 970                 975

Ser Gln Val Lys Ile Ser Gly Ala Pro Thr Leu Ser Pro Ser Leu Leu
            980                 985                 990

Gly Leu Leu Leu Pro Ala Phe Gly Ile Leu Val Tyr Leu Glu Phe
        995                 1000                1005

<210> SEQ ID NO 24
<211> LENGTH: 1622
<212> TYPE: DNA
<213> ORGANISM: Homo sapiens
<220> FEATURE:
<221> NAME/KEY: CDS
<222> LOCATION: (156)..(959)
<223> OTHER INFORMATION:

<400> SEQUENCE: 24
ggcacgaggg tgacgctggg cctgcagcgc ggagcagaaa gcagaacccg cagagtcctc     60
cctgctgctg tgtggacgac acgtgggcac aggcagaagt gggccctgtg accagctgca    120
ctggtttcgt ggaaggaagc tccaggactg gcggg atg ggc tca gcc tgt atc      173
                                       Met Gly Ser Ala Cys Ile
                                         1               5 aaa gtc acc aaa tac ttt ctc ttc ctc ttc aac ttg atc ttc ttt atc     221
Lys Val Thr Lys Tyr Phe Leu Phe Leu Phe Asn Leu Ile Phe Phe Ile
            10                  15                  20 ctg ggc gca gtg atc ctg ggc ttc ggg gtg tgg atc ctg gcc gac aag     269
Leu Gly Ala Val Ile Leu Gly Phe Gly Val Trp Ile Leu Ala Asp Lys
        25                  30                  35 agc agt ttc atc tct gtc ctg caa acc tcc tcc agc tcg ctt agg atg     317
Ser Ser Phe Ile Ser Val Leu Gln Thr Ser Ser Ser Ser Leu Arg Met
    40                  45                  50 ggg gcc tat gtc ttc atc ggc gtg ggg gca gtc act atg ctc atg ggc     365
Gly Ala Tyr Val Phe Ile Gly Val Gly Ala Val Thr Met Leu Met Gly
55                  60                  65                  70 ttc ctg ggc tgc atc ggc gcc gtc aac gag gtc cgc tgc ctg ctg ggg     413
```

```
Phe Leu Gly Cys Ile Gly Ala Val Asn Glu Val Arg Cys Leu Leu Gly
             75                  80                  85 ctg tac ttt gct ttc ctg ctc ctg atc ctc att gcc cag gtg acg gcc      461
Leu Tyr Phe Ala Phe Leu Leu Leu Ile Leu Ile Ala Gln Val Thr Ala
             90                  95                 100 ggg gcc ctc ttc tac ttc aac atg ggc aag ctg aag cag gag atg ggc      509
Gly Ala Leu Phe Tyr Phe Asn Met Gly Lys Leu Lys Gln Glu Met Gly
            105                 110                 115 ggc atc gtg act gag ctc att cga gac tac aac agc agt cgc gag gac      557
Gly Ile Val Thr Glu Leu Ile Arg Asp Tyr Asn Ser Ser Arg Glu Asp
            120                 125                 130 agc ctg cag gat gcc tgg gac tac gtg cag gct cag gtg aag tgc tgc      605
Ser Leu Gln Asp Ala Trp Asp Tyr Val Gln Ala Gln Val Lys Cys Cys
135                 140                 145                 150 ggc tgg gtc agc ttc tac aac tgg aca gac aac gct gag ctc atg aat      653
Gly Trp Val Ser Phe Tyr Asn Trp Thr Asp Asn Ala Glu Leu Met Asn
                155                 160                 165 cgc cct gag gtc acc tac ccc tgt tcc tgc gaa gtc aag ggg gaa gag      701
Arg Pro Glu Val Thr Tyr Pro Cys Ser Cys Glu Val Lys Gly Glu Glu
            170                 175                 180 gac aac agc ctt tct gtg agg aag ggc ttc tgc gag gcc ccc ggc aac      749
Asp Asn Ser Leu Ser Val Arg Lys Gly Phe Cys Glu Ala Pro Gly Asn
            185                 190                 195 agg acc cag agt ggc aac cac cct gag gac tgg cct gtg tac cag gag      797
Arg Thr Gln Ser Gly Asn His Pro Glu Asp Trp Pro Val Tyr Gln Glu
        200                 205                 210 ggc tgc atg gag aag gtg cag gcg tgg ctg cag gag aac ctg ggc atc      845
Gly Cys Met Glu Lys Val Gln Ala Trp Leu Gln Glu Asn Leu Gly Ile
215                 220                 225                 230 atc ctc ggc gtg ggc gtg ggt gtg gcc atc gtc gag ctc ctg ggg atg      893
Ile Leu Gly Val Gly Val Gly Val Ala Ile Val Glu Leu Leu Gly Met
                235                 240                 245 gtc ctg tcc atc tgc ttg tgc cgg cac gtc cat tcc gaa gac tac agc      941
Val Leu Ser Ile Cys Leu Cys Arg His Val His Ser Glu Asp Tyr Ser
            250                 255                 260 aag gtc ccc aag tac tga ggcagctgct atccccatct ccctgcctgg              989
Lys Val Pro Lys Tyr
            265 ccccaacct cagggctccc agggtctcc ctggctccct cctccaggcc tgcctcccac      1049
ttcactgcga agaccctctt gcccaccctg actgaaagta gggggctttc tggggcctag   1109
cgatctctcc tggcctatcc gctgccagcc ttgagccctg gctgttctgt ggttcctctg   1169
ctcaccgccc atcagggttc tcttagcaac tcagagaaaa atgctcccca cagcgtccct   1229
ggcgcaggtg ggctggactt ctacctgccc tcaagggtgt gtatattgta tagggcaac    1289 tgtatgaaaa attggggagg aggggccgg gcgcggtggc tcacgcctgt aatcccagca    1349
ctttgggagg ccgaggcggg tggatcacga ggtcaggaga tcgagaccat cctggctaac   1409
atggtgaaac cccgtctcta ctaaaaatac aaaaaaaatt tagccgggcg cggtggcggg   1469
cacctgtagt cccagctact tgggaggctg aggcaggaga atggtgtgaa cccgggagcg   1529
gaggttgcag tgagctgaga tcgtgctact gcactccagc ctgggggaca gaaagagact   1589
ccgtctcaaa aaaaaaaaaa aaaaaaaaa aaa                                 1622
```

<210> SEQ ID NO 25
<211> LENGTH: 267
<212> TYPE: PRT
<213> ORGANISM: Homo sapiens

```
<400> SEQUENCE: 25

Met Gly Ser Ala Cys Ile Lys Val Thr Lys Tyr Phe Leu Phe Leu Phe
1               5                   10                  15

Asn Leu Ile Phe Phe Ile Leu Gly Ala Val Ile Leu Gly Phe Gly Val
            20                  25                  30

Trp Ile Leu Ala Asp Lys Ser Ser Phe Ile Ser Val Leu Gln Thr Ser
        35                  40                  45

Ser Ser Ser Leu Arg Met Gly Ala Tyr Val Phe Ile Gly Val Gly Ala
50                  55                  60

Val Thr Met Leu Met Gly Phe Leu Gly Cys Ile Gly Ala Val Asn Glu
65                  70                  75                  80

Val Arg Cys Leu Leu Gly Leu Tyr Phe Ala Phe Leu Leu Leu Ile Leu
                85                  90                  95

Ile Ala Gln Val Thr Ala Gly Ala Leu Phe Tyr Phe Asn Met Gly Lys
            100                 105                 110

Leu Lys Gln Glu Met Gly Gly Ile Val Thr Glu Leu Ile Arg Asp Tyr
        115                 120                 125

Asn Ser Ser Arg Glu Asp Ser Leu Gln Asp Ala Trp Asp Tyr Val Gln
130                 135                 140

Ala Gln Val Lys Cys Cys Gly Trp Val Ser Phe Tyr Asn Trp Thr Asp
145                 150                 155                 160

Asn Ala Glu Leu Met Asn Arg Pro Glu Val Thr Tyr Pro Cys Ser Cys
                165                 170                 175

Glu Val Lys Gly Glu Glu Asp Asn Ser Leu Ser Val Arg Lys Gly Phe
            180                 185                 190

Cys Glu Ala Pro Gly Asn Arg Thr Gln Ser Gly Asn His Pro Glu Asp
        195                 200                 205

Trp Pro Val Tyr Gln Glu Gly Cys Met Glu Lys Val Gln Ala Trp Leu
210                 215                 220

Gln Glu Asn Leu Gly Ile Ile Leu Gly Val Gly Val Gly Val Ala Ile
225                 230                 235                 240

Val Glu Leu Leu Gly Met Val Leu Ser Ile Cys Leu Cys Arg His Val
                245                 250                 255

His Ser Glu Asp Tyr Ser Lys Val Pro Lys Tyr
            260                 265

<210> SEQ ID NO 26
<211> LENGTH: 1460
<212> TYPE: DNA
<213> ORGANISM: Homo sapiens
<220> FEATURE:
<221> NAME/KEY: CDS
<222> LOCATION: (15)..(1115)
<223> OTHER INFORMATION:

<400> SEQUENCE: 26
cctccacagg cgtc atg gcc ctc cga ttc ctc ttg ggc ttt ctg ctt gcc        50
               Met Ala Leu Arg Phe Leu Leu Gly Phe Leu Leu Ala
               1               5                   10 ggt gtt gac ctg ggt gtc tac ctg atg cgc ctg gag ctg tgc gac cca        98
Gly Val Asp Leu Gly Val Tyr Leu Met Arg Leu Glu Leu Cys Asp Pro
        15                  20                  25 acc cag agg ctt cgg gtg gcc ctg gca ggg gag ttg gtg ggg gtg gga       146
Thr Gln Arg Leu Arg Val Ala Leu Ala Gly Glu Leu Val Gly Val Gly
    30                  35                  40 ggg cac ttc ctg ttc ctg ggc ctg gcc ctt gtc tct aag gat tgg cga       194
Gly His Phe Leu Phe Leu Gly Leu Ala Leu Val Ser Lys Asp Trp Arg
```

```
                                      -continued
45                  50                  55                  60
ttc cta cag cga atg atc acc gct ccc tgc atc ctc ttc ctg ttt tat      242
Phe Leu Gln Arg Met Ile Thr Ala Pro Cys Ile Leu Phe Leu Phe Tyr
                    65                  70                  75 ggc tgg cct ggt ttg ttc ctg gag tcc gca cgg tgg ctg ata gtg aag      290
Gly Trp Pro Gly Leu Phe Leu Glu Ser Ala Arg Trp Leu Ile Val Lys
                80                  85                  90 cgg cag att gag gag gct cag tct gtg ctg agg atc ctg gct gag cga      338
Arg Gln Ile Glu Glu Ala Gln Ser Val Leu Arg Ile Leu Ala Glu Arg
            95                  100                 105 aac cgg ccc cat ggg cag atg ctg ggg gag gag gcc cag gag gcc ctg      386
Asn Arg Pro His Gly Gln Met Leu Gly Glu Glu Ala Gln Glu Ala Leu
        110                 115                 120 cag gac ctg gag aat acc tgc cct ctc cct gca aca tcc tcc ttt tcc      434
Gln Asp Leu Glu Asn Thr Cys Pro Leu Pro Ala Thr Ser Ser Phe Ser
125                 130                 135                 140 ttt gct tcc ctc ctc aac tac cgc aac atc tgg aaa aat ctg ctt atc      482
Phe Ala Ser Leu Leu Asn Tyr Arg Asn Ile Trp Lys Asn Leu Leu Ile
                    145                 150                 155 ctg ggc ttc acc aac ttc att gcc cat gcc att cgc cac tgc tac cag      530
Leu Gly Phe Thr Asn Phe Ile Ala His Ala Ile Arg His Cys Tyr Gln
                160                 165                 170 cct gtg gga gga gga ggg agc cca tcg gac ttc tac ctg tgc tct ctg      578
Pro Val Gly Gly Gly Gly Ser Pro Ser Asp Phe Tyr Leu Cys Ser Leu
            175                 180                 185 ctg gcc agc ggc acc gca gcc ctg gcc tgt gtc ttc ctg ggg gtc acc      626
Leu Ala Ser Gly Thr Ala Ala Leu Ala Cys Val Phe Leu Gly Val Thr
        190                 195                 200 gtg gac cga ttt ggc cgc cgg ggc atc ctt ctt ctc tcc atg acc ctt      674
Val Asp Arg Phe Gly Arg Arg Gly Ile Leu Leu Leu Ser Met Thr Leu
205                 210                 215                 220 acc ggc att gct tcc ctg gtc ctg ctg ggc ctg tgg gat tat ctg aac      722
Thr Gly Ile Ala Ser Leu Val Leu Leu Gly Leu Trp Asp Tyr Leu Asn
                    225                 230                 235 gag gct gcc atc acc act ttc tct gtc ctt ggg ctc ttc tcc tcc caa      770
Glu Ala Ala Ile Thr Thr Phe Ser Val Leu Gly Leu Phe Ser Ser Gln
                240                 245                 250 gct gcc gcc atc ctc agc acc ctc ctt gct gct gag gtc atc ccc acc      818
Ala Ala Ala Ile Leu Ser Thr Leu Leu Ala Ala Glu Val Ile Pro Thr
            255                 260                 265 act gtc cgg ggc cgt ggc ctg ggc ctg atc atg gct cta ggg gcg ctt      866
Thr Val Arg Gly Arg Gly Leu Gly Leu Ile Met Ala Leu Gly Ala Leu
        270                 275                 280 gga gga ctg agc ggc ccg gcc cag cgc ctc cac atg ggc cat gga gcc      914
Gly Gly Leu Ser Gly Pro Ala Gln Arg Leu His Met Gly His Gly Ala
285                 290                 295                 300 ttc ctg cag cac gtg gtg ctg gcg gcc tgc gcc ctc ctc tgc att ctc      962
Phe Leu Gln His Val Val Leu Ala Ala Cys Ala Leu Leu Cys Ile Leu
                    305                 310                 315 agc att atg ctg ctg ccg gag acc aag cgc aag ctc ctg ccc gag gtg     1010
Ser Ile Met Leu Leu Pro Glu Thr Lys Arg Lys Leu Leu Pro Glu Val
                320                 325                 330 ctc cgg gac ggg gag ctg tgt cgc cgg cct tcc ctg ctg cgg cag cca     1058
Leu Arg Asp Gly Glu Leu Cys Arg Arg Pro Ser Leu Leu Arg Gln Pro
            335                 340                 345 ccc cct acc cgc tgt gac cac gtc ccg ctg ctt gcc acc ccc aac cct     1106
Pro Pro Thr Arg Cys Asp His Val Pro Leu Leu Ala Thr Pro Asn Pro
        350                 355                 360 gcc ctc tga gcggcctctg agtaccctgg cgggaggctg gcccacacag             1155
Ala Leu
```

```
Ala Leu
365 aaaggtggca agaagatcgg gaagactgag tagggaaggc agggctgccc agaagtctca      1215 gaggcacctc acgccagcca tcgcggagag ctcagagggc cgtccccacc ctgcctcctc      1275 cctgctgctt tgcattcact tccttggcca gagtcagggg acagggagag agctccacac      1335 tgtaaccact gggtctgggc tccatcctgc gcccaaagac atccacccag acctcattat      1395 ttcttgctct atcattctgt ttcaataaag acatttggaa taaacgagca tatcatagcc      1455 tggac                                                                  1460

<210> SEQ ID NO 27
<211> LENGTH: 366
<212> TYPE: PRT
<213> ORGANISM: Homo sapiens

<400> SEQUENCE: 27

Met Ala Leu Arg Phe Leu Leu Gly Phe Leu Leu Ala Gly Val Asp Leu
1               5                   10                  15

Gly Val Tyr Leu Met Arg Leu Glu Leu Cys Asp Pro Thr Gln Arg Leu
            20                  25                  30

Arg Val Ala Leu Ala Gly Glu Leu Val Gly Val Gly His Phe Leu
        35                  40                  45

Phe Leu Gly Leu Ala Leu Val Ser Lys Asp Trp Arg Phe Leu Gln Arg
    50                  55                  60

Met Ile Thr Ala Pro Cys Ile Leu Phe Leu Phe Tyr Gly Trp Pro Gly
65                  70                  75                  80

Leu Phe Leu Glu Ser Ala Arg Trp Leu Ile Val Lys Arg Gln Ile Glu
                85                  90                  95

Glu Ala Gln Ser Val Leu Arg Ile Leu Ala Glu Arg Asn Arg Pro His
            100                 105                 110

Gly Gln Met Leu Gly Glu Glu Ala Gln Glu Ala Leu Gln Asp Leu Glu
        115                 120                 125

Asn Thr Cys Pro Leu Pro Ala Thr Ser Ser Phe Ser Phe Ala Ser Leu
130                 135                 140

Leu Asn Tyr Arg Asn Ile Trp Lys Asn Leu Leu Ile Leu Gly Phe Thr
145                 150                 155                 160

Asn Phe Ile Ala His Ala Ile Arg His Cys Tyr Gln Pro Val Gly Gly
                165                 170                 175

Gly Gly Ser Pro Ser Asp Phe Tyr Leu Cys Ser Leu Leu Ala Ser Gly
            180                 185                 190

Thr Ala Ala Leu Ala Cys Val Phe Leu Gly Val Thr Val Asp Arg Phe
        195                 200                 205

Gly Arg Arg Gly Ile Leu Leu Leu Ser Met Thr Leu Thr Gly Ile Ala
    210                 215                 220

Ser Leu Val Leu Leu Gly Leu Trp Asp Tyr Leu Asn Glu Ala Ala Ile
225                 230                 235                 240

Thr Thr Phe Ser Val Leu Gly Leu Phe Ser Ser Gln Ala Ala Ala Ile
                245                 250                 255

Leu Ser Thr Leu Leu Ala Ala Glu Val Ile Pro Thr Thr Val Arg Gly
            260                 265                 270

Arg Gly Leu Gly Leu Ile Met Ala Leu Gly Ala Leu Gly Gly Leu Ser
        275                 280                 285

Gly Pro Ala Gln Arg Leu His Met Gly His Gly Ala Phe Leu Gln His
    290                 295                 300
```

```
Val Val Leu Ala Ala Cys Ala Leu Leu Cys Ile Leu Ser Ile Met Leu
305                 310                 315                 320

Leu Pro Glu Thr Lys Arg Lys Leu Leu Pro Glu Val Leu Arg Asp Gly
            325                 330                 335

Glu Leu Cys Arg Arg Pro Ser Leu Leu Arg Gln Pro Pro Thr Arg
            340                 345                 350

Cys Asp His Val Pro Leu Leu Ala Thr Pro Asn Pro Ala Leu
            355                 360                 365

<210> SEQ ID NO 28
<211> LENGTH: 1195
<212> TYPE: DNA
<213> ORGANISM: Homo sapiens
<220> FEATURE:
<221> NAME/KEY: CDS
<222> LOCATION: (71)..(1024)
<223> OTHER INFORMATION:

<400> SEQUENCE: 28
ggcacgaggg gcccgggccc ccgccagcct ccctcctcgc gtccctcggt gtcctccgcg        60
ggccggcgcg atg cgg ctg ggc ccg agg acc gcg gcg ttg ggg ctg ctg        109
            Met Arg Leu Gly Pro Arg Thr Ala Ala Leu Gly Leu Leu
              1               5                  10 ctg ctg tgc gcc gcc gcg gcc ggc gcc ggc aag gcc gag gag ctg cac        157
Leu Leu Cys Ala Ala Ala Ala Gly Ala Gly Lys Ala Glu Glu Leu His
     15                  20                  25 tac ccg ctg ggc gag cgc cgc agc gac tac gac cgc gag gcg ctg ctg        205
Tyr Pro Leu Gly Glu Arg Arg Ser Asp Tyr Asp Arg Glu Ala Leu Leu
 30                  35                  40                  45 ggc gtc cag gaa gat gtg gat gaa tat gtt aaa ctc ggc cac gaa gag        253
Gly Val Gln Glu Asp Val Asp Glu Tyr Val Lys Leu Gly His Glu Glu
                 50                  55                  60 cag caa aaa aga ctg cag gcg atc ata aag aaa atc gac ttg gac tca        301
Gln Gln Lys Arg Leu Gln Ala Ile Ile Lys Lys Ile Asp Leu Asp Ser
             65                  70                  75 gat ggc ttt ctc act gaa agt gaa ctc agt tca tgg att cag atg tct        349
Asp Gly Phe Leu Thr Glu Ser Glu Leu Ser Ser Trp Ile Gln Met Ser
         80                  85                  90 ttt aag cat tat gct atg caa gaa gca aaa caa cag ttt gtt gaa tat        397
Phe Lys His Tyr Ala Met Gln Glu Ala Lys Gln Gln Phe Val Glu Tyr
     95                 100                 105 gat aaa aac agt gat gat act gtg act tgg gat gaa tat aac att cag        445
Asp Lys Asn Ser Asp Asp Thr Val Thr Trp Asp Glu Tyr Asn Ile Gln
110                 115                 120                 125 atg tat gat cgt gtg att gac ttt gat gag aac act gct ctg gat gat        493
Met Tyr Asp Arg Val Ile Asp Phe Asp Glu Asn Thr Ala Leu Asp Asp
                130                 135                 140 gca gaa gag gag tcc ttt agg aag ctt cac tta aag gac aag aag cga        541
Ala Glu Glu Glu Ser Phe Arg Lys Leu His Leu Lys Asp Lys Lys Arg
            145                 150                 155 ttt gaa aaa gct aac cag gat tca ggt ccc ggt ttg agt ctt gaa gaa        589
Phe Glu Lys Ala Asn Gln Asp Ser Gly Pro Gly Leu Ser Leu Glu Glu
        160                 165                 170 ttt att gct ttt gag cat cct gaa gaa gtt gat tat atg acg gaa ttt        637
Phe Ile Ala Phe Glu His Pro Glu Glu Val Asp Tyr Met Thr Glu Phe
    175                 180                 185 gtc att caa gaa gct tta gaa gaa cat gac aaa aat ggt gat gga ttt        685
Val Ile Gln Glu Ala Leu Glu Glu His Asp Lys Asn Gly Asp Gly Phe
190                 195                 200                 205
```

-continued

| | | |
|---|---|---|
| gtt agt ttg gaa gaa ttt ctt ggt gat tac agg tgg gat cca act gca<br>Val Ser Leu Glu Glu Phe Leu Gly Asp Tyr Arg Trp Asp Pro Thr Ala<br>210                              215                      220 | 733 |
| aat gaa gat cca gaa tgg ata ctt gtt gag aaa gac aga ttc gtg aat<br>Asn Glu Asp Pro Glu Trp Ile Leu Val Glu Lys Asp Arg Phe Val Asn<br>225                              230                      235 | 781 |
| gat tat gac aaa gat aac gat ggc agg ctt gat ccc caa gag ctg tta<br>Asp Tyr Asp Lys Asp Asn Asp Gly Arg Leu Asp Pro Gln Glu Leu Leu<br>        240                      245                      250 | 829 |
| cct tgg gta gta cct aat aat cag ggc att gca caa gag gag gca ctt<br>Pro Trp Val Val Pro Asn Asn Gln Gly Ile Ala Gln Glu Glu Ala Leu<br>255                              260                      265 | 877 |
| cat cta att gat gaa atg gat ttg aat ggt gac aaa aag ctc tct gaa<br>His Leu Ile Asp Glu Met Asp Leu Asn Gly Asp Lys Lys Leu Ser Glu<br>270                            275                    280                    285 | 925 |
| gaa gag att ctg gaa aac ccg gac ttg ttt ctc acc agt gaa gcc aca<br>Glu Glu Ile Leu Glu Asn Pro Asp Leu Phe Leu Thr Ser Glu Ala Thr<br>                      290                      295                      300 | 973 |
| gat tat ggc aga cag ctc cat gat gac tat ttc tat cat gat gag ctt<br>Asp Tyr Gly Arg Gln Leu His Asp Asp Tyr Phe Tyr His Asp Glu Leu<br>305                              310                    315 | 1021 |
| taa tctccgagcc tgtctcagta gagtactggc tccttttata atttgttacc | 1074 |
| agctttactt ttgtgataaa atattgatgt tgtattttac actcttaagt cttaaccaca | 1134 |
| gtcagaatta tcttaatgta gattataatt ttggtctttt aggaaaaaaa aaaaaaaaa | 1194 |
| a | 1195 |

<210> SEQ ID NO 29
<211> LENGTH: 317
<212> TYPE: PRT
<213> ORGANISM: Homo sapiens

<400> SEQUENCE: 29

Met Arg Leu Gly Pro Arg Thr Ala Ala Leu Gly Leu Leu Leu Leu Cys
1               5                    10                    15

Ala Ala Ala Gly Ala Gly Lys Ala Glu Glu Leu His Tyr Pro Leu
            20                    25                    30

Gly Glu Arg Arg Ser Asp Tyr Asp Arg Glu Ala Leu Leu Gly Val Gln
                35                    40                    45

Glu Asp Val Asp Glu Tyr Val Lys Leu Gly His Glu Glu Gln Gln Lys
50                              55                    60

Arg Leu Gln Ala Ile Ile Lys Lys Ile Asp Leu Asp Ser Asp Gly Phe
65                     70                    75                    80

Leu Thr Glu Ser Glu Leu Ser Ser Trp Ile Gln Met Ser Phe Lys His
                    85                    90                    95

Tyr Ala Met Gln Glu Ala Lys Gln Gln Phe Val Glu Tyr Asp Lys Asn
                100                  105                110

Ser Asp Asp Thr Val Thr Trp Asp Glu Tyr Asn Ile Gln Met Tyr Asp
        115                    120                    125

Arg Val Ile Asp Phe Asp Glu Asn Thr Ala Leu Asp Asp Ala Glu Glu
130                          135                    140

Glu Ser Phe Arg Lys Leu His Leu Lys Asp Lys Lys Arg Phe Glu Lys
145                    150                  155                    160

Ala Asn Gln Asp Ser Gly Pro Gly Leu Ser Leu Glu Glu Phe Ile Ala
                165                  170                175

Phe Glu His Pro Glu Glu Val Asp Tyr Met Thr Glu Phe Val Ile Gln
        180                    185                    190

```
Glu Ala Leu Glu Glu His Asp Lys Asn Gly Asp Gly Phe Val Ser Leu
        195                 200                 205

Glu Glu Phe Leu Gly Asp Tyr Arg Trp Asp Pro Thr Ala Asn Glu Asp
        210                 215                 220

Pro Glu Trp Ile Leu Val Glu Lys Asp Arg Phe Val Asn Asp Tyr Asp
225                 230                 235                 240

Lys Asp Asn Asp Gly Arg Leu Asp Pro Gln Glu Leu Leu Pro Trp Val
                245                 250                 255

Val Pro Asn Asn Gln Gly Ile Ala Gln Glu Glu Ala Leu His Leu Ile
                260                 265                 270

Asp Glu Met Asp Leu Asn Gly Asp Lys Lys Leu Ser Glu Glu Glu Ile
        275                 280                 285

Leu Glu Asn Pro Asp Leu Phe Leu Thr Ser Glu Ala Thr Asp Tyr Gly
        290                 295                 300

Arg Gln Leu His Asp Asp Tyr Phe Tyr His Asp Glu Leu
305                 310                 315
```